United States Patent
Ugbeye

(10) Patent No.: US 11,701,198 B2
(45) Date of Patent: Jul. 18, 2023

(54) FILTERING FACEPIECE RESPIRATOR

(71) Applicant: Tosan A. Ugbeye, Brunswick, OH (US)

(72) Inventor: Tosan A. Ugbeye, Brunswick, OH (US)

(73) Assignee: S.C.O.P.E. Medical, Inc., Brunswick, OH (US)

( * ) Notice: Subject to any disclaimer, the term of this patent is extended or adjusted under 35 U.S.C. 154(b) by 0 days.

(21) Appl. No.: 17/831,634

(22) Filed: Jun. 3, 2022

(65) Prior Publication Data

US 2022/0323174 A1  Oct. 13, 2022

Related U.S. Application Data

(62) Division of application No. 17/188,846, filed on Mar. 1, 2021, now Pat. No. 11,399,912.

(51) Int. Cl.
*A61B 90/00*  (2016.01)
*A62B 7/10*  (2006.01)
(Continued)

(52) U.S. Cl.
CPC .............. *A61B 90/05* (2016.02); *A41D 13/11* (2013.01); *A61M 16/0816* (2013.01);
(Continued)

(58) Field of Classification Search
CPC .... A61B 90/05; A41D 13/11; A41D 13/1138; A61M 16/0816; A61M 2202/0208; A61M 16/0093; A61M 2205/7509; A61M 2205/7518; A61M 16/0087; A61M 2210/005; A61M 2210/0625; A61M 16/085; A61M 16/208; A61M 2230/432; A61M 16/06; A61M 16/1005; A61M 16/1055; A61M 16/105–107; A62B 7/02;
(Continued)

(56) References Cited

U.S. PATENT DOCUMENTS

| | | |
|---|---|---|
| 8,042,540 B2 | 10/2011 | McDonald et al. |
| 8,365,734 B1 | 2/2013 | Lehman |

(Continued)

FOREIGN PATENT DOCUMENTS

| | | | |
|---|---|---|---|
| JP | 2000262621 | | 9/2000 |
| JP | 2000262621 A | * | 9/2000 |

OTHER PUBLICATIONS

VBM Endoscopy Mask, Bronchoscope Airway, https://www.vbm-medical.com/products/airway-management/endoscopy-mask/, published Nov. 14, 2015.

(Continued)

*Primary Examiner* — Elliot S Ruddie
(74) *Attorney, Agent, or Firm* — Emerson, Thomson & Bennett, LLC; Roger D. Emerson; Peter R. Detorre

(57) ABSTRACT

Provided is a filtering facepiece respirator. The respirator includes a mask body having an anterior side portion, a posterior side portion, a middle portion, a first side portion, a second side portion, a top side portion, a bottom side portion and outer edge portions. The respirator further includes a primary port positioned at the anterior middle portion of the mask body and a detachable primary port adapter which is positioned over and engages the primary port. The respirator may further include an oxygen port and oxygen port adapter and a luer port and luer port adapter.

19 Claims, 47 Drawing Sheets

(51) Int. Cl.
*A62B 9/00* (2006.01)
*A62B 18/08* (2006.01)
*A62B 23/02* (2006.01)
*A62B 7/02* (2006.01)
*A41D 13/11* (2006.01)
*A61M 16/10* (2006.01)
*B01D 39/16* (2006.01)
*A61M 16/08* (2006.01)

(52) U.S. Cl.
CPC ............. *A61M 16/105* (2013.01); *A62B 7/02* (2013.01); *A62B 7/10* (2013.01); *A62B 9/00* (2013.01); *A62B 18/08* (2013.01); *A62B 23/02* (2013.01); *B01D 39/1623* (2013.01); *A61M 2202/0208* (2013.01); *B01D 2239/0241* (2013.01); *B01D 2239/065* (2013.01)

(58) Field of Classification Search
CPC .. A62B 7/10; A62B 9/00; A62B 18/08; A62B 18/025; A62B 23/02–25; B01D 39/1623; B01D 2239/0241; B01D 2239/065; B01D 39/1692; B01D 2239/0622
USPC ............ 128/205.25, 202.28, 205.13, 205.29, 128/206.16, 206.17, 206.21, 206.28, 128/206.29
See application file for complete search history.

(56) References Cited

U.S. PATENT DOCUMENTS

| | | | |
|---|---|---|---|
| 8,960,195 B2 | 2/2015 | Lehman | |
| 11,000,655 B1 * | 5/2021 | Fox | .................. A61M 16/0616 |
| 2003/0024533 A1 | 2/2003 | Sniadach | |
| 2012/0247474 A1 | 10/2012 | Torbenson | |
| 2012/0285448 A1 * | 11/2012 | Dugan | .............. A61M 16/0605 |
| | | | 128/202.16 |
| 2013/0296653 A1 * | 11/2013 | Brown | .............. A61M 16/0825 |
| | | | 128/200.26 |
| 2016/0030695 A1 * | 2/2016 | Chang | ................... A61M 16/06 |
| | | | 128/205.25 |
| 2018/0110951 A2 * | 4/2018 | Beard | ................... A61M 16/06 |
| 2018/0133429 A1 * | 5/2018 | Reddy | ................. A61M 16/085 |
| 2018/0214651 A1 * | 8/2018 | McCracken | ......... A61B 1/2676 |

OTHER PUBLICATIONS

AerosoLess Scope Masks, "Scopemasks—Disposable Mask for Safe Diagnostic Procedures", https://aerosolessmedical.com/procedural-products/, published Sep. 11, 2020.

Procedural Oxygen Mask by POM Medical, LLC, https://proceduraloxygenmask.com/, published Aug. 18, 2019.

Moldex, Ideas that Wear Well, "N95", https://www.moldex.com/product-category/respiratory-protection/disposable-respirators/n95-respirators/, published Jun. 21, 2018.

International Search Report for corresponding PCT Application No. PCT/US2022/018167 dated Jun. 16, 2022.

Written Opinion for corresponding PCT Application No. PCT/US2022/018167 dated Jun. 16, 2022.

OxyMask, http://thebetteroxygenmask.com/oxymask/, OxyMask product advertised on website launched Dec. 1, 2004.

Airlife Open Oxygen Mask, https://www.vyaire.com/sites/us/files/2021-05/vyr-gbl-1900119-vy-airlife-open-brochure-global_final.pdf, May 1, 2021.

* cited by examiner

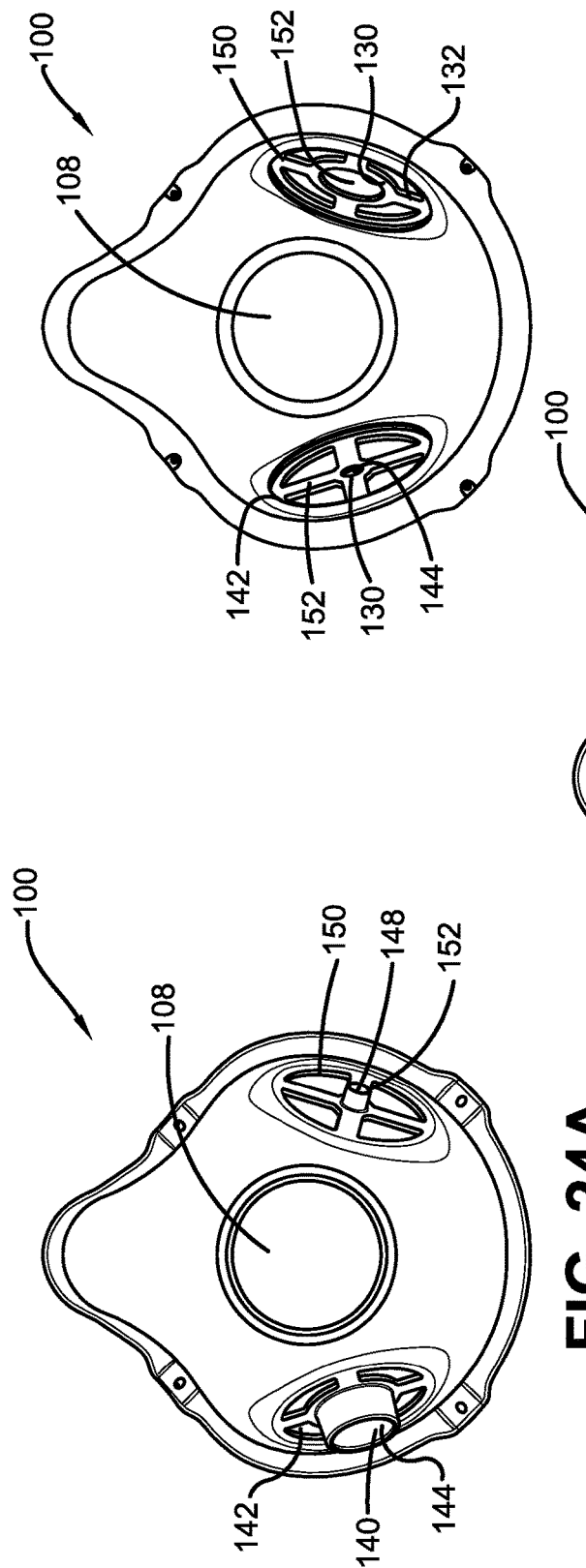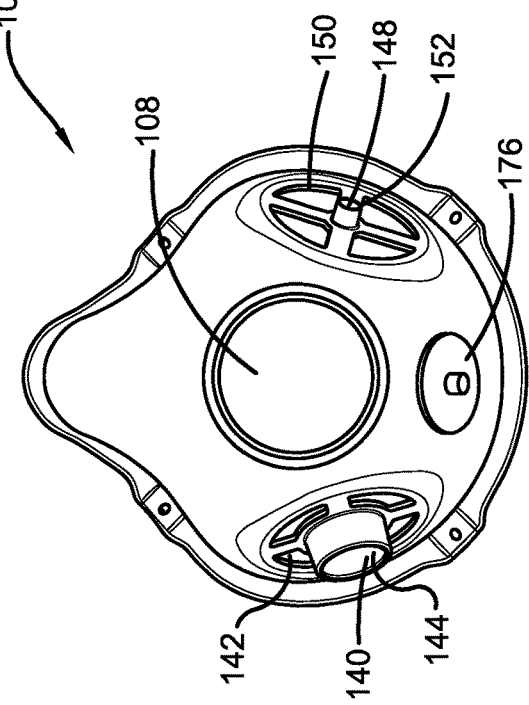

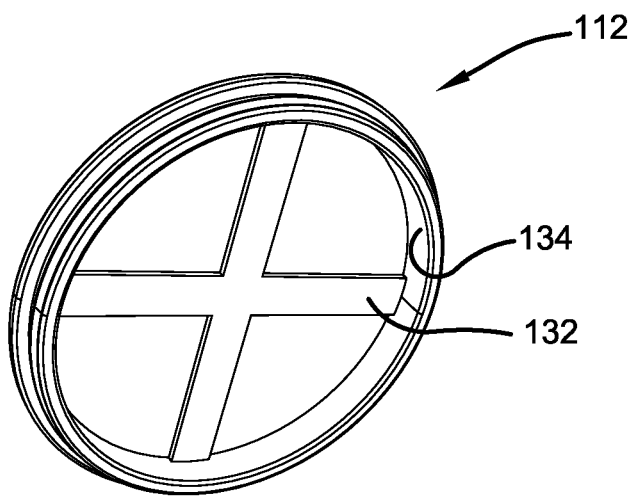
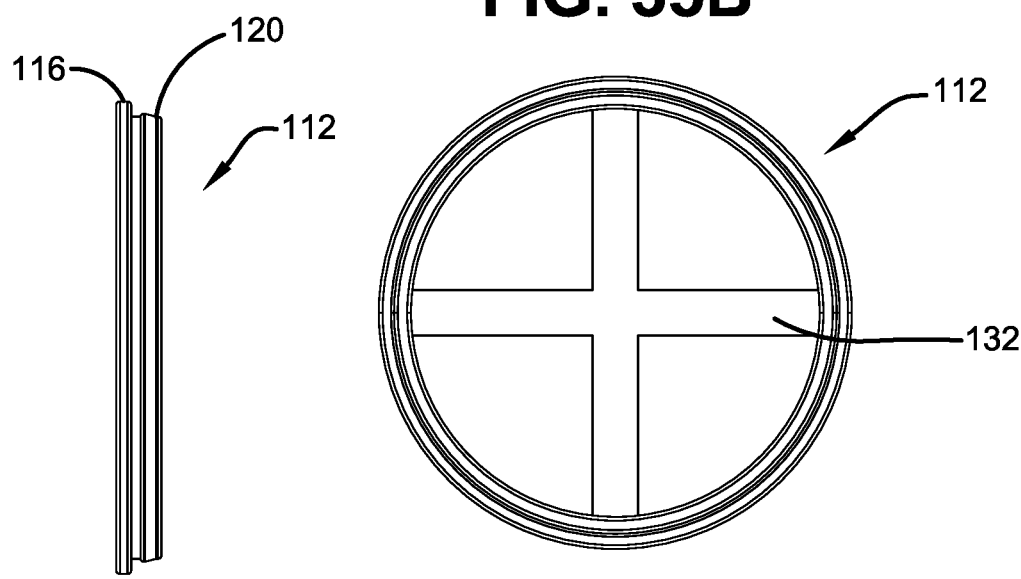
FIG. 35A
FIG. 35B
FIG. 35C
FIG. 35D

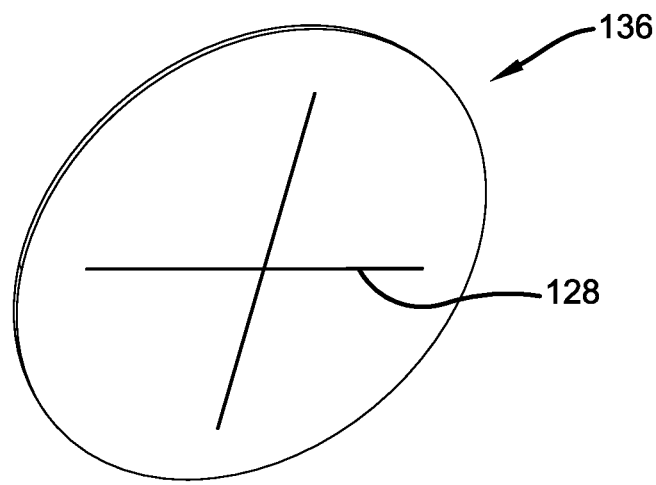
FIG. 37A
FIG. 37B
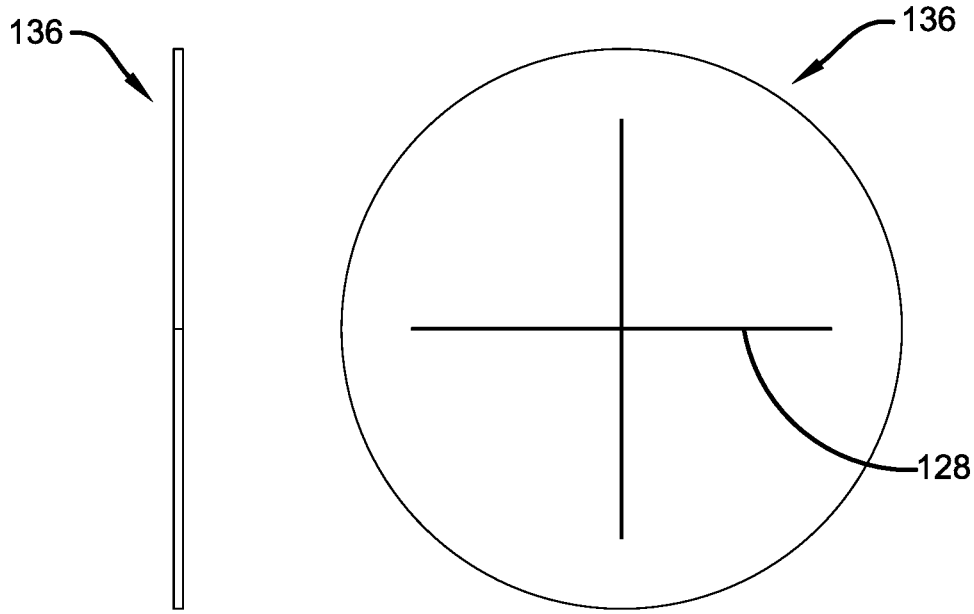
FIG. 37C  FIG. 37D

FIG. 40C
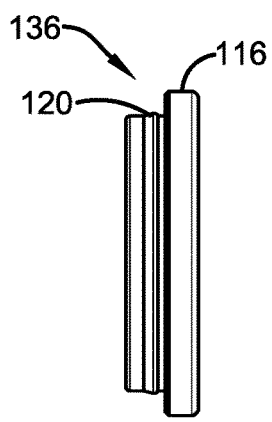
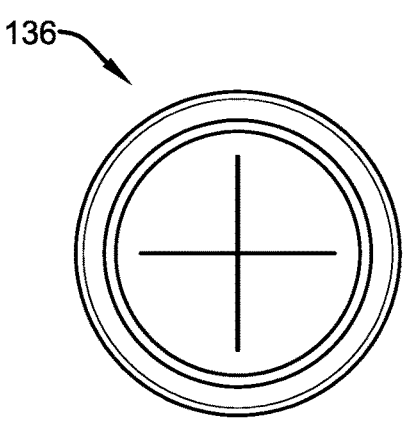
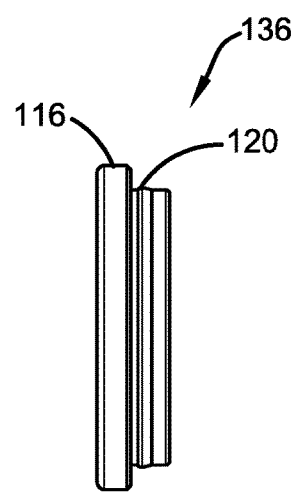
FIG. 40B   FIG. 40A   FIG. 40D
FIG. 40E
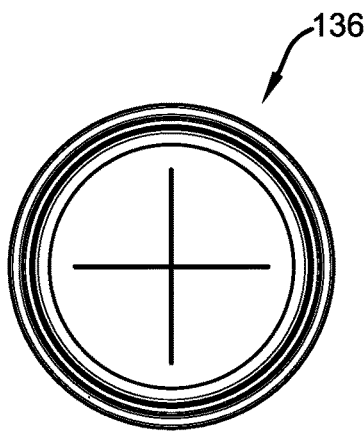
FIG. 41

FILTERING FACEPIECE RESPIRATOR

TECHNICAL FIELD

The present inventive disclosure is directed to various embodiments of a filtering facepiece respirator, also referred to herein as a mask and associated methods. The filtering facepiece respirator functions to provide oxygen delivery and filtration ability to reduce aerosol, respiratory droplet and microbial spread. The claims of the present application and the disclosure set forth herein cover a product and process related to COVID-19 and such product and processes are subject to applicable FDA approval for COVID-19 use.

BACKGROUND

The present invention relates to respirators, and more particularly to a filtering facepiece respirator mask (e.g., an N95 or other filtration rated mask) to be worn by patients during airway instrumentation, and a filtering facepiece respirator mask (e.g., N95 or other filtration rated mask) to be worn by patients before procedures, during airway instrumentation, and after procedures.

Healthcare workers are constantly exposed to respiratory droplets from patients whose airways have been instrumented by an endotracheal tube, laryngeal mask airway, endoscope and other medical devices.

Existing N95 respirator masks and other filtration rated masks do not protect clinicians from aerosolized respiratory droplets during instrumentation of the airway (for endoscopes), or during ventilation of the patient (for laryngeal mask airways and, to a lesser extent, endotracheal tubes), exposing both the patient and clinicians to viruses and other hazardous micro particles.

Aerosolization of respiratory droplets during ventilation constantly exposes everyone around a patient to said hazards, making breathing devices, especially laryngeal mask airways (that are not secured in the trachea and do not create complete seals around the trachea), dangerous to clinicians taking care of a ventilated patient.

Existing N95 respirator masks and other filtration rated masks do not work well because they have no way of creating a valid seal around the instrumenting device and the patient's face. As can be seen, there is a need for a solution to at least one of the aforementioned problems.

BRIEF DESCRIPTION OF THE DRAWINGS

FIG. 24A is a front view of a base mask of an exemplary embodiment of a filtering facepiece respirator.

FIG. 24B is a front view of a base mask of an exemplary embodiment of a filtering facepiece respirator with an exhalation valve in the body of the mask.

FIG. 25 is a back view of a base mask of an exemplary embodiment of a filtering facepiece respirator.

FIGS. 35A through 35D are respectively, a perspective view, a top or bottom view, a side view and a front view of an exemplary adapter for an exemplary embodiment of a filtering facepiece respirator.

FIGS. 37A through 37D are respectively, a perspective view, a top or bottom view, a side view and a front view of an exemplary seal for an exemplary embodiment of a filtering facepiece respirator.

FIGS. 40A through 40E are respectively, a front view, a first side view, a top view, a second side view and a bottom view of an exemplary adapter for an exemplary embodiment of a filtering facepiece respirator.

FIG. 41 is a front view, a first side view, a top view, a second side view and a bottom view of an exemplary adapter for an exemplary embodiment of a filtering facepiece respirator.

DETAILED DESCRIPTION

Figure 1:
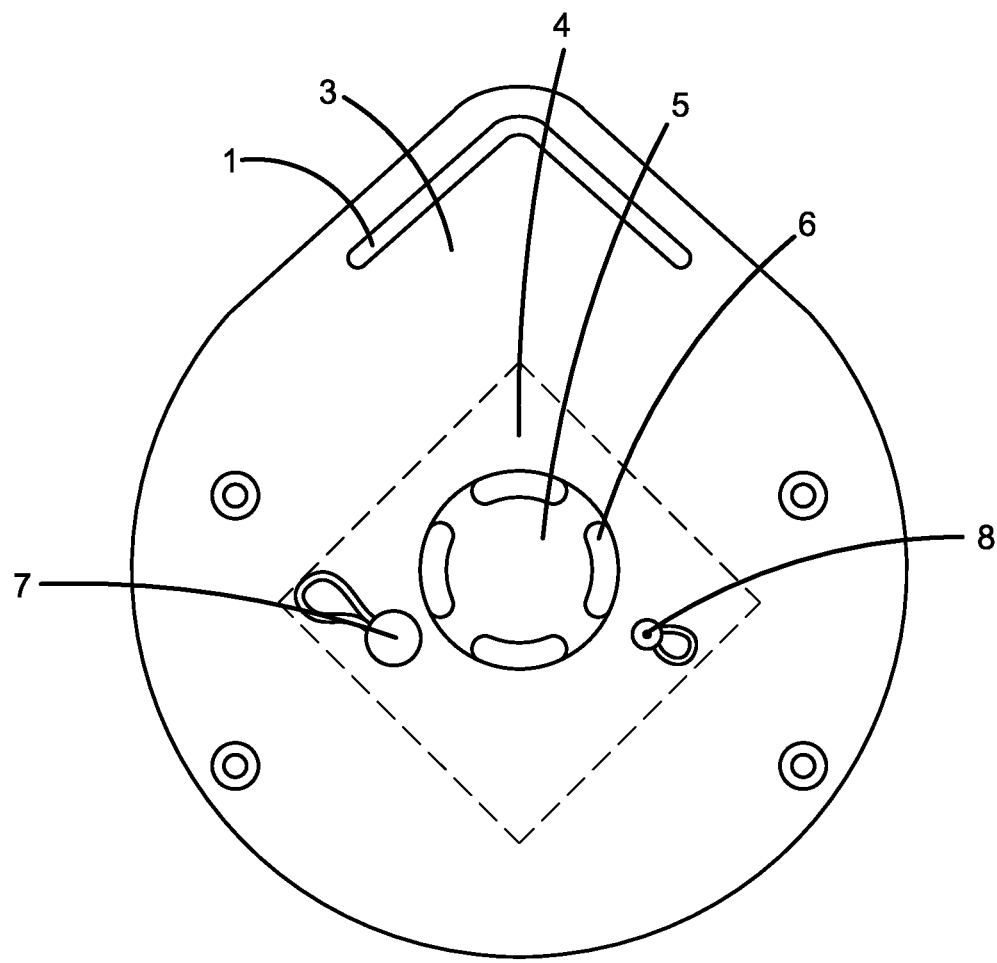
FIG. 1 is a front isometric view of an exemplary embodiment of a filtering facepiece respirator.
Figure 2:
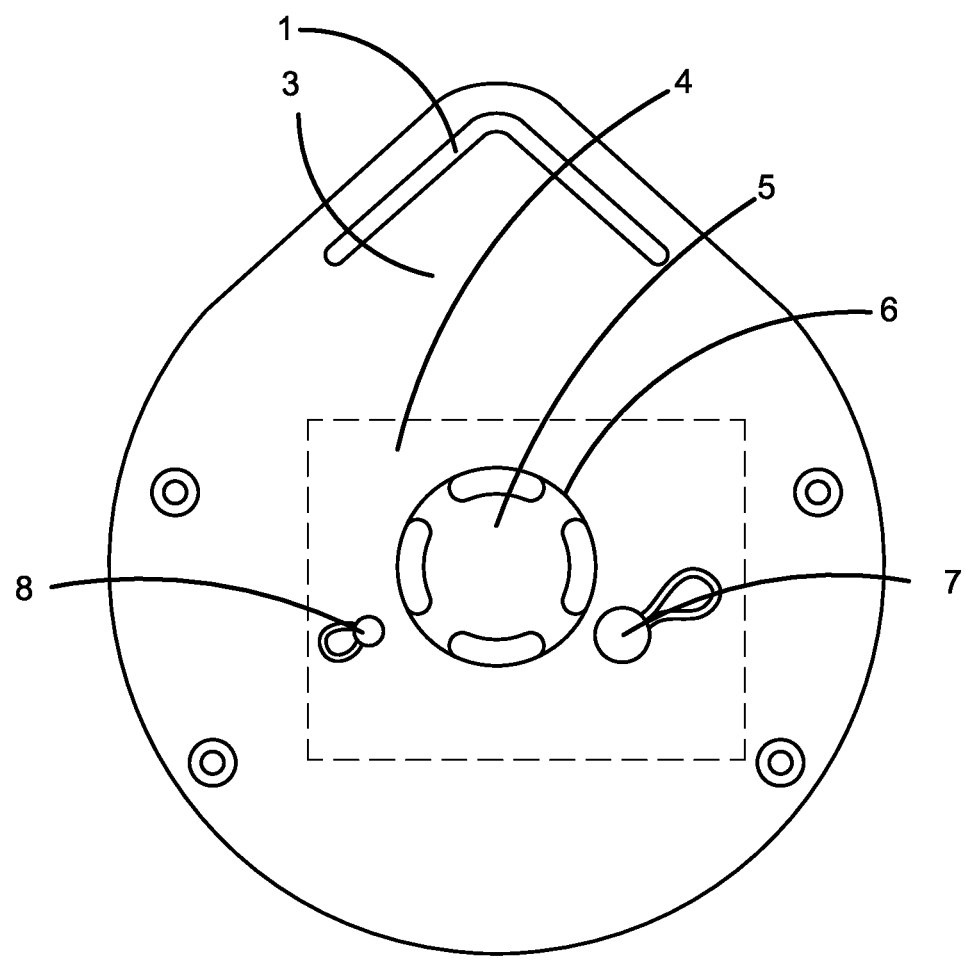
FIG. 2 is a front isometric view of an exemplary embodiment of a filtering facepiece respirator.
Figure 3:
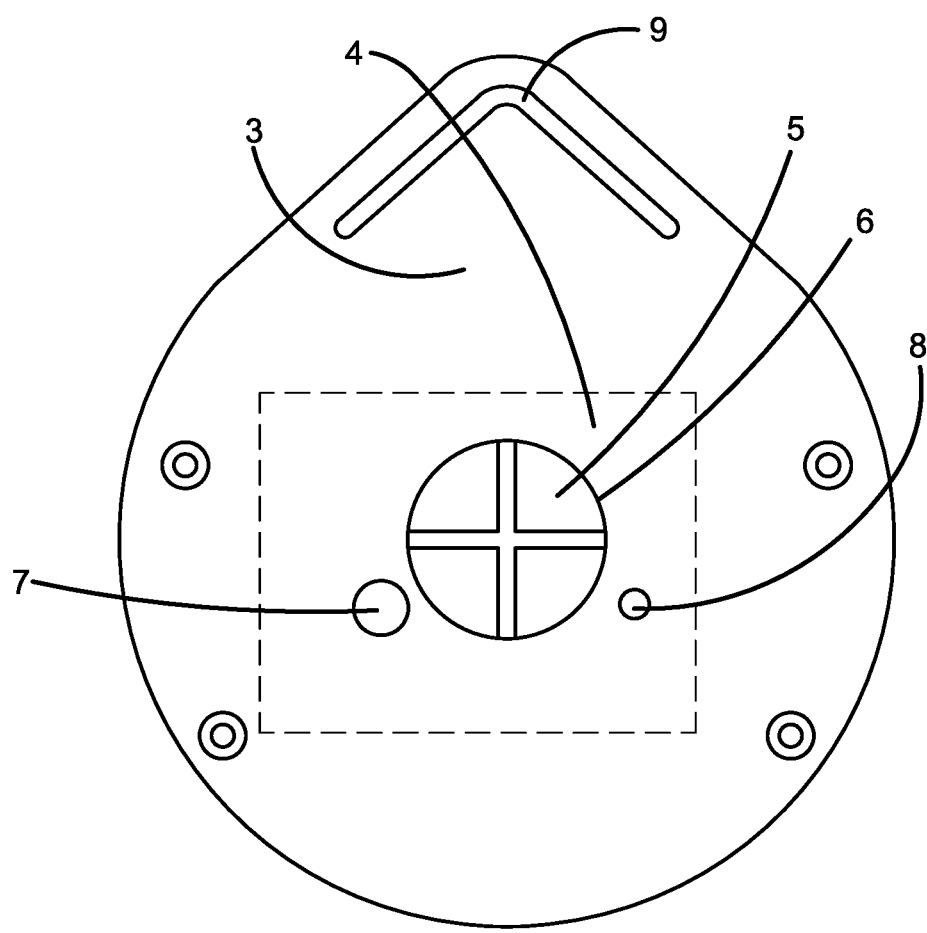
FIG. 3 is a rear isometric view of an exemplary embodiment of a filtering facepiece respirator.
Figure 4:
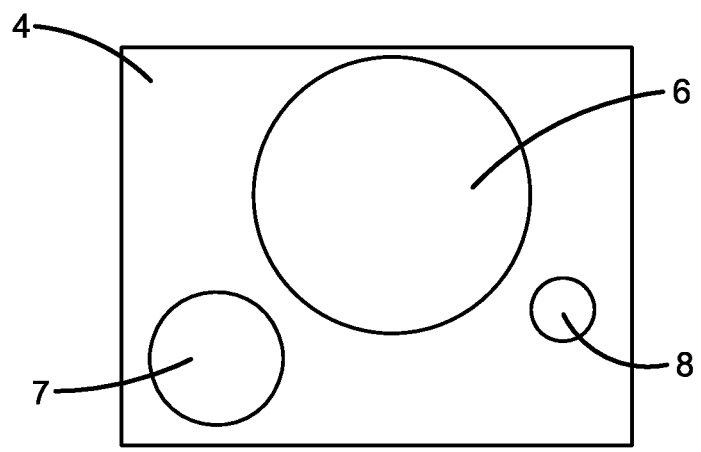
FIG. 4 is a schematic view of an exemplary embodiment of a filtering facepiece respirator.
Figure 5:
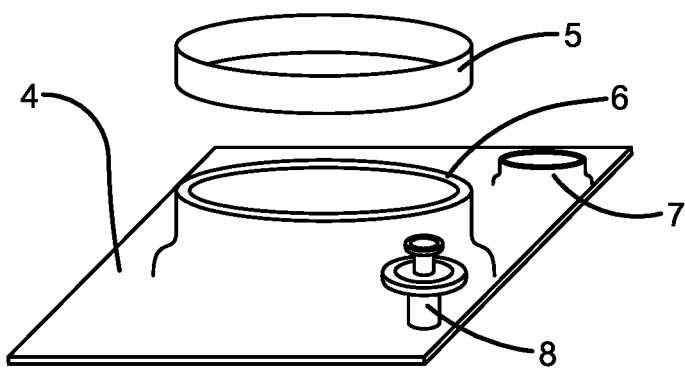
FIG. 5 is a side view of an exemplary embodiment of a filtering facepiece respirator.
Figure 6:
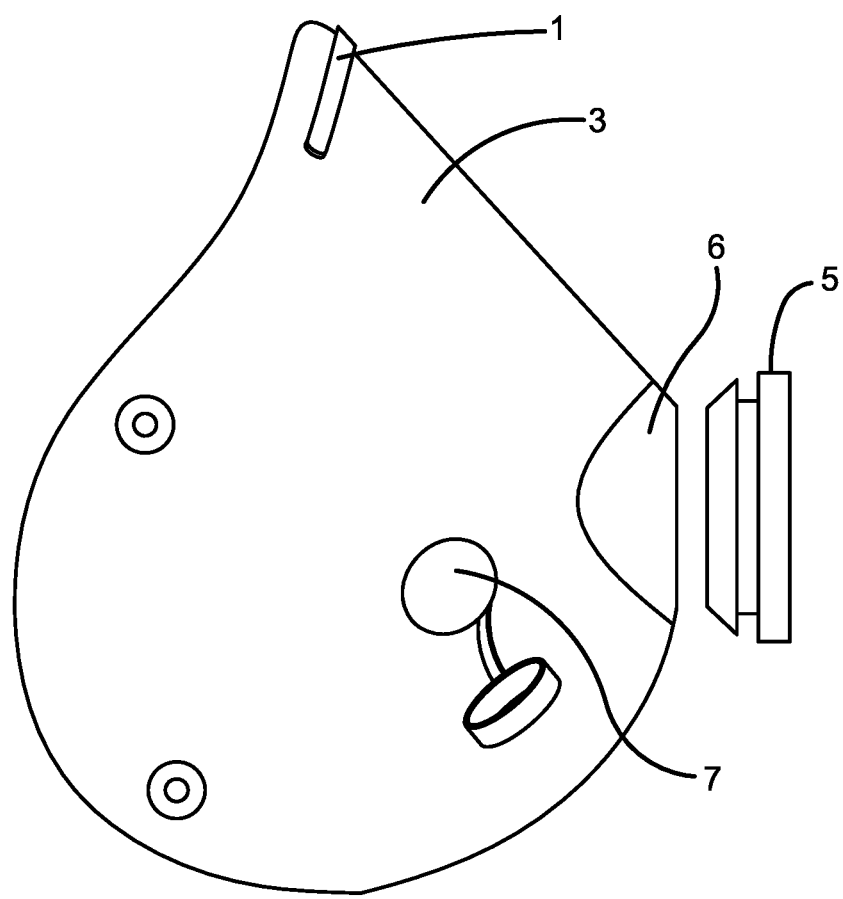
FIG. 6 is a side view of an exemplary embodiment of a filtering facepiece respirator.
Figure 7:
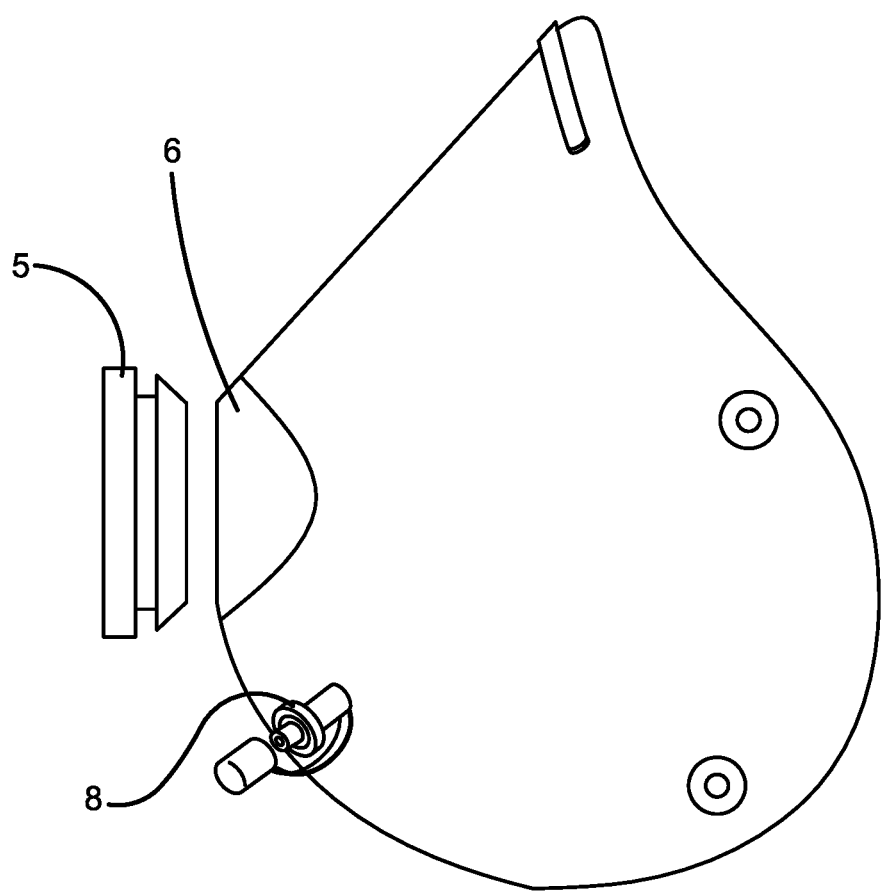
FIG. 7 is a side view of an exemplary embodiment of a filtering facepiece respirator
Figure 8:
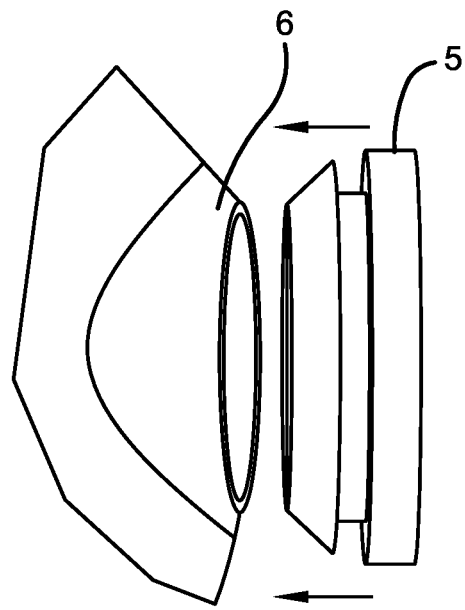
FIG. 8 is a partial side view of an exemplary embodiment of a filtering facepiece respirator.
Figure 9:
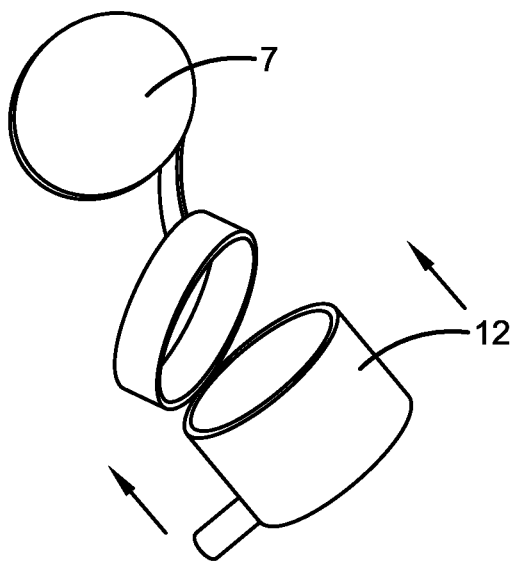
FIG. 9 is a perspective view of an exemplary embodiment of a filtering facepiece respirator.
Figure 10:
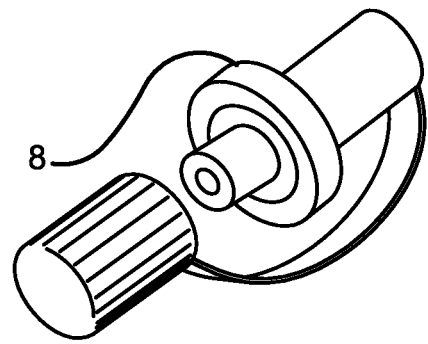
FIG. 10 is a side view of an exemplary embodiment of a filtering facepiece respirator.
Figure 11:
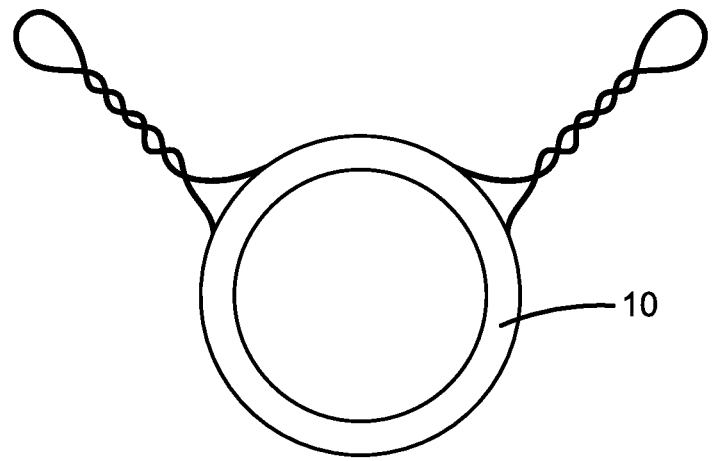
FIG. 11 is a front view of an exemplary embodiment of a filtering facepiece respirator.
Figure 12:
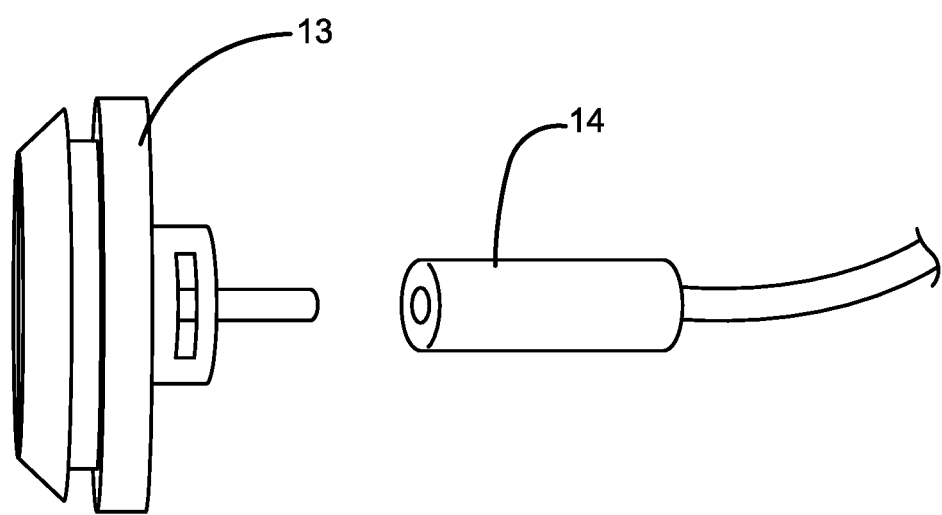
FIG. 12 side view of an exemplary embodiment of a filtering facepiece respirator.
Figure 13:
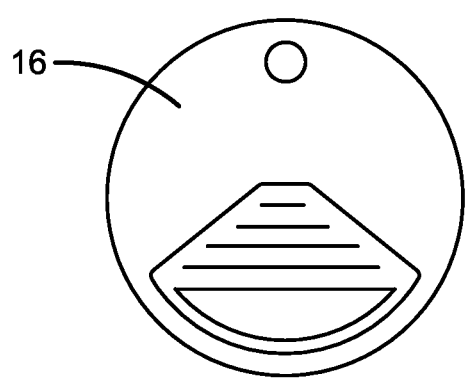
FIG. 13 is a front view of an exemplary embodiment of a filtering facepiece respirator.
Figure 14:
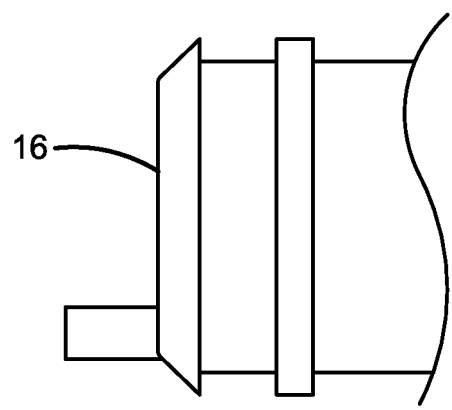
FIG. 14 is a side view of an exemplary embodiment of a filtering facepiece respirator.
Figure 15:
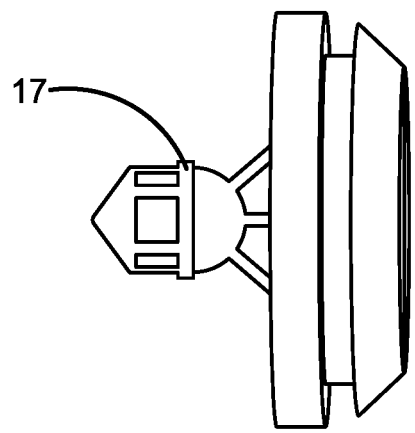
FIG. 15 is a side view of an exemplary embodiment of a filtering facepiece respirator.

The following detailed description is of the best currently contemplated modes of carrying out exemplary embodiments of the invention. The description is not to be taken in a limiting sense but is made merely for the purpose of illustrating the general principles of the present invention.

Broadly, an embodiment of the present disclosure provides a filtering facepiece respirator mask to be worn by patients before procedures, during airway instrumentation, and after procedures.

The filtering facepiece respirator includes designs for various types of uses including Endotrachael Tube (ETT) placement while the mask is on, ETT extubation with the mask on and maintenance while the ETT is in place, Laryngeal Mask Airway (LMA) placement while the mask is on, LMA removal with the mask on and maintenance while the LMA is in place, Aerosol generating procedures (AGPs) including but not limited to EGDs, bronschoscopies, TEE placement and other medical scopes. The mask may be used for procedures where there is access to the patient's face including procedures that require no sedation, some sedation and Monitored Anesthesia Care (MAC). The mask may be used for procedures which require patients to wear a mask before procedures to protect the patient (protection function) and to protect providers and other people around the patient (isolation function), for oxygen supplementation during procedures and during recovery. The mask may also provide breathing detection and other vital signs monitoring by attaching accessories to the ports within the mask.

An exemplary embodiment of the present disclosure provides a solution to several problems. Healthcare workers are constantly exposed to respiratory droplets from patients whose airways have been instrumented by an endotracheal tube, laryngeal mask airway, endoscope and other medical devices. The respirator mask may be placed on the patient prior to the medical procedure providing protection to both the patient and the clinician. The respirator mask creates a full seal around the patient's face after instrumentation of the airway.

Existing N95 respirator masks and masks of other filtration ratings do not protect clinicians from aerosolized respiratory droplets during instrumentation of the airway (for endoscopes), or during ventilation of the patient (for laryngeal mask airways and, to a lesser extent, endotracheal tubes), exposing both the patient and clinicians to viruses and other hazardous micro particles. Aerosolization of respiratory droplets during ventilation constantly exposes everyone around a patient to said hazards, making breathing devices, especially laryngeal mask airways (that are not secured in the trachea and do not create complete seals around the trachea), dangerous to clinicians taking care of a ventilated patient. The respirator mask disclosed herein distinguishes over the previously available devices by creating additional filter/sealing layers around both the instrumenting device and the patient's face.

The respirator mask disclosed herein is placed on the patient (preferably prior to the procedure), protects both the patient and the clinician prior to the procedure, and creates a full seal around the patient's face after instrumentation of the airway. The mask also allows for multiple adapters to be used for administration of oxygen, measuring $CO_2$, providing expiratory pressure for stenting open airways and more.

During periods of heightened awareness like during flu season, or other viral or bacterial outbreaks, surgical masks maybe placed on patients in the hospital to mitigate the spread of infectious droplets. However, while these masks may protect others, they do not offer optimal protection for the patients as they do not filter out viruses and other smaller harmful particles.

This mask serves several purposes by keeping both the patients and the whole hospital protected while they are awaiting procedures. The mask keeps patients and clinicians protected during airway instrumenting procedures. It also keeps patients and the entire hospital protected after the procedures, while providing functional features including but not limited to oxygen delivery, positive pressure to assist breathing, spirometry, nebulized medication delivery etc.

In an exemplary embodiment, provided is an adjustable respirator mask which has a microfiber filter that prevents inhalation of micro particles, including viruses. The mask may have a filtration rating of N95 or a rating in accordance with any other filtration standard within the industry. The mask includes a middle portion which includes an attachable circular or oval plastic piece. In certain embodiments, the circular or oval plastic piece may include a detachable exhalation valve. Around the plastic piece, on the front or anterior portion of the mask, extra collapsed (corrugated) filtering layers may be present. These filtering layers may include a top elastic nylon layer, which can be unfurled using attached drawstrings. The extra filtering layers can then be sealed around the stem of the instrumenting device. The posterior outer edges of the mask may also contain a nylon material that can be unraveled around the mask to achieve an enhanced seal around the patient's face. The anterior, outer edges of the mask may contain a tape-like adhesive than can be unraveled to place over the outer nylon for a full seal.

The filtering facepiece respirator provides several benefits over existing respirators. First, the filtering facepiece respirator remains on a patient's face during a medical procedure to reduce the amounts of droplets in the air from aerosol generating procedures. Second, because respirator need not be removed from the patient's face when inserting or removing a medical instrument into or out the buccal cavity, the respirator offers a seamless transition from the waiting room to the procedure room and through the recovery room and outside the hospital. The respirator also provides a novel aperture/base unit on the front of the mask that allows for attachment of a multitude of devices with varying functions across several industries.

The filtering facepiece respirator is also capable of providing the utility and convenience of existing respirator masks (including that of N95 respirator masks), while also providing a novel slot for medical instruments in the oropharynx, and additional silicone layers for enhanced sealing around the lumen of medical instruments and around the patient's face.

While some existing N95 masks may already come with exhalation valves, the filtering facepiece respirator disclosed herein provides a universe of additional functionality in that exhalation valves may be detached in particular situations (like when instrumenting an airway with medical devices), and variety of different complementary accessory devices may replace the exhalation valve on the mask or alternatively may be attached to the mask. The exhalation valve and complementary accessory devices are thus interchangeable with the orifices on the mask. Such complementary accessory devices may be used for delivering oxygen, delivering nebulized medications, taking breath sample and $CO_2$ monitoring.

In certain embodiments, the filtering facepiece respirator may possess additional covered orifices or slots. For example, the filtering facepiece respirator may possess one or two additional orifices or slots. An additional orifice or slot may allow for fitting the orifice or slot with a connector for oxygen delivery, suctioning, or the like, during a procedure. An additional orifice or slot may allow for fitting the orifice or slot with a female luer lock for capnography functions.

The filtering facepiece respirator differs from and provides several advantages over current respirators. The present invention provides the utility and convenience of existing N95 respirator masks, while also providing a novel slot allowing for insertion of medical instruments in the oropharynx. It also provides additional silicone, polypropylene, polycarbonate, nylon layers, and/or any other suitable plastic materials for enhanced sealing and filtration of micro particles around both the instrumenting device and the patient's face during medical procedures and other uses. Existing N95 respirator masks and masks of other filtration ratings do not work well because they have no way of creating a valid seal around the instrumenting device and the patient's face. The filtering facepiece respirator provides N95 functionality and improves on existing devices by creating additional filter/sealing layers around both the instrumenting device and the patient's face.

Referring now to FIGS. 1-20, in an exemplary embodiment, the filtering facepiece respirator includes the following components:

FIRST LISTING OF REFERENCE NUMBERS AND VARIOUS COMPONENTS

1. Nose clip (1)
2. Adjustable elastic bands with buttons (2)
3. Filtering media body with surrounding polyester layers for support (3)
4. Clear, plastic base that hosts parts (5), (6), (7) and (8)-(4)
5. Detachable plastic plate with or without exhalation valve (5)
6. Aperture/Base unit for attachment of multiple devices (6)
7. Capped slot for oxygen/suction delivery (7)
8. Capped, female luer lock for capnography measurement (8)

In a further exemplary embodiment, the mask of the present invention further includes the following optional elements:

SECOND LISTING OF REFERENCE NUMBERS AND VARIOUS ADDITIONAL COMPONENTS CONTINUED BELOW

9. Foam pad for nose clip (9) (best seen at FIG. 3)
10. Silicone sleeve with drawstrings around loop, and an adhesive layer (10) (best seen at FIGS. 11 and 18)
11. Enhanced sealing silicone layer with adhesive strip (11) (best seen in FIG. 19)
12. 90-degree adapter for oxygen/suction delivery (12) (best seen at FIG. 9)
13. Adapter that replaces detachable plate for oxygen delivery (13) (best seen at FIG. 12)
14. Oxygen tubing (14) (best seen at FIG. 12)
15. Capnography tubing (15)
16. Adapter for nebulized medications/substances (16) (best seen at FIGS. 13-14)
17. PEEP valve attachment (17) (best seen at FIG. 15)
18. Device for taking breath samples with vacuum tubes (not shown in the FIGS.
19. Electronic device for measurement of spirometry/$CO_2$/temperature, or the like (19) (best seen at FIG. 16)
20. Device for humidifying and/or vaporizing substances like menthol/breath fresheners, or the like
21. Electronic breathalyzer device
22. Electronic nicotine delivery system (22) shown at FIG. 20
23. Device for UV light and other similar forms of treatment
24. Accessory pieces to be attached to the mask, via buttons, like flags, hoods, hijabs, other masks, logos, plates, different fabrics, or the like (not shown in the Figures); and
25. Non-rebreather bag with oxygen connector (not shown in the Figures).

In an exemplary embodiment, the filter media (3) forms the body of the filtering facepiece respirator. The filter media (3) surrounds a clear, plastic base (4) in the middle of the filtering facepiece respirator. The clear plastic base (4) functions as a support base for components (5), (6), (7) and (8) described in further detail below. Also provided are adjustable elastic bands (2) which, according to certain aspects of the present teaching, are attached to the body filtering facepiece respirator by four buttons. The buttons have a loop that allows the elastic bands to be tightened or loosened. However, it is understood that the bands may be attached to the body of the mask by any suitable means within the skill of a person of knowledge in the art. The filtering facepiece respirator may also be provided with a nose clip (1). The nose clip (1) is positioned at the middle top portion of the body of the mask where the patient's nose would be positioned. The filtering facepiece respirator includes a detachable plastic plate (5) positioned at the middle portion of the front or posterior side of the respirator overlaying a patient's mouth behind it. The detachable plastic plate (5) is secured to a base unit/base unit aperture (6) (used for attaching a variety of devices) with a male-to-female fit mechanism (e.g., a snap connection).

The filtering facepiece respirator also includes a silicone sleeve (10). The silicone sleeve includes a proximal open end and a distal open end. The distal open end of the silicone sleeve (10) includes a loop through which drawstrings are passed through. The proximal open end of the silicone sleeve (10) is secured over the detachable plastic plate (5). In certain embodiments, an adhesive layer (11) is applied around the edges of the proximal open end of the silicone sleeve. The silicone sealing sleeve (10) and adhesive (11) may be attached to the detachable plastic plate (5) for extra protection depending on usage.

The filtering facepiece respirator may also be provided with a 90-degree oxygen adapter (12) for oxygen delivery and suction. The oxygen adapter (12) may be attached to detachable plastic plate (5) of the respirator when needed depending on the usage. In other embodiments, the oxygen adapter may be attached directly to the base unit aperture (6). Other devices may be attached to either the base unit aperture (6) or the detachable plastic plate (5) for added functionality.

Figure 17:
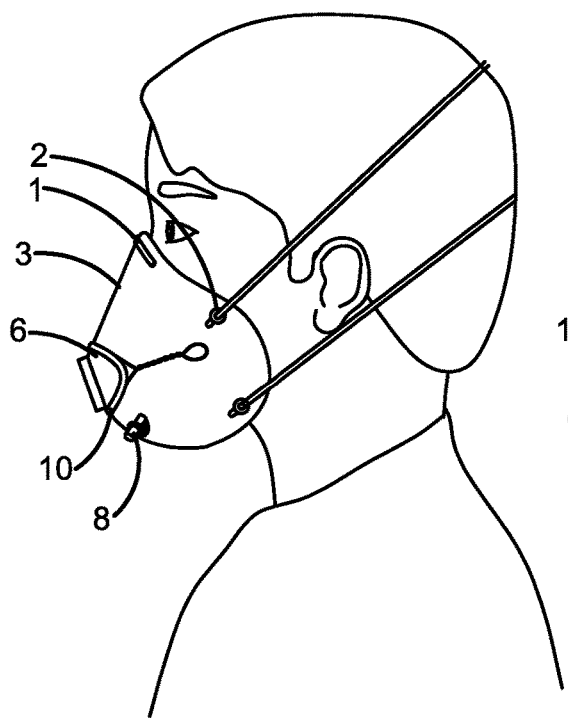
FIG. 17 is a side view of an exemplary embodiment of a filtering facepiece respirator.
Figure 19:
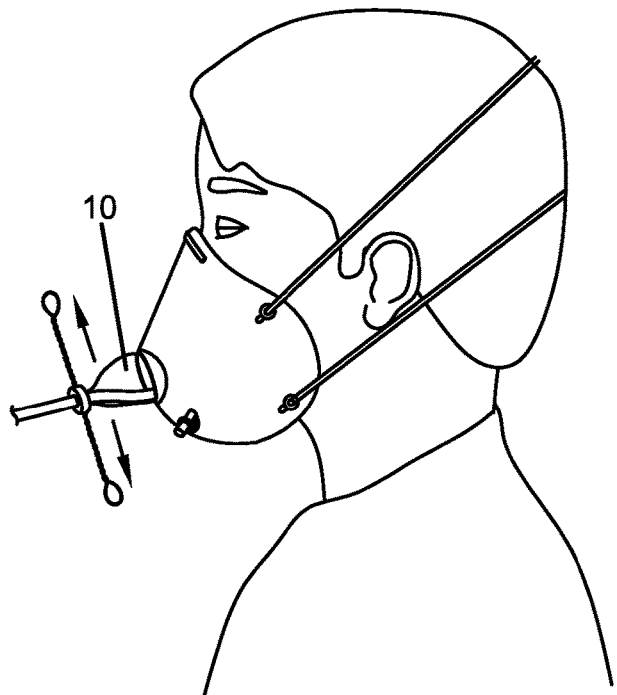
FIG. 19 is a side view of an exemplary embodiment of a filtering facepiece respirator.
Figure 20:
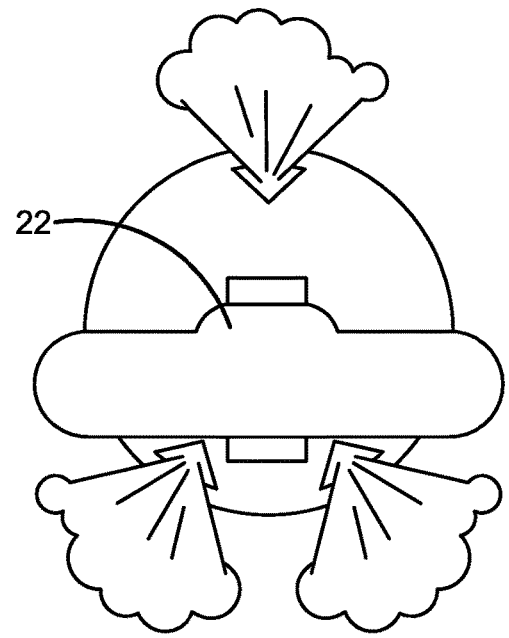
FIG. 20 is a side view of an exemplary embodiment of a filtering facepiece respirator.

In use, as shown in FIGS. 17 and 19, the body of the filtering facepiece respirator is placed on the patient's face and secured on the patient's head by securing elastic bands (2) behind the head and the back of the neck. The filter media body (3) surrounds a clear, plastic base (4) that houses the base unit and base unit aperture (6), an oxygen delivery orifice or slot (7) and an orifice or slot for a capnography luer connector (8). The nose clip (1) conveniently seals the body of the respirator around the patient's nose. Prior to instrumenting the airway, the mask may be taken off the patient's face by snapping off the buttons holding the elastic bands to the body of the mask. Alternatively, the detachable plastic plate (5) can be removed from the base unit aperture (6) with the mask still secured on the patient's face. The silicone sleeve (8) may then be secured to the respirator around the aperture/base unit (6). Alternatively, the silicone sleeve (8) may be secured to the base unit aperture (6) while the respirator is covering the patient's face. An enhanced sealing silicone adhesive layer (11) may also be used to attach and secure the sleeve (8) to the edges of the base unit aperture (6).

In certain embodiments, the base unit aperture within the base unit (6) is circular and includes a rib within the inner circumference of the aperture. The detachable plastic plate (5) may be in the form of a conduit and may be tubular and circular in nature. The detachable plastic plate may include a first proximal open end and a second distal open end. The first proximal open end may include a tapered rib around the circumference of the proximal open end. The tapered rib may provide a snap fitting within the aperture within the base unit by coming in contact with and passing through the rib within the aperture within the base unit (6). As it passes through, the rib the plastic plate (5) may rest behind the rib within aperture of the base unit. The plastic (5) plate may further include a rim at its second distal end which has a circumference which is larger than the circumference of the aperture of the base unit (6). This allows the plastic plate (5) to engage the base unit aperture within the base unit (6) in the manner of a snap fitting.

The filtering facepiece respirator described above is highly adaptable in that its features may include a number of variations and in that the respirator may be used in a variety of different manners. A summary of additional features and capabilities the filtering facepiece respirator is provided below.

1. During certain medical procedures, it may be necessary to tuck a suction tubing on low suction, underneath the respirator to prevent retention and rebreathing of $CO_2$. The filtering facepiece respirator is fully capable of allowing suction tubing to be tucked under the respirator for this purpose while maintaining an effective seal around the patient's face. In certain embodiments, the edges of the filtering facepiece respirator are capable of being molded or shaped around such tubing to maintain the seal around the patient's face.

2. According to certain aspects of the present disclosure, the body of the filtering facepiece respirator may be made from an electroceutical fabric. In embodiments where filter media is used to form the body of the respirator, the filter media may also constitute an electroceutical fabric.
3. The elastic bands (2) may optionally be placed as loops behind the ears. The elastic bands may also be made with buttons which attach to the body of the respirator to enable ease of removal when instrumenting the airway. Such buttons may be snap buttons, buttons which fit within a slot, or any other suitable button known to a person having knowledge in the art. The body of the respirator may include button connectors which are capable of engaging corresponding button connectors on the band to achieve a snap connection. In other embodiments, the body of the respirator or the band may include a circular button and a corresponding slot may be present on the band or the body of the respirator receiving the circular button.
4. As mentioned above, the distal end of the silicone sleeve (10) may include drawstrings for attaching the distal end of the sleeve around a medical instrument. The drawstrings may be pulled to tighten the sleeve and close the diameter of the open distal end of the sleeve around the instrument to form a seal. It is contemplated that in some cases an adhesive tape, rubber band, or similar device may be used and positioned around the open distal end of the sleeve (10) to provide a stronger seal around the stem of the instrumenting device.
5. Extra filtering and adhesive sealing layers (11) may be made from polypropylene, nylon, combinations of polypropylene and nylon, or any other suitable material with similar functionality.
6. Alternatively, the clear plastic base (4) and the detachable plastic plate (5) may be made with a sealable slot that accommodates the instrumenting device without them being detachable. In certain embodiments, the slot may be sealable with the application of heat or hot air.
7. The clear plastic base (4) and the detachable plastic plate (5) may be made from any material other than plastic deemed suitable by a person of skill in the art.

Other devices such as those illustrated within FIGS. 12-16 may replace the detachable plate (5) when it is not intended to place an instrument in the patient's airway. Examples of such devices which may engage the base unit aperture (6) include but are not limited to an adapter for oxygen delivery (13) and corresponding oxygen tubing (14), tubing including tubing for capnography, an adapter for nebulized medications and substances (16), a PEEP valve attachment (17), a device for taking breath samples with vacuum tubes (18), an electronic device for measuring spirometry/$CO_2$/temperature or the like (19), a device for humidifying and/or vaporizing substances like menthol/breath fresheners or the like (20), an electronic breathalyzer device (21), an electronic nicotine delivery system (22), and a device for UV light and other similar forms of treatment (23).

It is contemplated that during some medical procedures, an extra layer of protective fabric (for example, without limitation, cotton, polypropylene, nylon, or the like) may be necessary to cover the front of the respirator while the exhalation valve remains to prevent expulsion of respiratory droplets.

The body of the respirator may include multiple microfiber filtering layers of varying thickness. The body of the respirator may be formed from one or more polyfiber compositions (e.g., polypropylene and polyester) that provide rigidity and filtering functionality. A melt blown/spun bound process may be used for manufacturing the polypropylene layers.

The base unit (6) of the respirator may be made from a clear, medical grade plastic or any other suitable material.

In use, the filtering facepiece respirator may be left on the patient's face during instrumentation of the airway, especially in relation to endoscopes and TEE probes. However, it is also contemplated that the filtering facepiece respirator may be easily and quickly removed by unsnapping or disengaging the buttons when needed during medical procedures.

It is contemplated that extra filtering and adhesive sealing layers (11) may also be attached to the posterior portion of the mask and unraveled with strings.

In use, the filtering facepiece respirator serves a dual purpose by keeping patients protected while awaiting procedures and during airway instrumenting procedures. Clinicians are also protected. The respirator may be worn by the patient prior to the procedure. At the time of instrumenting the airway, the respirator can be taken off for instrumentation, or the detachable plastic plate (5) may be removed and replaced with a plate for oxygen delivery (13). After instrumentation, the respirator can be placed back on the patient, with the instrumenting device protruding through the slot created by detaching the detachable plastic plate (5). The additional filtering/sealing layers (11) can then be enclosed around the stem of the instrumenting device by pulling on the drawstrings. If necessary, the attached sealing/filtering layers around the edges of the respirator can then be unraveled and secured on the patient's face with the adhesive strip. After the procedure, the detachable plastic plate (5) could be re-attached, and the respirator can be used continually for round the clock protection.

In an alternative embodiment, the filtering facepiece respirator may be constructed for use on animals.

It is contemplated that the filtering facepiece respirator may also be used in any field where filtration protection is required around a smaller opening or access point.

In a further exemplary embodiment, the present disclosure provides a process for making a respirator including at least one of the following steps and combinations thereof.
1. Creating a mold of a filtration media (e.g., a standard N95 rated filtration media or a filtration media having any other filtration ratings). The mold provides a true positioning reference.
2. Creating a square unit made of medical grade plastic with the locations of 3 holes recessed.
3. Providing a punch process, to punch out the three recessed areas (catch slugs for recycling).
4. Creating a second mold with a $CO_2$ port recessed the length of valve.
5. Dropping a pre-assembled valve into the recessed zone.
6. Placing the unit in a mold, focusing on alignment at the $CO_2$ valve point.
7. Heating the plastic at the point of contact of the valve and unit to merge the 2 pieces into one unit.
8. Punching a square hole in all layers of the filtration media (e.g., N95 layer or material of any other filtration rating) for production of the mask.
9. Merging the complete unit with a support layer of the mask material (e.g., N95 layer or material of any other filtration rating) at the diameter overlap (stitch or adhesive).

10. Resuming standard production/assembly with polypropylene layers and filter layers (the layers having an N95 rating or any other filtration rating) and aligning the same.

The respirator disclosed herein may be made to fit other standards than N, including but not limited to R and P for oil resistant usage.

The respirator may be made as a non-filtering facepiece respirator that fits either the N, R, or P standard. A version of the respirator similar to a trach collar may be made for tracheostomy devices and venturi devices. Accordingly, the concepts and features discussed herein with respect to the filtering facepiece respirator may be incorporated into a trach collar device or a venturi mask. Parts of the respirator may be made with other materials. For example, the sealing layers maybe made with rubber other than silicone. The body of the respirator/filter media may be made with materials other than polypropylene and polyester, such as for example, without limitation, an electroceutical fabric.

In one embodiment, the respirator may be made without the clear plastic base that houses that oxygen and capnography connectors. The body of the respirator may be made, opaque, transparent or translucent. The nose clip may be made of material other than aluminum.

The silicone sleeve may be made of some other material like rubber, nylon etc. The sealing mechanism on the silicone sleeve may use techniques other than drawstrings, such as, for example without limitation, drawstrings with ribbons, twist ties, zip ties, or the like. The strings maybe made of aluminum, nylon or other materials.

In certain embodiments, the detachable plate (5) may be placed on other parts of the respirator, other than the base unit aperture (6) which is provided up front, where the mouth opens directly. The detachable plate (5) may be made without an exhalation valve. The base unit aperture (6) for the detachable plate (5), and the plate (5) itself, may be made of shapes other than circular or oval shapes. The detachable plate (5) may be attached/detached from the respirator using a connecting mechanism other than a male-to-female or snap-fit connection. The additional covered slot provided for oxygen/suction may be made detachable or not detachable, may be provided with or without an additional exhalation valve and may be placed on another part of the respirator. Devices that substitute the detachable plate (5) may be electronic, battery powered, and enabled with radio communication (for example, Bluetooth®).

The elastic bands that secure the mask to the patient's head may be made without the detachable/adjustable buttons. The elastic bands that secure the mask to the patient's head may be placed behind the ears instead. The enhanced sealing silicone layers may be prefabricated to be secured to the respirator.

In an exemplary embodiment, the respirator may be placed on a patient upon admission to the hospital and secured to the patient's head using the elastic bands. Prior to a procedure the elastic bands can be snapped off the respirator and placed to the side, and the patient's airway instrumented with a medical device. Upon instrumentation, the detachable plate (5) may be removed from the base unit aperture (6) and the compressed silicone sleeve (10) adhered to the clear plastic base (4) around the base unit aperture (6). The elastic bands (2) may then be snapped back on and adjusted for a better seal. The silicone sleeve (10) may then be expanded from its original collapsed state and sealed around the lumen of the medical device by pulling on the drawstrings. Also, the enhanced sealing silicone layer (11) may be adhered to the edges of the filter media (3) using the bottom adhesive strip and unraveled around the outer edges of the mask, around the patient's jaw/neck for an added seal. In certain embodiments, the edges of the body of the respirator may include extra polyester seals for providing an improved seal.

The respirator may also be pushed down to the patient's chin while still secured by the elastic bands.

Figure 18:
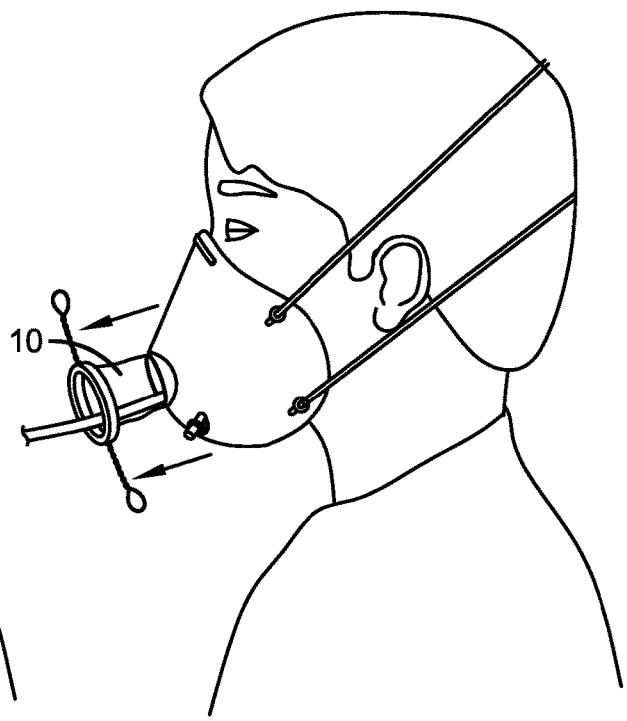
FIG. 18 is a side view of an exemplary embodiment of a filtering facepiece respirator.

Referring now to FIG. 18, alternatively, for procedures that require constant in and out movement of the medical device (such as, for example without limitation, an EGD or TEE scope, bronchoscope, or the like), the detachable plate (5) may be removed from the respirator while it is still secured to the patient's face. The silicone sleeve (10) may then be adhered to the body of the mask prior to insertion of the scope. After the scope is inserted, the sleeve can be expanded vertically, and tightened around the stem of the medical instrument using the drawstrings. The enhanced sealing silicone layer may then be adhered to the respirator and unraveled around the patient's jaw/neck and secured with the adhesive layer.

For spontaneously breathing patients, additional oxygen may be delivered by connecting some oxygen tubing (14) to the 90-degree adapter (12), opening the capped slot (7) and plugging in the adapter to the slot. Capnography could also be measured by connecting the capnography tubing (15) to the capnography luer lock (8) after taking off the cap.

Upon the completion of the procedure, the detachable plate (5), oxygen adapter (13), PEEP valve (17) or some other auxiliary device may be attached on to the aperture/base unit (6).

The patient may take the mask home upon discharge. Accessorizing devices such as, for example without limitation, templates, logos, flags, banners, hoods, hijabs or the like (24) may be attached to the respirator in the 4 holes on the front (see FIG. 1) via buttons or other forms of attachment.

A further embodiment of a filtering facepiece respirator (100) is provided in FIGS. 21-26. The filtering facepiece respirator (100) includes a mask body (102). The mask body (102) may be described as having an anterior portion, a posterior portion, a middle portion, a first side portion, a second side portion, a top side portion, a bottom side portion and outer edge portions. The mask body (102) may be made of a silicone and/or of a medical grade plastic material such as polypropylene, polycarbonate, nylon and/or any other medical grade plastic material deemed suitable to a person of ordinary skill in the art. In other embodiments, the mask body (102) may be made from a plasticized PVC or a similar material. In other embodiments, the mask body (102) may be designed to be transparent. This allows the practitioner to view the patient's face while the mask is worn. In other embodiments, the filtering facepiece respirator includes a transparent mask body (102) attached to an existing N95 or other filtration rated mask. In other embodiments, the mask body (102) may include filter media positioned at various parts of the mask (e.g., The mask body (102) is molded into a shape having contours which are designed to fit around a patient's facial features.

The molded contours of the mask body (102) may form a nose bridge (104) which allows the interior side of the mask body (102) to fit over a patient's nose. According to certain aspects of the present teaching, the nose bridge (104) may include a nose clip secured to the mask body. The nose clip may be made from a metal such as aluminum or any other suitable metal or material known to a person of ordinary skill in the art.

The outer edge portions of the mask body (102) may include one or more fasteners (106) for securing one or more bands to the facepiece respirator (100). According to certain aspects of the present teaching, the fasteners are positioned along the outer edge portions of the mask body (102) adjacent to the first side portion and the second side portion of the mask body (102). This allows the band or bands to be attached to the first side portion and to the second side portion of the mask body (102). The band or bands may be adjustable according to certain aspects of the present teaching. The band or bands may be elastic according to further aspects of the present teaching. However, it is to be understood that the any type of band may be used which is suitable for securing the facepiece respirator (100) to a patient's head. It is to be further understood that any type of fastener may be used to secure the band or bands to the facepiece respirator (100). Examples of fasteners which may be used include but are not limited to a clip which attaches the band to a facepiece respirator (100), a port through which a band passes through attaching the band to the facepiece respirator (100), an adhesive which attaches the band to the facepiece respirator (100). As shown in FIG. 25, in one exemplary embodiment the fastener used is a clip (106) which includes a port or opening through which the band passes through. Under the clip is a flange at the edge portion of the mask body (102) which includes a port (not shown) through which the band passes through. In this case, the embodiment shown in FIG. 25 includes band fasteners at the top first side portion of the mask body (102), and the top second side portion of the mask body (102), at the bottom first side portion of the mask body (102) and at the bottom second side portion of the mask body (102).

Figure 16:
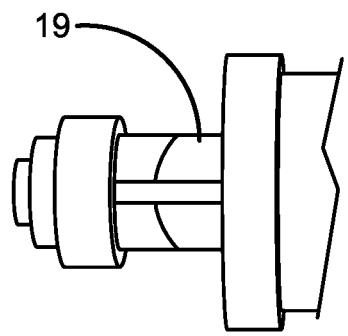
FIG. 16 is a side view of an exemplary embodiment of a filtering facepiece respirator.
Figure 21:
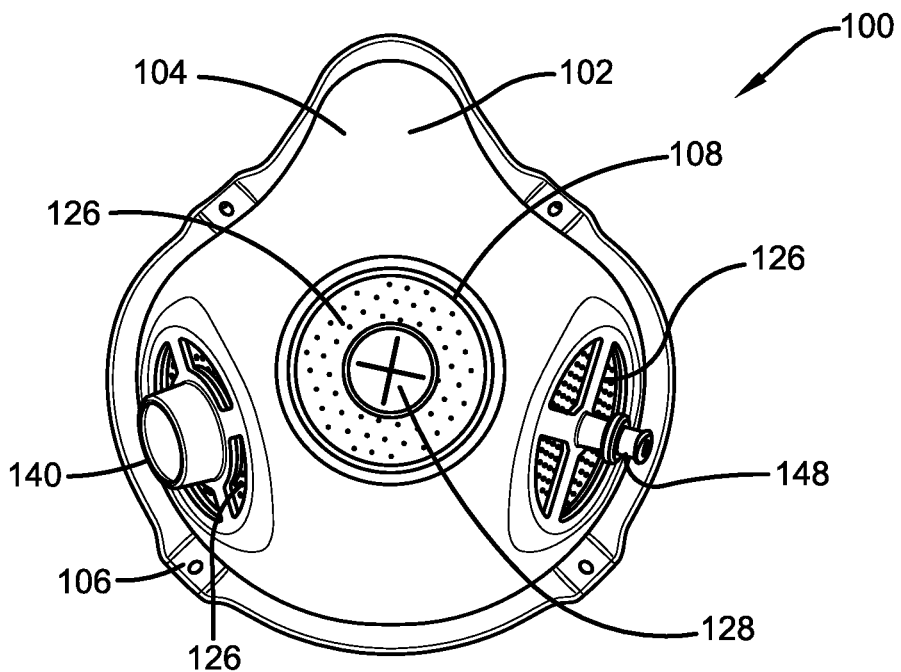
FIG. 21 is a front view of an exemplary embodiment of a filtering facepiece respirator.
Figure 22:
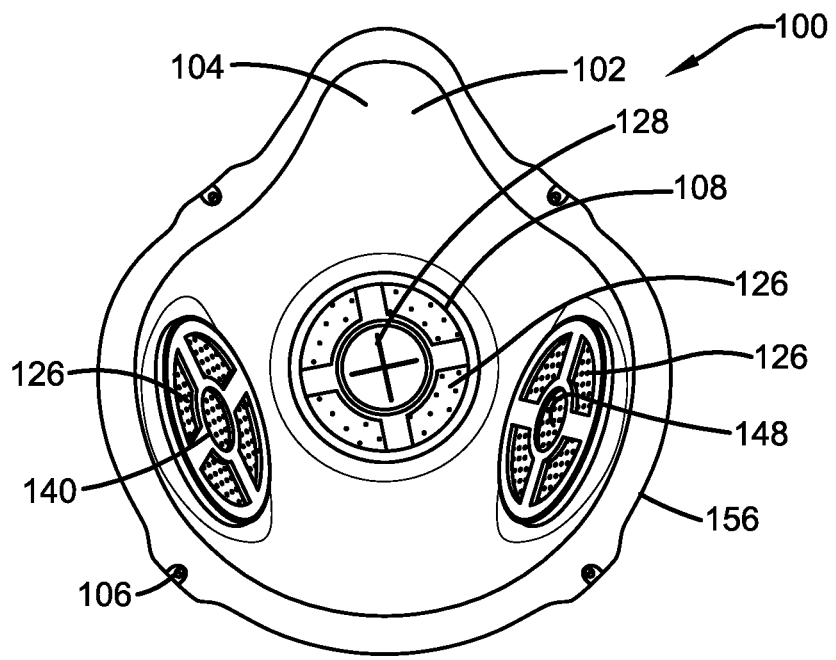
FIG. 22 is a back view of an exemplary embodiment of a filtering facepiece respirator.
Figure 23C:
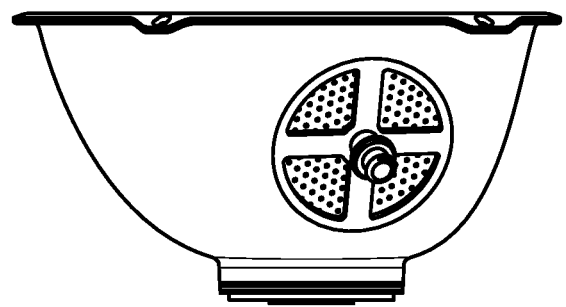
FIGS. 23A through 23D are respectively, a first side view, a top view, a second side view and a bottom view of an exemplary embodiment of a filtering facepiece respirator.
Figure 23B:
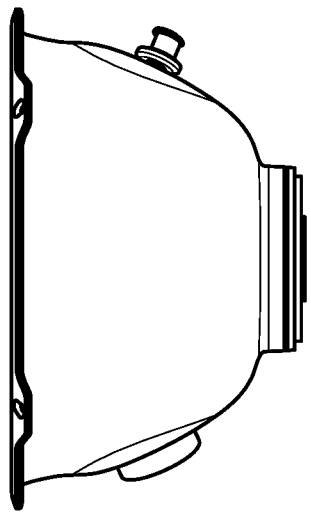
Figure 23D:
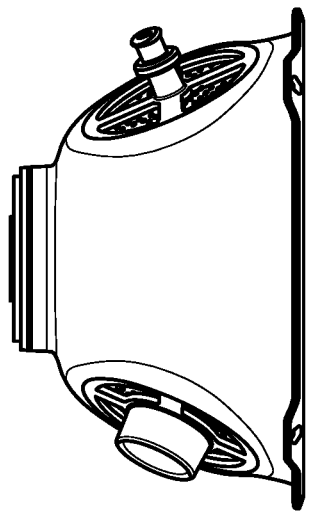
Figure 23A:
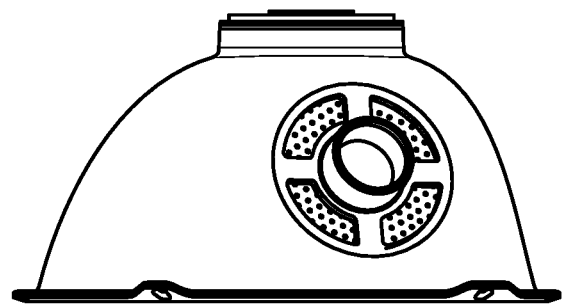
Figure 26C:
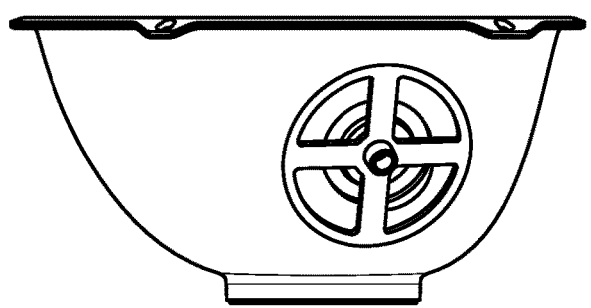
FIGS. 26A through 26D are respectively, a first side view, a top view, a second side view and a bottom view of a base mask of an exemplary embodiment of a filtering facepiece respirator.
Figure 26B:
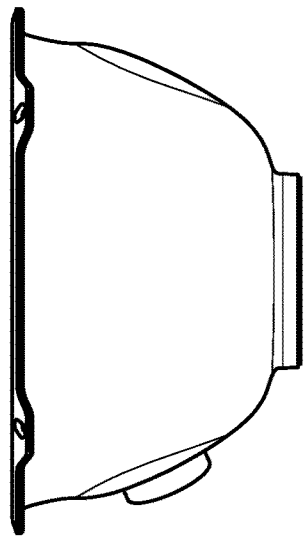
Figure 26D:
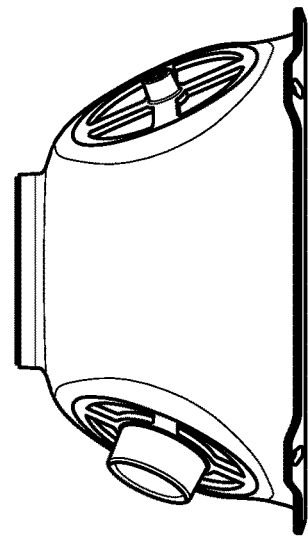
Figure 26A:
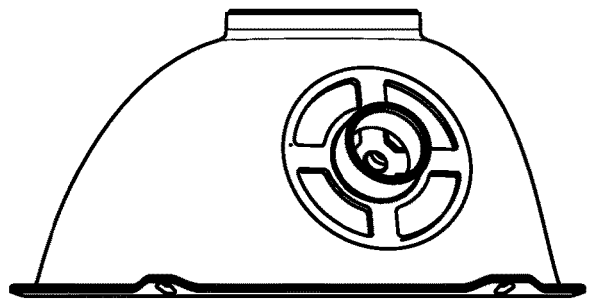
Figure 27:
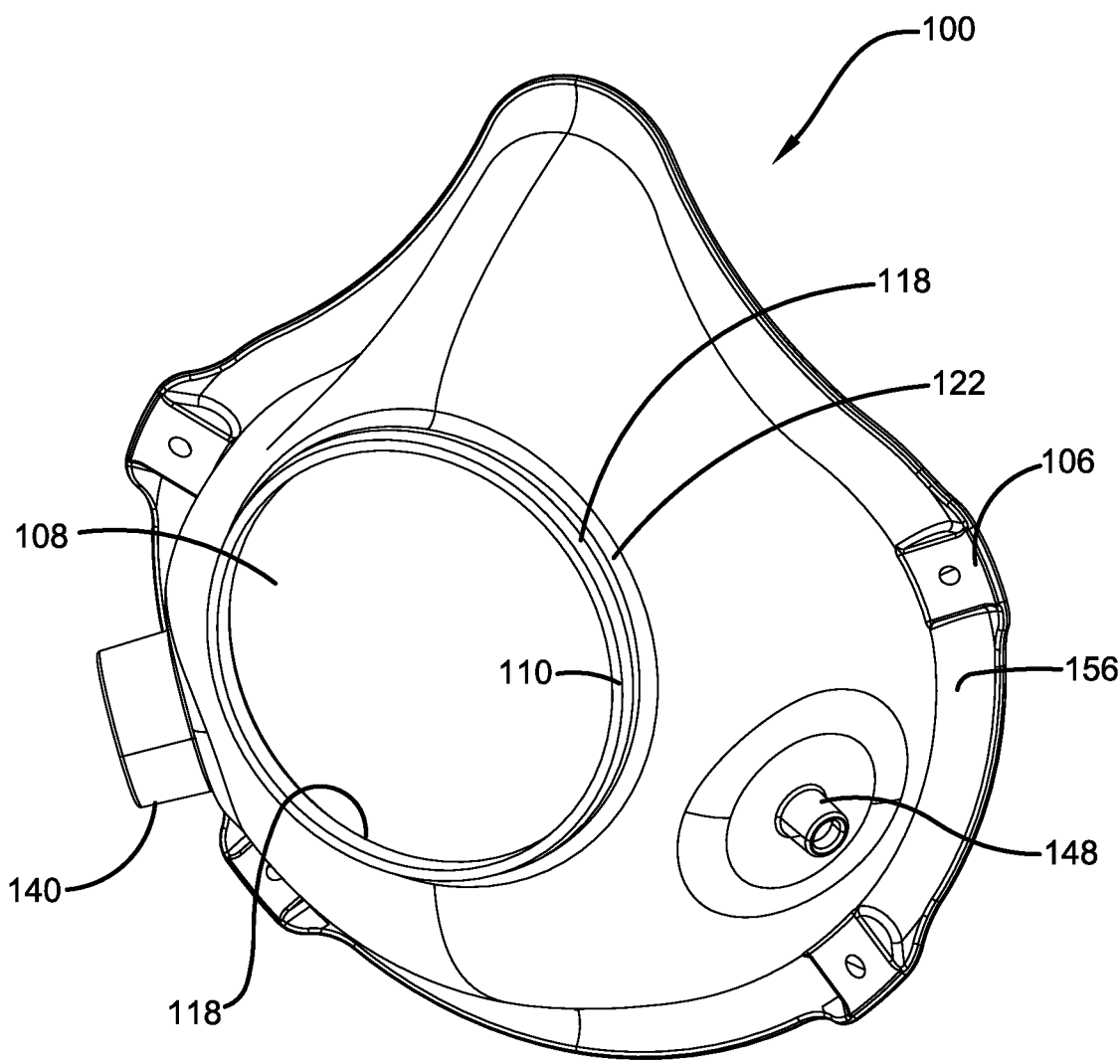
FIG. 27 is a front perspective view of an exemplary embodiment of a filtering facepiece respirator.
Figure 28:
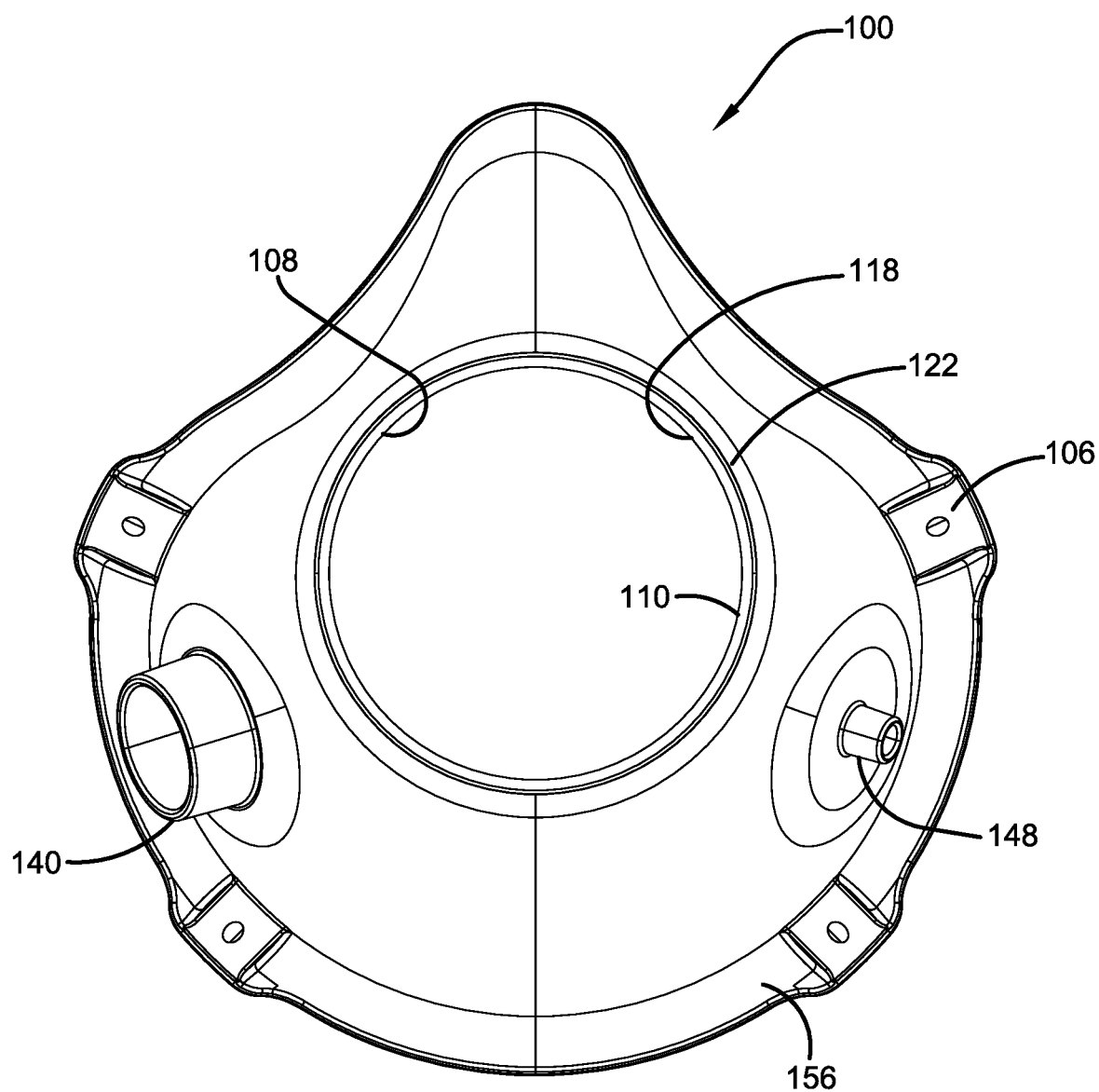
FIG. 28 is a front view of an exemplary embodiment of a filtering facepiece respirator.
Figure 29:
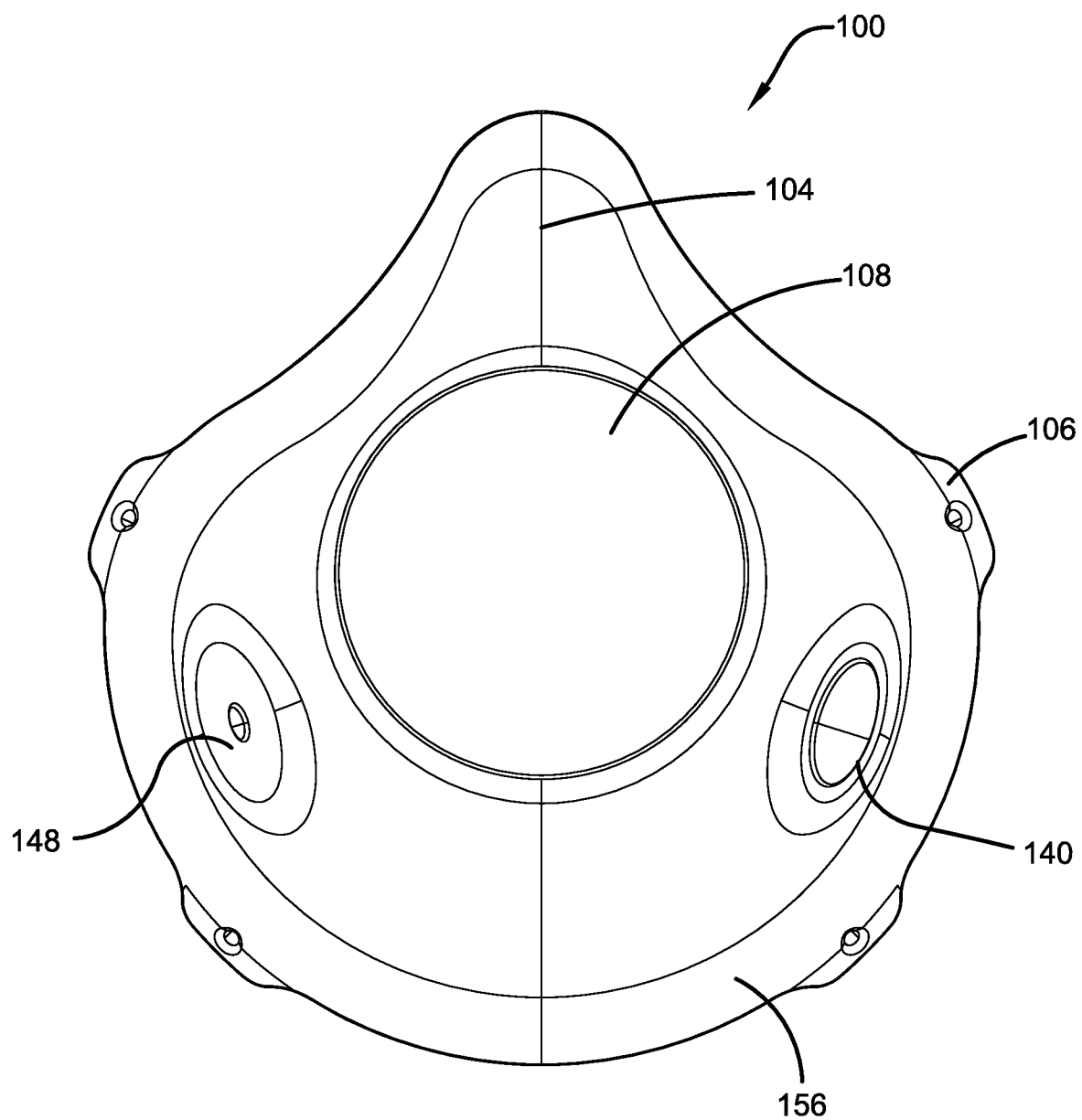
FIG. 29 is a back view of an exemplary embodiment of a filtering facepiece respirator.
Figure 30:
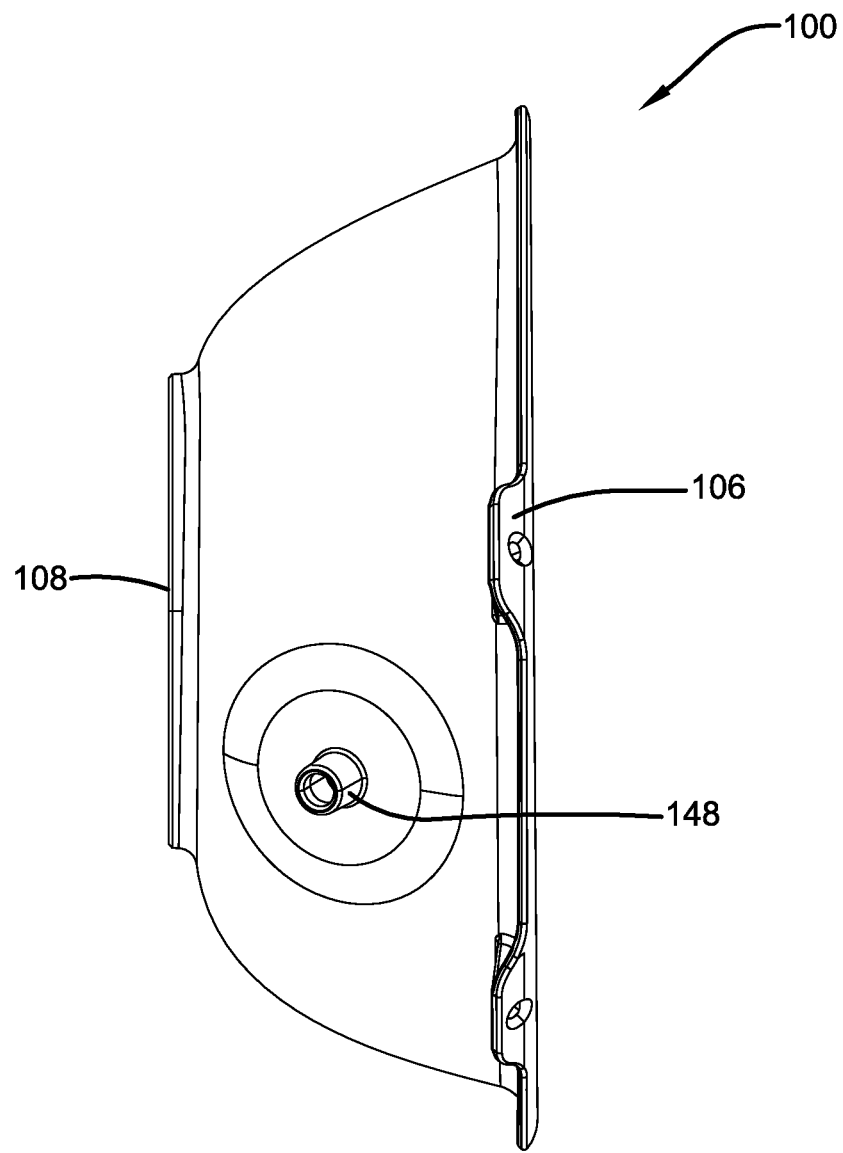
FIG. 30 is a side view of an exemplary embodiment of a filtering facepiece respirator.
Figure 31:
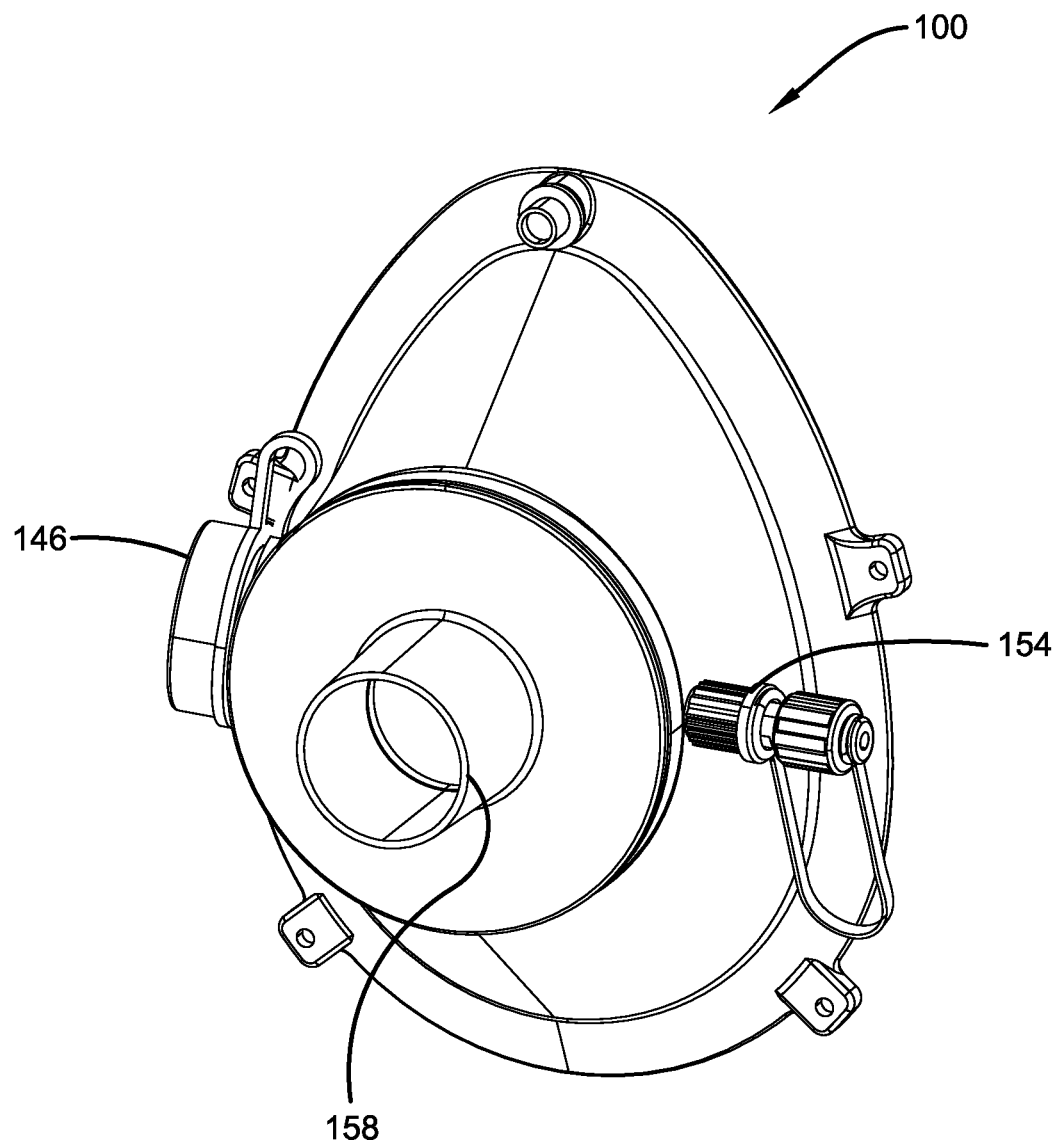
FIG. 31 is a front perspective view of an exemplary embodiment of a filtering facepiece respirator.
Figure 32:
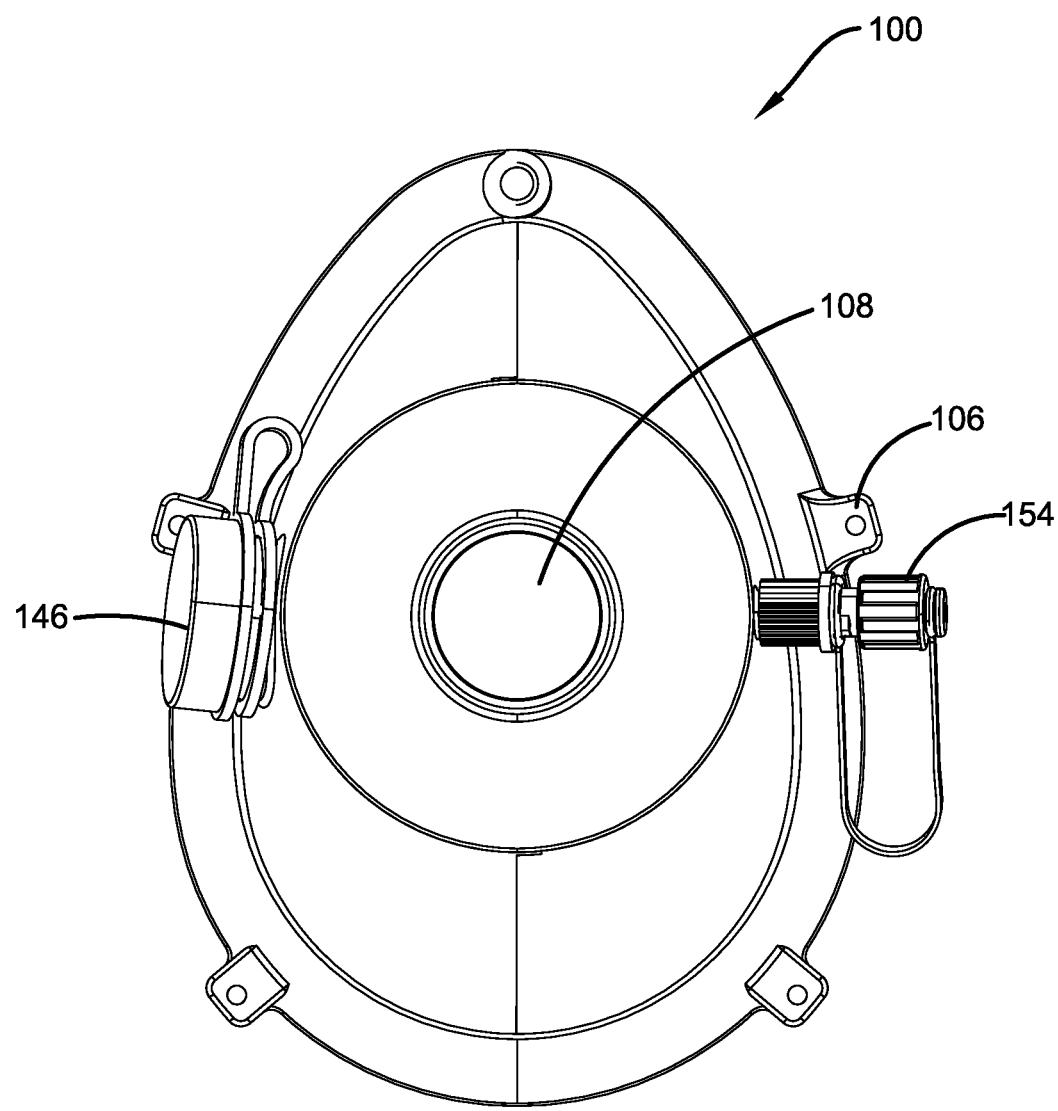
FIG. 32 is a front view of an exemplary embodiment of a filtering facepiece respirator.
Figure 33:
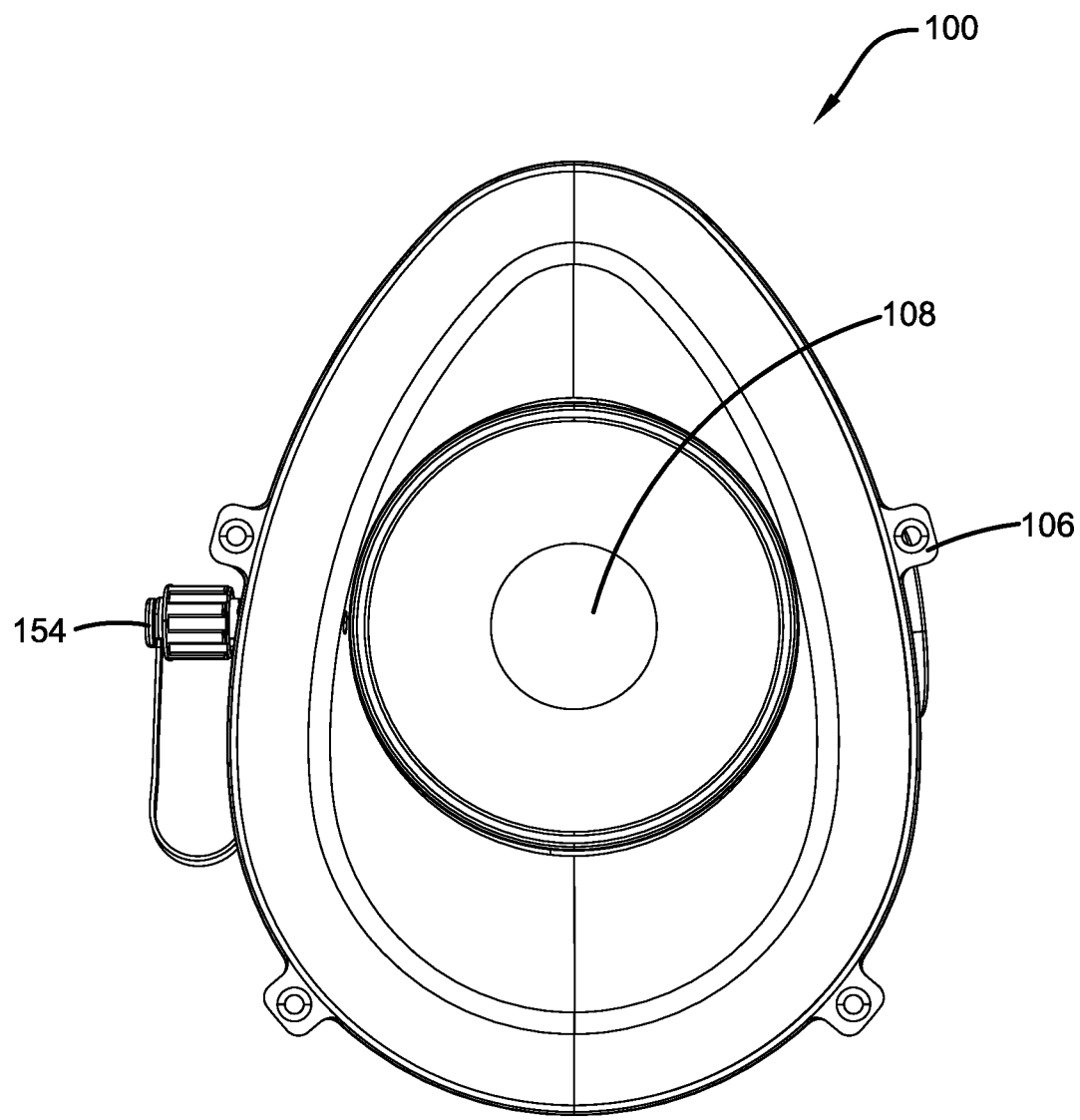
FIG. 33 is a back view of an exemplary embodiment of a filtering facepiece respirator.
Figure 34:
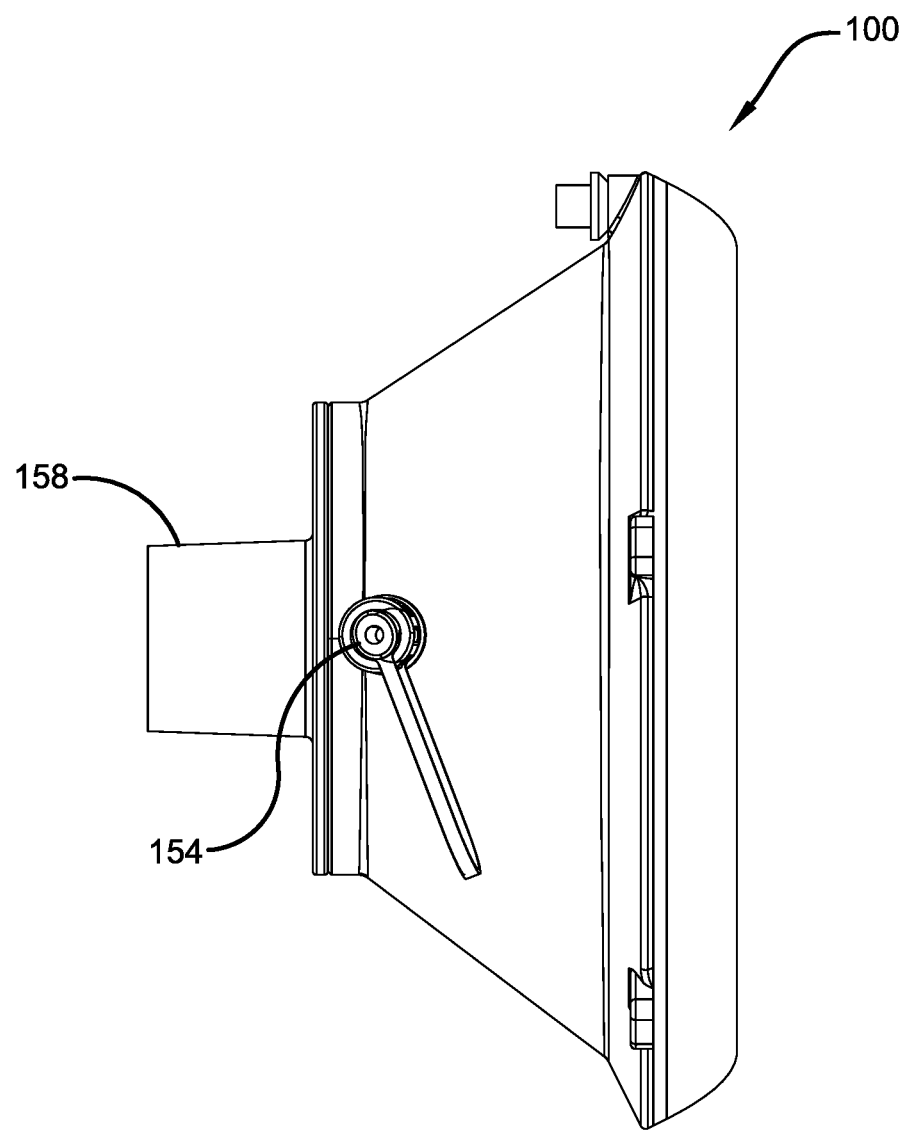
FIG. 34 is a side view of an exemplary embodiment of a filtering facepiece respirator.
Figure 36A:
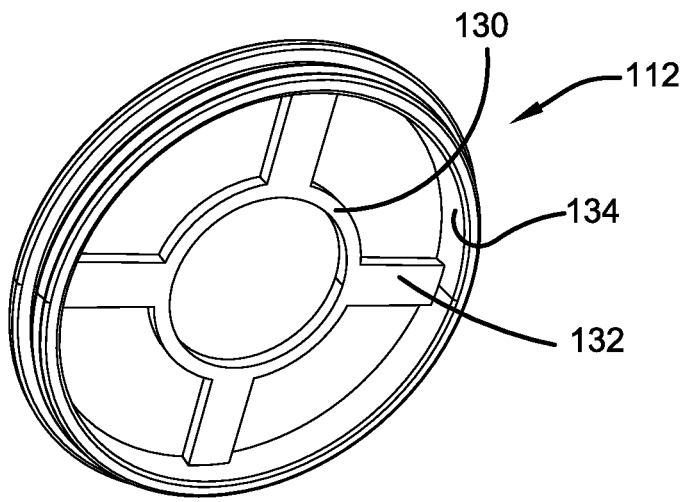
FIGS. 36A through 36D are respectively, a perspective view, a top or bottom view, a side view and a front view of an exemplary adapter for an exemplary embodiment of a filtering facepiece respirator.
Figure 36B:
Figure 36C:
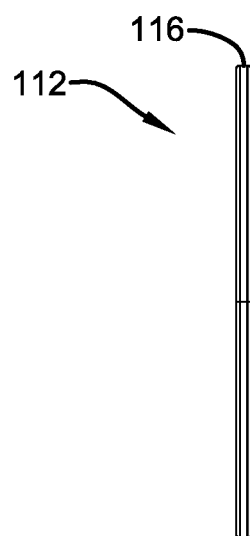
Figure 36D:
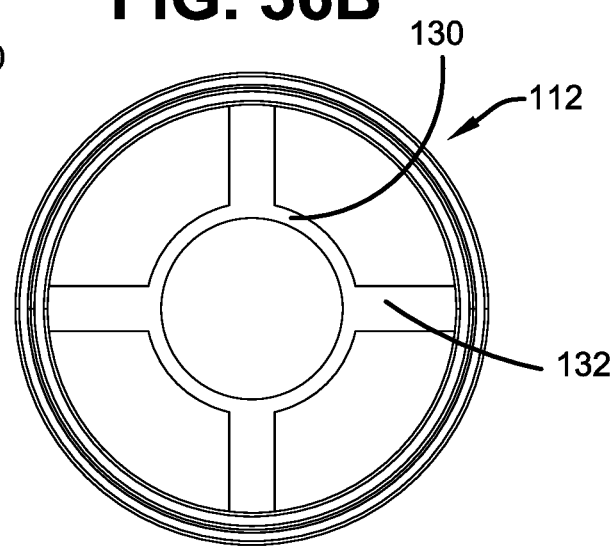
Figure 38C:
FIGS. 38A through 38E are respectively, a front view, a first side view, a top view, a second side view and a bottom view of an exemplary adapter for an exemplary embodiment of a filtering facepiece respirator.
Figure 38B:
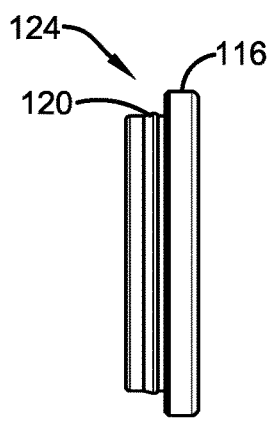
Figure 38A:
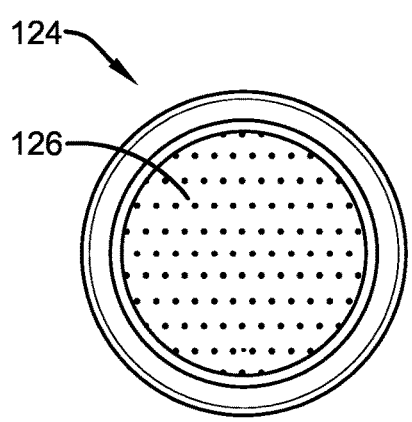
Figure 38D:
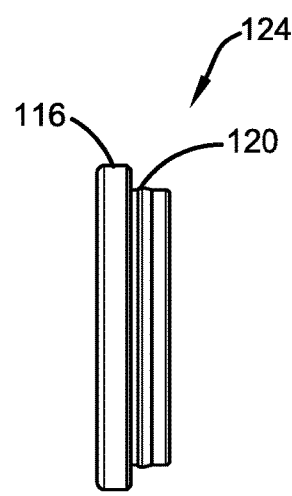
Figure 38E:
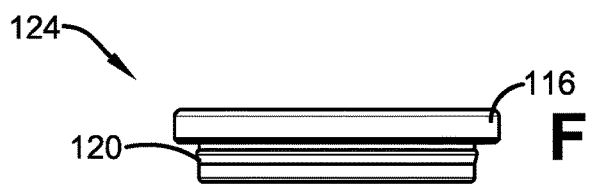
Figure 39:
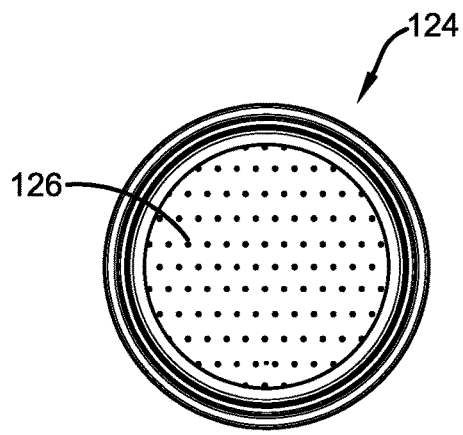
FIG. 39 is a back view of the exemplary adapter of FIGS. 38A through 38E.
Figure 42C:
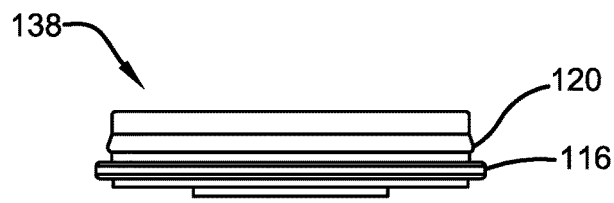
FIGS. 42A through 42E are respectively, a front view, a first side view, a top view, a second side view and a bottom view of an exemplary adapter for an exemplary embodiment of a filtering facepiece respirator.
Figure 42B:
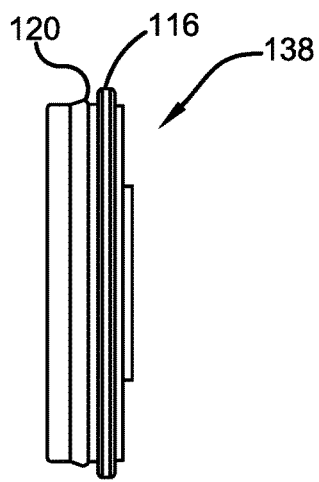
Figure 42A:
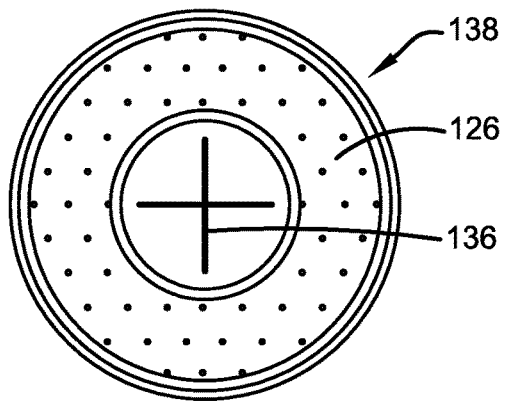
Figure 42D:
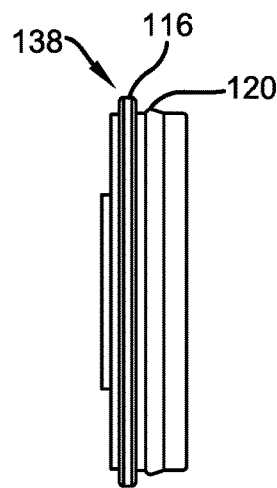
Figure 42E:

The mask body (102) further includes a primary port (108). The primary port (108) is positioned within the middle portion of the mask body (102). In certain embodiments as shown in FIGS. 21-16, the primary port is circular in shape although the primary port (108) may be any shape. The primary port (108) is designed to engage an adapter which may be referred to as a primary port adapter (158). The engagement of the adapter to the primary port is achieved through a press fitting and may be accomplished through a male and female connection between the primary port adapter (158) and the primary port (108). The press fitting may be accomplished by a snap fitting. In certain embodiments the primary port (108) may include ribs or flanges (110) along the circumference of the port (108). The rib or flange may provide a press-fitting along the circumference of the body of the primary port adapter (158). In other embodiments, the primary port (108) may include rib or flange (110) along its circumference and a recessed portion (118) along the circumference of the primary port (108) adjacent the rib or flange (110) which extends into the mask body (102). The recessed portion may engage a rib or flange (114) positioned along the circumference of a corresponding primary port adapter (158) when the adapter is engaged with the primary port (108), thereby providing a press fitting and seal between the primary port (108) and the primary port adapter. In other embodiments, the primary port (108) may include screw threads which engage corresponding threads of the primary port adapter, thereby providing a seal between the primary port (108) and the primary port adapter (158).

According to certain aspects of the present teaching, the primary port adapter (158) is a cap assembly (112) in the shape of a circular conduit or tubular structure and having a first end and a second end. In certain embodiments, the cap assembly (112) may include a flange or rib around its outer circumference for engaging a recessed portion (118) within the primary port (108). In other embodiments, the cap assembly (112) may further include a flange or rib (114) around its outer circumference for preventing the cap assembly (112) from falling through the primary port (108). In further embodiments, the cap assembly (112) may include a first flange or rib (116) around its outer circumference for engaging a recessed portion (118) within the primary port (108) and a second flange or rib (120) around its outer circumference for preventing the cap assembly (112) from falling through the primary port (108). According to further aspects of the present teaching, the primary port adapter (158) may include a first flange (115) or rib and a second flange or rib (120) around its outer circumference which function together as a snap coupling mechanism with respect to the primary port (108). Between the first flange or rib (116) and the second flange or rib (120) of the cap assembly (112) is a receiving space which receives a corresponding rib or flange (110 or 122) of the primary port (108). The first rib or flange (116) of the snap coupling mechanism of the cap assembly (112) may be tapered with respect to the outside surface of the conduit of the cap assembly (112) forming a gradual incline from the outside surface of the conduit to a peak forming an outer ridge along the circumference of the conduit of the cap assembly (112). The gradual include of the tapered portion of the rib or flange (116) of the snap coupling mechanism allows the cap assembly (112) to be easily inserted within the primary port (108) as it contacts the corresponding flange or rib (110 or 122) on the primary port (108) when inserted within the primary port (108). The highest point of the tapered portion with respect to the outer circumference of the conduit of the cap assembly (112) (i.e., the ridge) provides a snap connection, securing the cap assembly (112) to the primary port (108). With the flange or rib (110 or 122) of the primary port (108) positioned within the receiving space of the cap assembly (112), the combination of the ridge (the first flange or rib) (116) and the second flange or rib (120) of the cap assembly (112) on opposing sides of the receiving space prevents the cap assembly (112) from being easily being removed or falling through the primary port (108). In another embodiment, one of the first end or second end of the cap assembly (112) includes screw threads for engaging corresponding threads on the primary port (108). This allows the cap assembly (112) to be screwed into the primary port (108) of the filtering facepiece respirator (100), thereby providing a seal between the primary port (108) and the primary port adapter (158) or cap assembly (112). The primary port (108) may receive a variety of different types of primary port adapters and cap assemblies.

Also provided is a filtering facepiece respirator which provides positive pressure ventilation when a patient is not breathing. The respirator has the same functionality and ports of other embodiments. The mask may have a transparent mask body (102) made from a clear plastic such as polycarbonate or a similar plastic material overmolded on a silicone (or similar rubber-like base) that fits around a patient's face in a cuff-like manner. In certain embodiments, the base or rubber-like base is inflatable allowing for an improved seal and improved comfort. An example of such a respirator is illustrated within FIGS. 31-34. As illustrated within FIGS. 31-34, the respirator 100 includes a primary port adapter or cap (158) on the primary port, an oxygen port adapter or cap (146) on the oxygen port and a luer port adapter or cap (154) on the luer port. The primary port adapter/cap (158), oxygen port adapter/cap (146) and luer port adapter/cap (154) may be filtered or non-filtered and may include any one of the cap assemblies disclosed herein. In certain embodiments, the primary port adapter (158) converts the primary port to a smaller sized port such as a standard 22 mm sized port. In other embodiments, the primary port adapter (158) converts the primary port to a 15 mm sized port. Both 22 mm and 15 mm sized ports are standards in the industry of anesthesia and respiratory care, are used worldwide and are capable of engaging numerous accessories. The oxygen port adapter (146) and luer port adapter (146) has a similar effect on the oxygen port and luer port converting a much larger sized port to a smaller sized port (e.g., a 22 mm or 15 mm port) capable of engaging numerous accessories. The primary port adapter/cap (158), oxygen port adapter/cap (146) and luer port adapter/cap (154) shown in FIGS. 31-34 and 59 fit are capable of engaging corresponding ports and are interchangeable with other respirator embodiments disclosed herein. In a further embodiment, the respirator (100) may include an optional air port (160) at the top of the apex of the base of the mask. This port would be used to inflate a base (162) (e.g., a rubber or rubber-like base).

The present disclosure contemplates the use of three different types of cap assemblies (112) used with the primary port (108), oxygen port (140) and luer port (148) of the filtering facepiece respirator (100). The first cap assembly (112) is a filtered cap assembly (124). The filtered cap assembly (124) includes a filter membrane (126) positioned within the conduit and attached to the inside surface of the conduit of the cap assembly (112) (i.e., perpendicular with respect to the inside surface of the conduit of the cap assembly). The filter membrane (126) may be described as having a proximal end and a distal end with respect to the anterior portion of the mask body (102). According to further aspects of the present teaching, the filter membrane (126) may include a slit cut into the filter membrane forming a slit port (128). In some embodiments, the slit port (128) may be a cross slit. The slit or cross slit allows for medical personnel to insert an instrument through the filter membrane (126) towards the posterior side of the mask body (102) and into the patient's buccal cavity. According to certain aspects of the present teaching, the filtered cap assembly (124) includes a frame (not shown) positioned on the posterior portion of the mask body (102). The frame provides structural support to the filtered membrane and assists in securing the filtered membrane to the inner circumference of the conduit of the cap assembly. In certain embodiments, the frame may include a circular portion (130) which attaches to the posterior side of the filtered membrane and a suitable number of frame extensions (132) which extend from the circular portion (130) and attach to the inner surface (134) of the conduit of the cap assembly (112).

A second cap assembly (112) provided herein is a slit port cap assembly. The slit port cap assembly does not include a filter membrane but rather, includes a self-sealing slit port (e.g., a cross slit port) which allows for medical personnel to insert an instrument through the slit port (128) towards the posterior side of the mask body (102) and into the patient's buccal cavity. The self-sealing slit port (136) of the slit port cap assembly is made from a self-sealing silicone material which is capable of forming a seal around an instrument which is passed through the slit port (128). However, the self-sealing material may also be made from any type of self-sealing material (i.e., from materials other than silicone) including but not limited to polymeric materials. The slit port cap assembly includes a self-sealing slit port membrane (136) positioned within the conduit and attached to the inside surface of the conduit of the cap assembly (112) (i.e., perpendicular with respect to the inside surface of the conduit of the cap assembly). The self-sealing slit port (136) may be described as having a proximal end and a distal end with respect to the anterior portion of the mask body (102). According to certain aspects of the present teaching, the slit port cap assembly includes a frame (not shown) positioned on the posterior portion of the mask body. The frame provides structural support to the self-sealing slit port membrane and assists in securing the self-sealing slit port membrane to the inner circumference of the conduit of the cap assembly. In certain embodiments, the frame may include a circular portion (130) which attaches to the posterior side of the self-sealing slit port (136) and a suitable number of frame extensions (132) which extend from the circular portion (130) and attach to the inner surface (134) of the conduit of the cap assembly.

Figure 43:
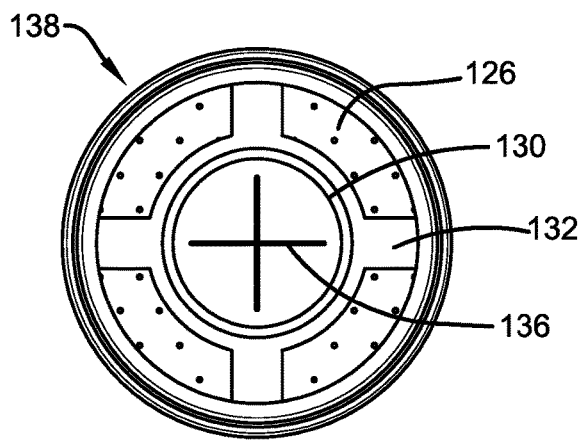
FIG. 43 is a back view of the exemplary adapter of FIGS. 42A through 42E.
Figure 46:
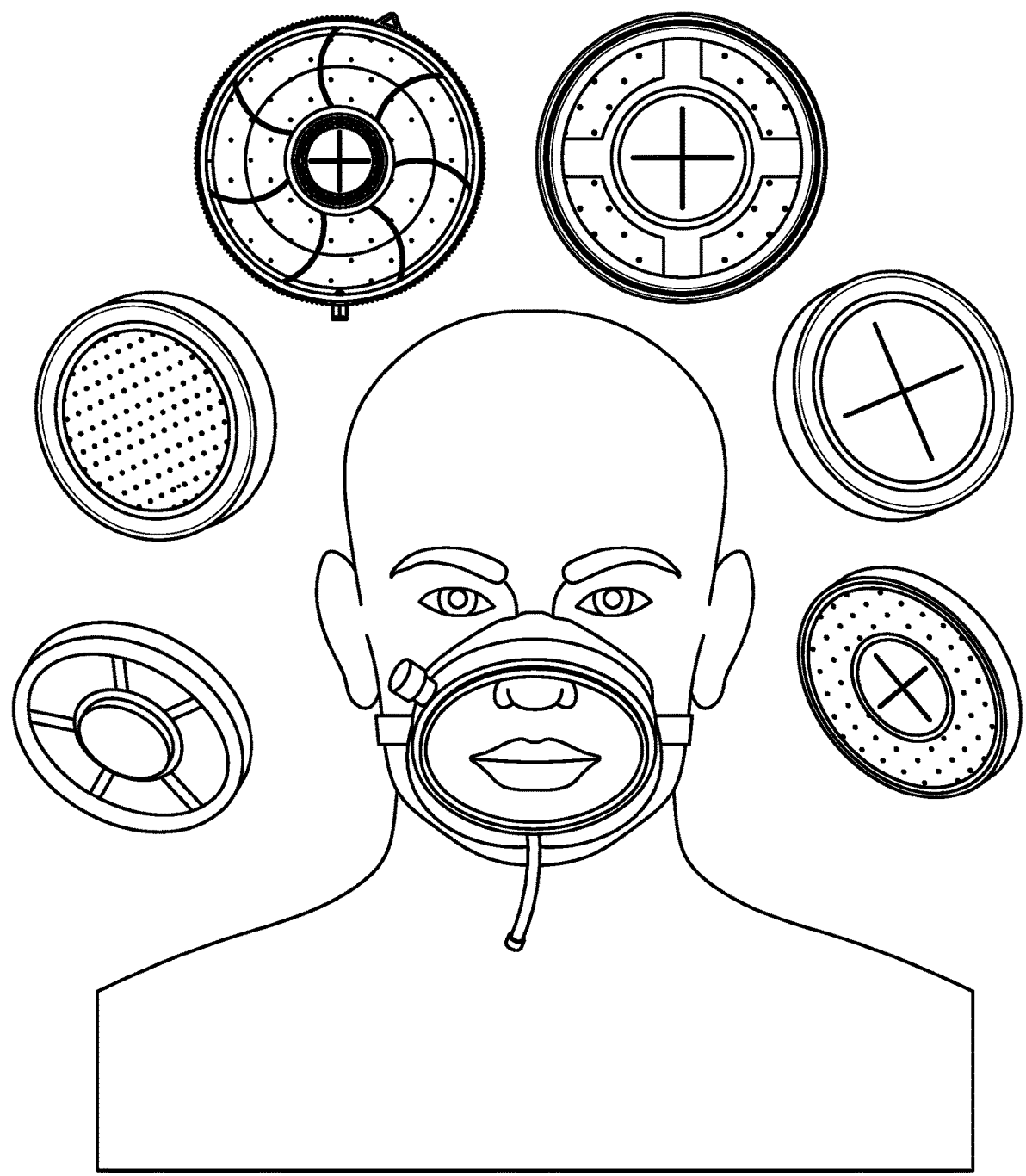
FIG. 46 is an exemplary embodiment of a filtering facepiece respirator illustrating the various adapters or cap assemblies that may engage the front of the mask.
Figure 61:
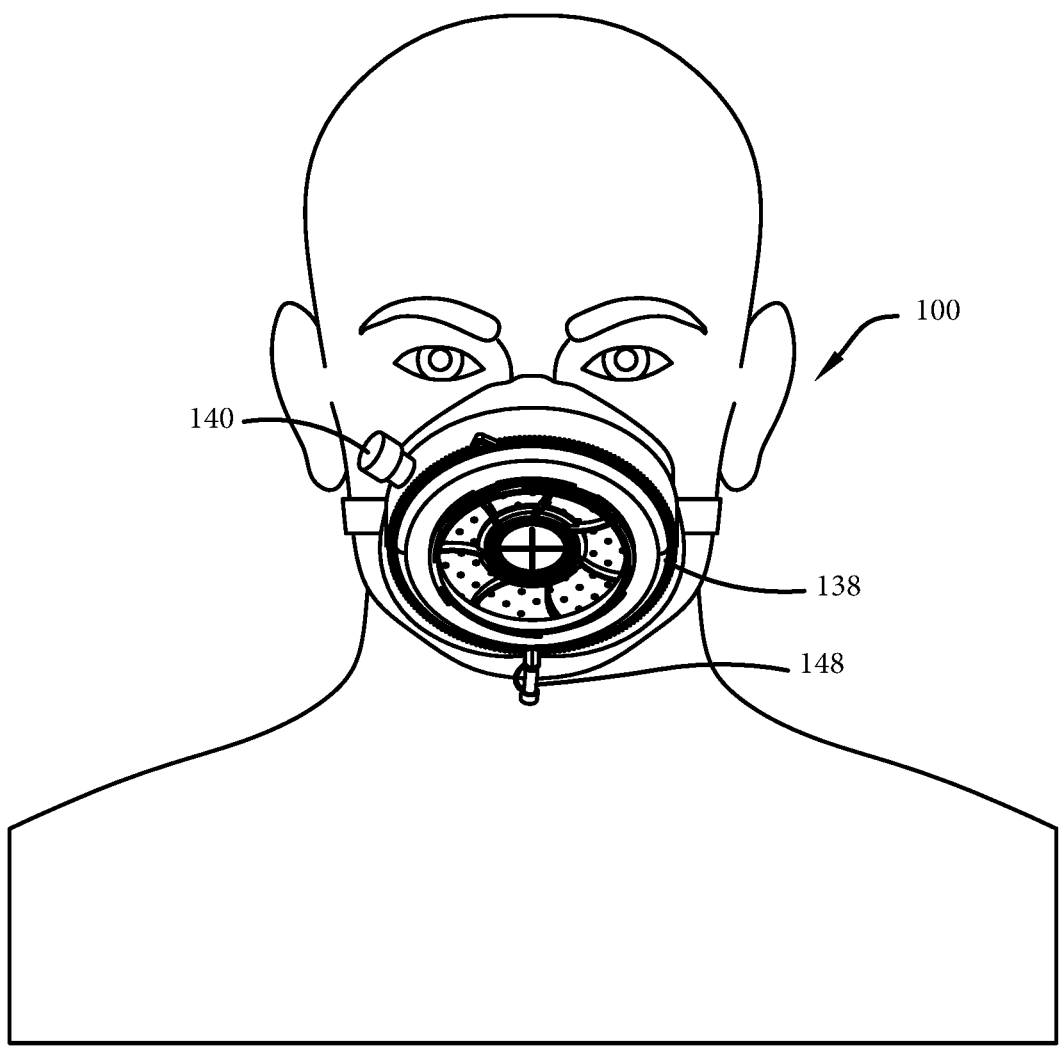
FIG. 61 is an exemplary embodiment of a filtering facepiece respirator including an adapter or cap assembly having a fin-shaped frame.

A third cap assembly provided herein is a filtered slit port cap assembly (138). The filtered slit port cap assembly (138) includes a self-sealing slit port (136) (e.g., a cross slit port) surrounded by a filter membrane (126). The self-sealing slit port (136) allows for medical personnel to insert an instrument through the slit port (128) towards the posterior side of the mask body (102) and into the patient's buccal cavity. The self-sealing slit port (136) of the filtered slit port cap assembly (138) is made from a self-sealing silicone material which is capable of forming a seal around an instrument which is passed through the slit port (128). However, the self-sealing material may also be made from any type of self-sealing material (i.e., from materials other than silicone) including but not limited to polymeric materials. The self-sealing slit port (136) is positioned within the conduit of the cap assembly (112) and has a diameter that is less than the diameter of the cap assembly (112). The circumference of the self-sealing slit port (136) is surrounded by and attached to the filter membrane (126). The filter membrane (126) is in turn secured and attached to the inner circumference (134) of the conduit of the cap assembly. Thus, the filter membrane (126) and self-sealing slit port (136) are positioned within the conduit and attached to the inside surface of the conduit of the cap assembly (112) (i.e., perpendicular with respect to the inside surface of the conduit of the cap assembly). The filter membrane (126) and self-sealing slit port (136) may be described as having a proximal end and a distal end with respect to the anterior portion of the mask body (102). According to certain aspects of the present teaching, the filtered slit port cap assembly (138) includes a filter frame positioned on the posterior portion of the mask body. The filter frame provides support to the filter membrane (128) and assists in securing the filter frame to the inner circumference (134) of the conduit of the cap assembly (112) and to the outer circumference of the self-sealing slit port (136). An example of a filter frame is shown in FIGS. 35, 36 and 43. In certain embodiments, the filter frame may include a circular portion (130) which attaches to the self-sealing slit port (136) and frame extensions (132) which extend from the circular portion (130) and attach to the inner surface (134) of the conduit of the cap assembly (112). The filter frame shown in FIGS. 35, 36 and 43 includes four frame extensions. However, any suitable number of frame extensions may be utilized. In a further embodiment, the filtered slit port cap assembly may include a frame that may be described as being fin-shaped or having turbine shaped spokes. This frame is designed to provide support for the filter membrane or filter media in a way that minimizes obstruction of air flow. This is accomplished by arranging the frame in a blade-like manner that fans out anteriorly rather than laterally. This results in a more aerodynamic cap design. Examples of a filtered slit port cap assembly having a fin-shaped frame is illustrated in FIGS. 60A, 60B, 60C, 60D, and 60E. The filter media or filter membrane is bonded to the inner diameter at the inner edges of the cap assembly. The primary embodiment of this type of cap assembly is one without any frame members in the center portion of the cap assembly. In this embodiment, the center portion of the cap assembly would include a seal (e.g., an elastomeric seal) having a slit. Examples of this embodiment are illustrated in FIGS. 46 and 61. In another embodiment, the fin-like frame members may extend into the center portion of the cap assembly and the center portion of the cap assembly would not include a seal. This embodiment contemplates a variation of the filtered cap assembly mentioned above.

Figure 62A:
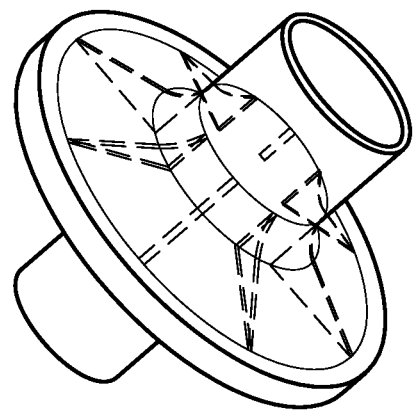
FIGS. 62A, 62B and 62C are an internal perspective view, a perspective view and a cross-sectional view of an exemplary embodiment of a viral filter which may be inserted through the slit of the seal of an adapter or cap assembly of a filtering facepiece respirator.
Figure 62B:
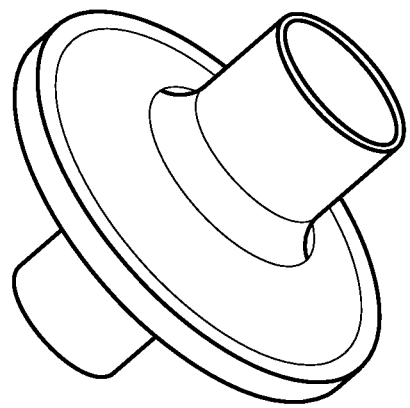
Figure 62C:
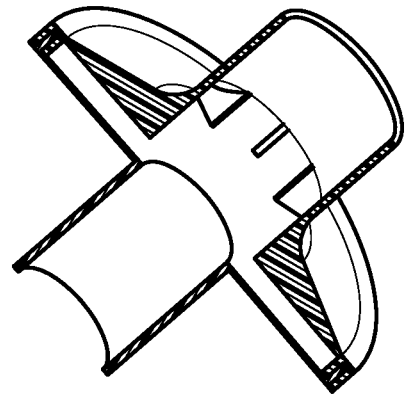

FIGS. 62A and 62B illustrate a viral filter which may be used in conjunction with a cap assembly having a seal (e.g., an elastomeric seal) with a slit port. The viral filter is inserted through the slit into the seal. The viral filter includes an air passageway that allows a patient to breathe through the viral filter. In use, a patient may use a filtering facepiece respirator that is fitted with a breathing device. After the breathing device is removed, a cap assembly having a seal and a slit port is fitted onto the filtering facepiece respirator. The viral filter is then inserted into the slit port in the cap assembly. The patient breathes through the viral filter inserted through the seal. This provides a safe environment for the patient to breath, for example, in situations where the patient is, or others are vulnerable such as when a patient is being transported after an operation to the recovery room. Once the viral filter is inserted, the seal motions back and forth as the patient breathes. In this way, the seal acts as a breathing indicator while the patient is being transported. The use of the viral filter is intended to be temporary until a filtered cap assembly (i.e., a cap assembly without a seal and a slit) is attached to the filtering facepiece respirator. As shown tin FIG. 62A, the viral filter may include a circular portion having an interior portion positioned around the circumference of a tubular portion. The interior portion of the circular portion may include ribs or support structures which are angled and extend upwards to the tubular portion.

Figure 58:
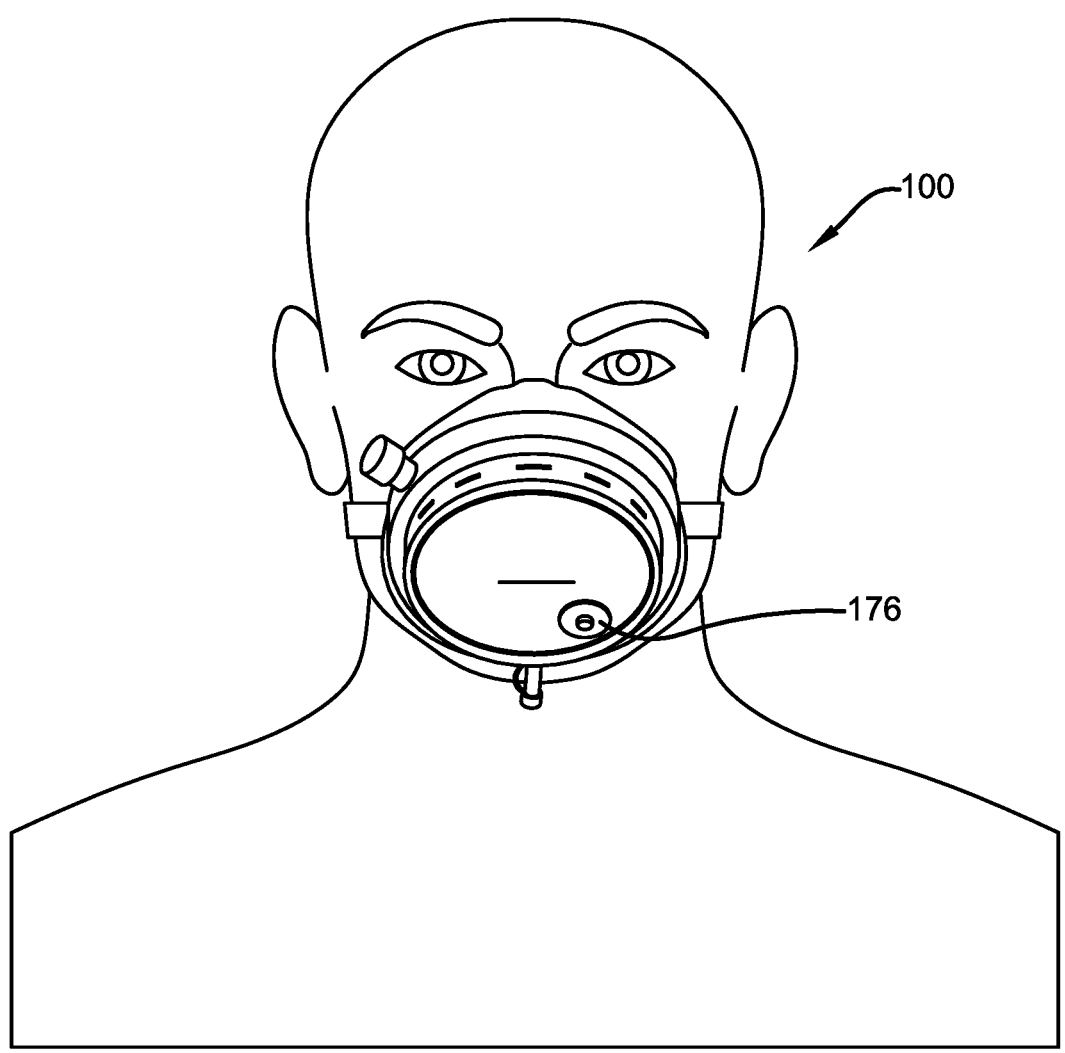
FIG. 58 is an exemplary embodiment of a filtering facepiece respirator illustrating an exhalation valve incorporated into a silicone seal of the respirator.

The cap assemblies described above, and cap assemblies further contemplated in this disclosure may further include an exhalation valve (not shown) allowing for air exhaled by a patent to exit the enclosed space created by the posterior portion or side of the filtering facepiece ventilator and the patient's face. The exhalation valve (176) may be positioned within the filter membrane or self-sealing slit of the cap assembly (e.g., as shown in FIG. 58). In further embodiments, the exhalation valve (176) may be positioned within the mask body separate from the cap assembly (e.g., as shown in FIG. 24B).

In addition to the cap assemblies described above, the primary port (108) is also capable of engaging any one of the following primary port adapters: an adapter for oxygen delivery, an adapter for nebulized medications/substances; an adapter for a PEEP valve attachment, an adapter for a device for taking breath samples with vacuum tubes, an adapter for an electronic device for measurement of spirometry/$CO_2$/temperature, an adapter for a humidifying and/or vaporizing device; an adapter for an electronic breathalyzer device, an adapter for an electronic nicotine delivery system, and an adapter for a UV light device.

As mentioned above, the filtering facepiece respirator (100) may further include an oxygen port (140) positioned on a first anterior side portion or a second anterior side portion of the mask body (102). The oxygen port (140) is formed from a cut-out within the mask body (102) which provides an aperture from the anterior portion of mask body (102) to the posterior portion of the mask body (102). Typically, the cut-out which forms the oxygen port (140) is circular although any shape cut-out may be formed within the mask body for the oxygen port (140). This circular cut-out may be referred to as the outer aperture of the oxygen port (142). According to certain aspects of the present teaching, the aperture which forms the oxygen port (140) may further include a frame. The frame may include a circular portion (130) having a diameter which is less than the diameter of the outer aperture (142) of the oxygen port (140). The circular portion (130) of the frame may also include an inner aperture (144) allowing for insertion of an oxygen port adapter (146) within the inner aperture (144) of the oxygen port (140). The frame may further include a suitable number of frame extensions (132) which extend from the circular portion (130) of the frame and attach to the edges larger circular cutout of the oxygen port (140). For example, the frame extensions may attach beyond the outer aperture of the oxygen port (140) to the anterior side of the mask body (102), beyond the outer aperture of the oxygen port (140) to the posterior side of the mask body (102) or to the edges of the outer aperture (142) of the oxygen port (140) between the anterior side and the posterior side of the mask body (102). The oxygen port may further include a filter membrane (126) between the inner aperture (144) of the oxygen port (140) and the outer aperture (142) of the oxygen port (140). In certain embodiments, the filter membrane (126) is positioned on the anterior side of the frame between the outer aperture and the inner aperture of the oxygen port (140), and the frame is positioned on the posterior side of the filter membrane providing structural support to the filter membrane (126). As mentioned above, the inner aperture (144) of the oxygen port (140) houses the oxygen port adapter (146). Thus, the oxygen port adapter (146) is surrounded by the filter membrane (126). The oxygen port adapter (146) utilized may be a capped oxygen port adapter (146) which itself provides an aperture through the mask body (102). In other embodiments, the oxygen port (140) may also engage a non-rebreathing bag adapter in addition to an oxygen port adapter (146).

Figure 59:
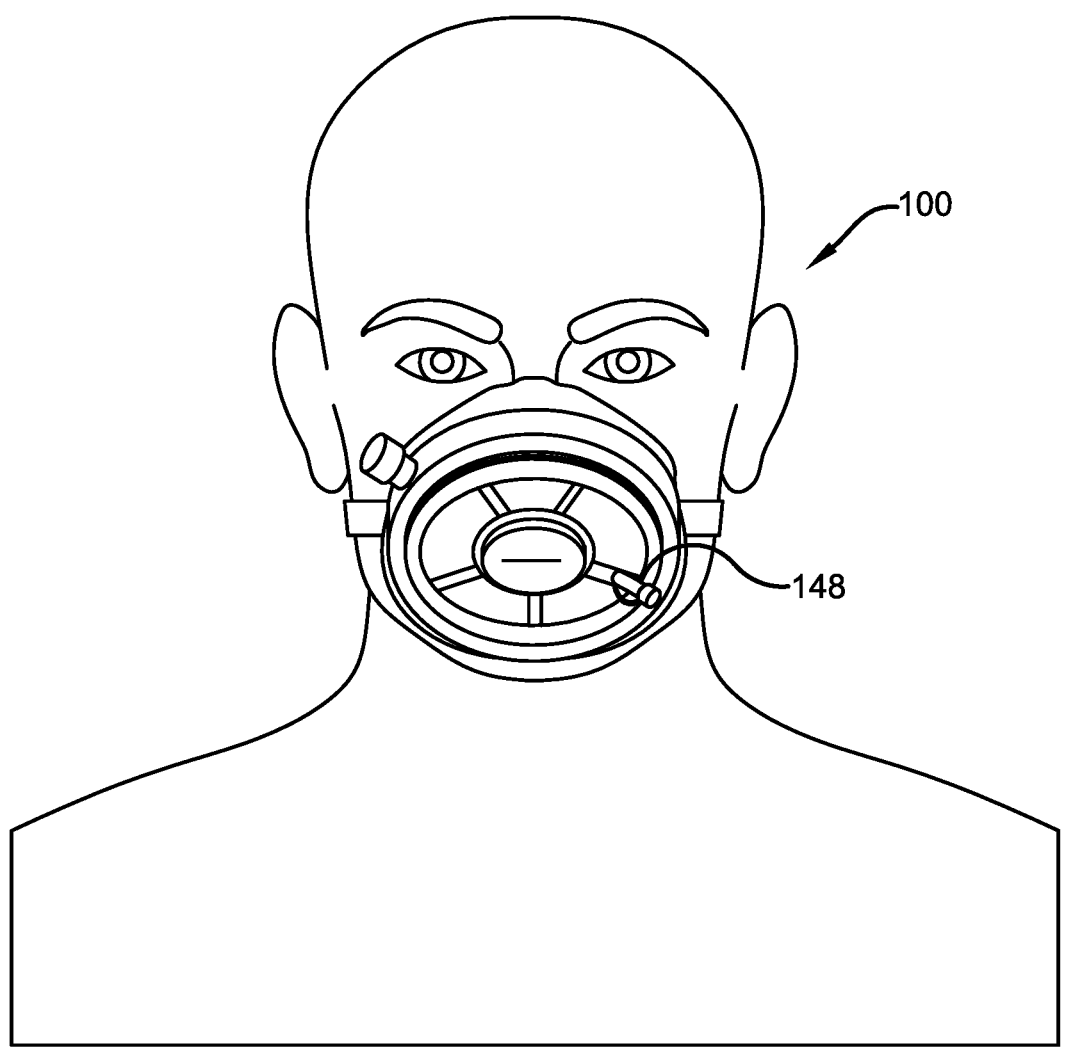
FIG. 59 is an exemplary embodiment of a filtering facepiece respirator illustrating a luer port incorporated into the frame (e.g., the spokes) of the adapter (e.g., a filtered slit port cap assembly).
Figure 60A:
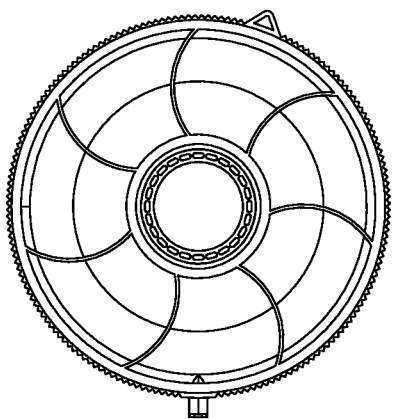
FIGS. 60A, 60B, 60C, 60D and 60E illustrate an exemplary embodiment including various views of an adapter or cap assembly having a fin-shaped frame.
Figure 60B:
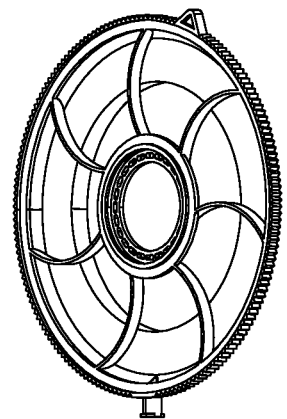
Figure 60C:
Figure 60D:
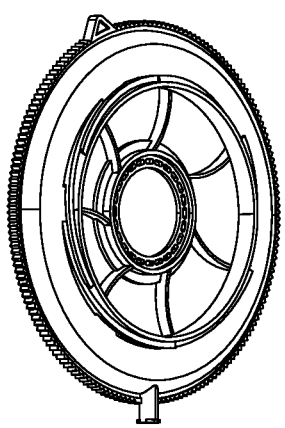
Figure 60E:
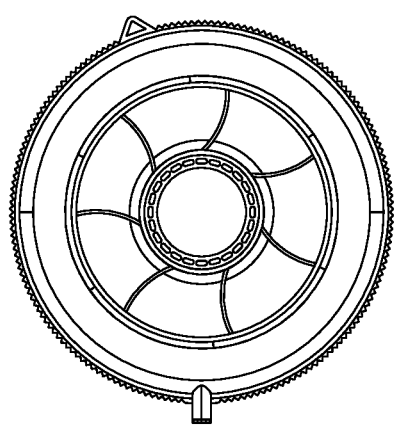

As mentioned above, the filtering facepiece respirator (100) may further include a luer port (148) positioned on a first anterior side portion or a second anterior side portion of the mask body (102). The luer port (148) is formed from a cut-out within the mask body (102) which provides an aperture from the anterior portion of mask body (102) to the posterior portion of the mask body (102). Typically, the cut-out which forms the luer port (148) is circular although any shape cut-out may be formed within the mask body for the luer port (148). This circular cut-out may be referred to as the outer aperture (150) of the luer port (148). According to certain aspects of the present teaching, the aperture which forms the luer port (148) may further include a frame. The frame may include a circular portion (130) having a diameter which is less than the diameter of the outer aperture (150) of the luer port (148). The circular portion (130) of the frame may also include an inner aperture (152) allowing for insertion of a luer port adapter (154) within the inner aperture (152) of the luer port (148). The frame may further include a suitable number of frame extensions which extend from the circular portion of the frame and attach to the edge's larger circular cutout of the luer port (148). For example, the frame extensions may attach beyond the outer aperture (150) of the luer port (148) to the anterior side of the mask body (102), beyond the outer aperture (150) of the luer port (148) to the posterior side of the mask body (102) or to the edges of the outer aperture (150) of the luer port (148) between the anterior side and the posterior side of the mask body (102). The luer port (148) may further include a filter membrane (126) between the inner aperture (152) of the luer port (148) and the outer aperture (150) of the luer port (148). In certain embodiments, the filter membrane (126) is positioned on the anterior side of the frame between the outer aperture (150) and the inner aperture (152) of the luer port (148) and the frame is positioned on the posterior side of the filter membrane (126) providing structural support to the filter membrane (126). As mentioned above, the inner aperture (152) of the luer port houses the luer port adapter (154). Thus, the luer port adapter (154) is surrounded by the filter membrane (126). The luer port adapter (154) utilized may be a capped luer lock which itself provides an aperture through the mask body (102). The luer port adapter (154) may be used for capnography measurement and other uses. In certain embodiments, the luer port (148) may be positioned on the frame of the cap assembly (e.g., the frame of the filtered slit port cap assembly, the frame of the slit port cap assembly or the frame filtered cap assembly). For example, FIG. 59 illustrates the luer port (148) positioned on the frame of the filtered slit port cap assembly.

Figure 44:
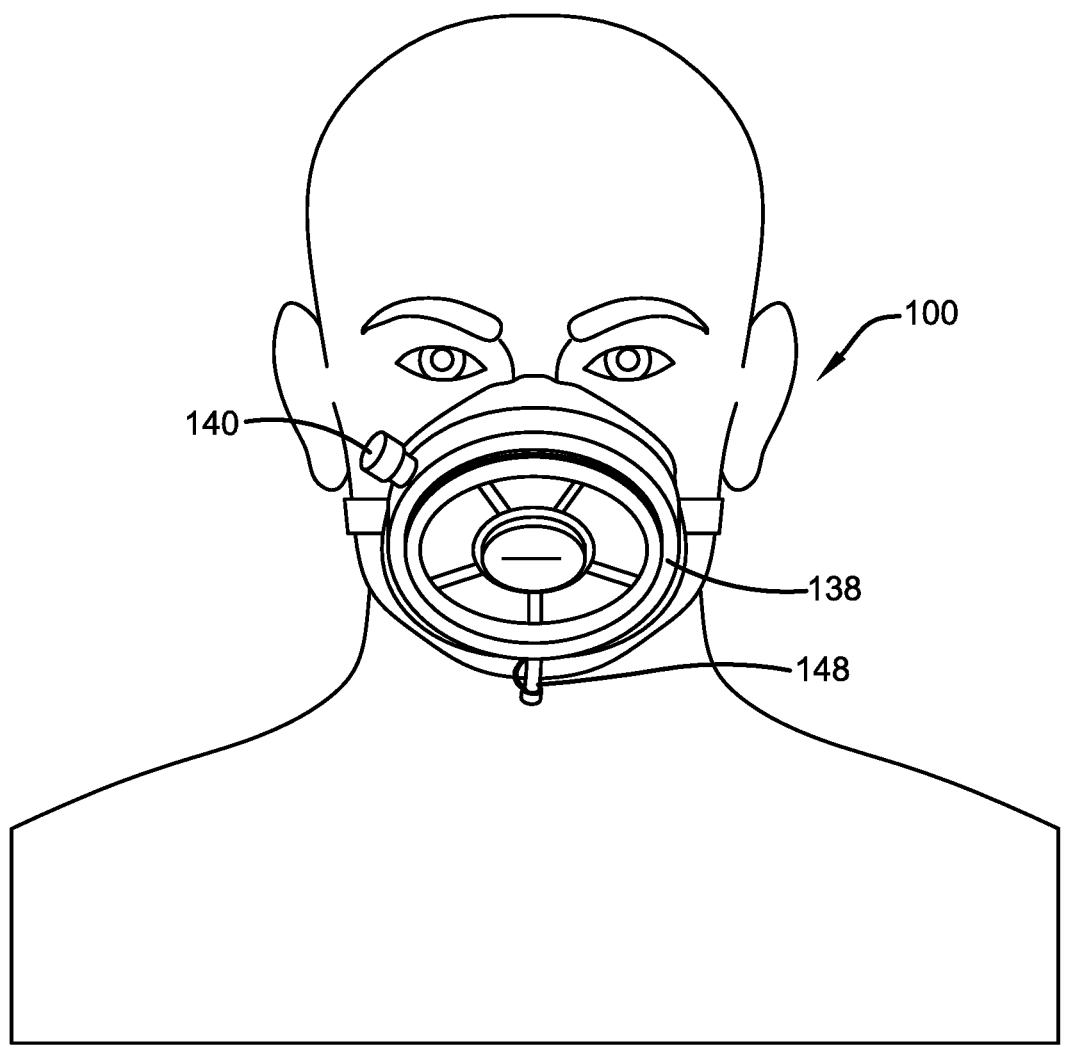
FIG. 44 is an exemplary embodiment of a filtering facepiece respirator.
Figure 45:
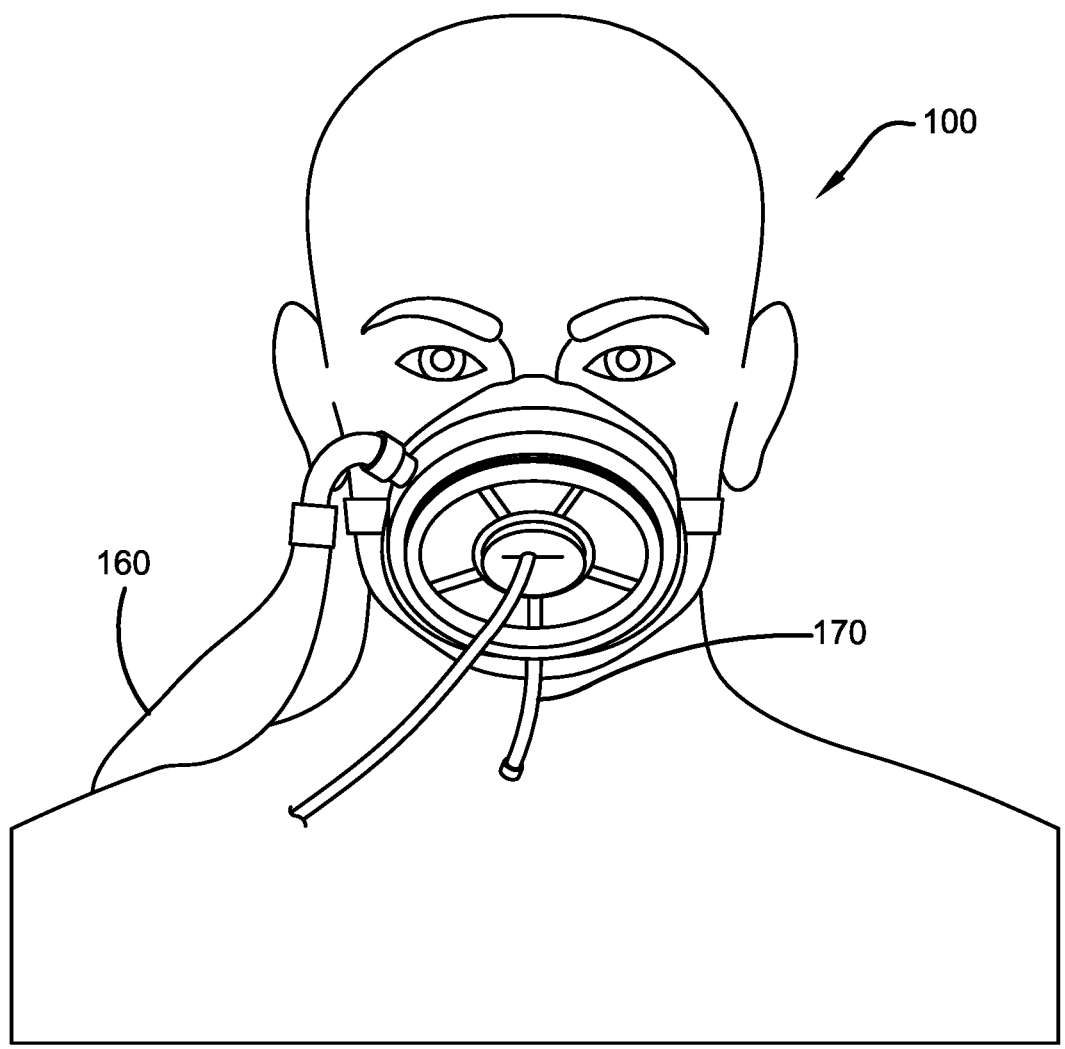
FIG. 45 is an exemplary embodiment of a filtering facepiece respirator with breathing bag attached to the oxygen port.

FIGS. 44 to 59 illustrate additional embodiments of the filtering facepiece respirator. FIG. 44 illustrates a filtered slit port cap assembly positioned engaged to the filtering facepiece respirator (100) and having an oxygen port (140) and a luer port (148). FIG. 45 illustrates the filtering facepiece respirator having a tube/catheter (170) engaged to the luer port and an oxygen port adapter/breathing bag/non-rebreathing bag/non-rebreathing bag adapter (160) which may be engaged to the oxygen port (140).

FIG. 45 also shows an instrument which is insertable through the slit in the filtered slit port cap assembly. The slit may be formed in a membrane that is made from silicone. The membrane forms a seal (e.g., an elastomeric seal) around the instrument as the slit encapsulates and provides a seal around the instrument that is inserted through it. In certain embodiments, the slit, due to the nature of the membrane, is readily expandable to accommodate the size of the instrument that is inserted therethrough. The features of the slit described above may be achieved by the material employed to fabricate the membrane. In certain embodiments, the membrane in which the slit is formed is made from silicone. In further embodiments, the membrane in which the slit is formed is made from a resin or a thermoplastic elastomer, an example of which is Avient Versaflex™ CL2000X provided by Avient (Avon Lake, Ohio). Alternative embodiments of a cap assembly that includes the membrane and slit as described herein are illustrated in FIGS. 50 to 52, 56 (which illustrates the expandable nature of the slit in the membrane as the slit is capable of accommodating the insertion of multiple instruments) and 57.

FIG. 46 illustrates various types of cap assemblies referenced above that may be used to engage the filtering facepiece respirator.

Figure 47:
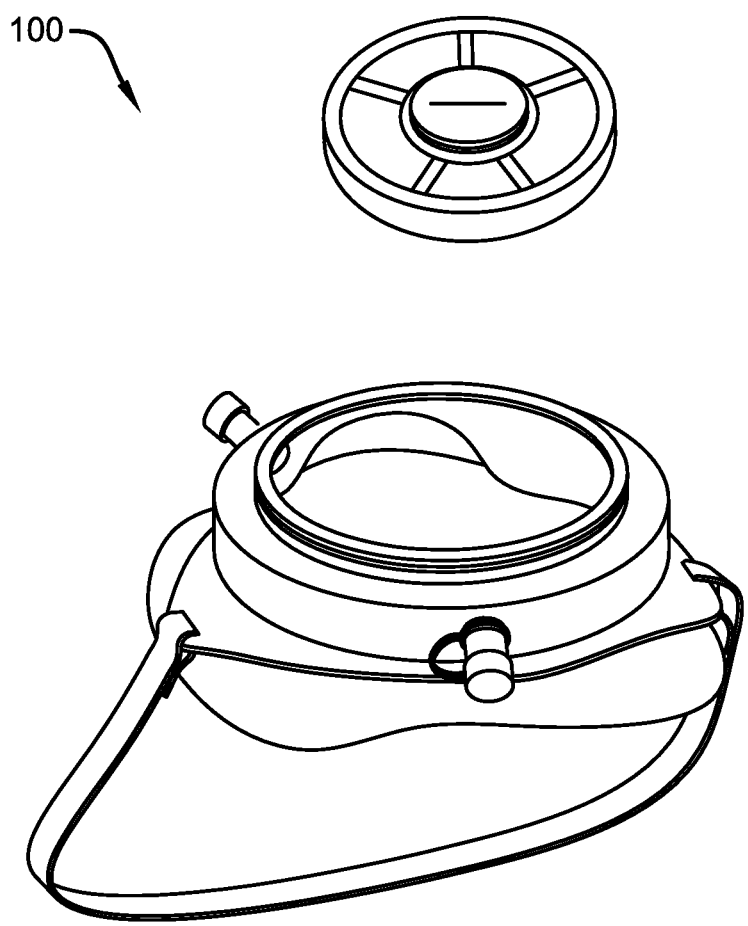
FIG. 47 is a side view of an exemplary embodiment of a filtering facepiece respirator illustrating an adapter removed from the filtering facepiece respirator.

FIG. 47 provides a side view of the filtering facepiece respirator with the cap assembly disengaged. Various types of mechanisms may be used to engage the cap assembly to the filtering facepiece respirator including a snap coupling, screw threads or a tabular protrusion and a receiving portion for engaging the cap assembly to the primary port as mentioned herein. The snap coupling may be formed by at least two flanges on the cap assembly forming a space therebetween which is capable of engaging a flange positioned on the primary port in the space formed between the two flanges of the cap assembly. In an alternative embodiment, the primary port may include at least two flanges which forms a space therebetween which is capable of engaging a flange positioned on the cap assembly. In an alternative embodiment, as mentioned herein, a tabular protrusion on either the primary port or the cap assembly is capable of engaging a receiving structure positioned respectively in either the cap assembly or the primary port.

Figure 48:
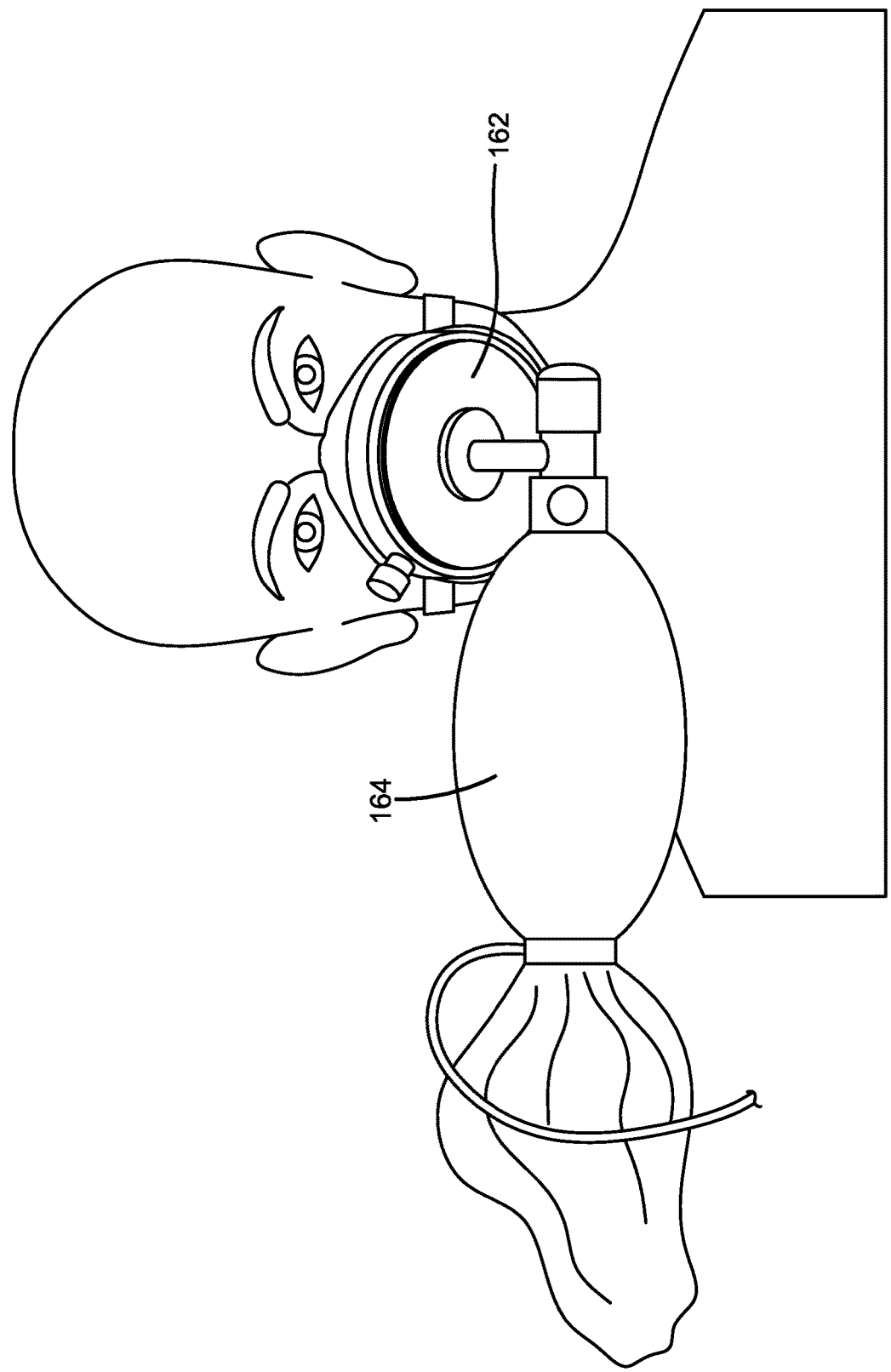
FIG. 48 is an exemplary embodiment of a filtering facepiece respirator including a cardiopulmonary resuscitation (CPR) adapter which converts the mask into a cardiopulmonary resuscitation mask.
Figure 49:
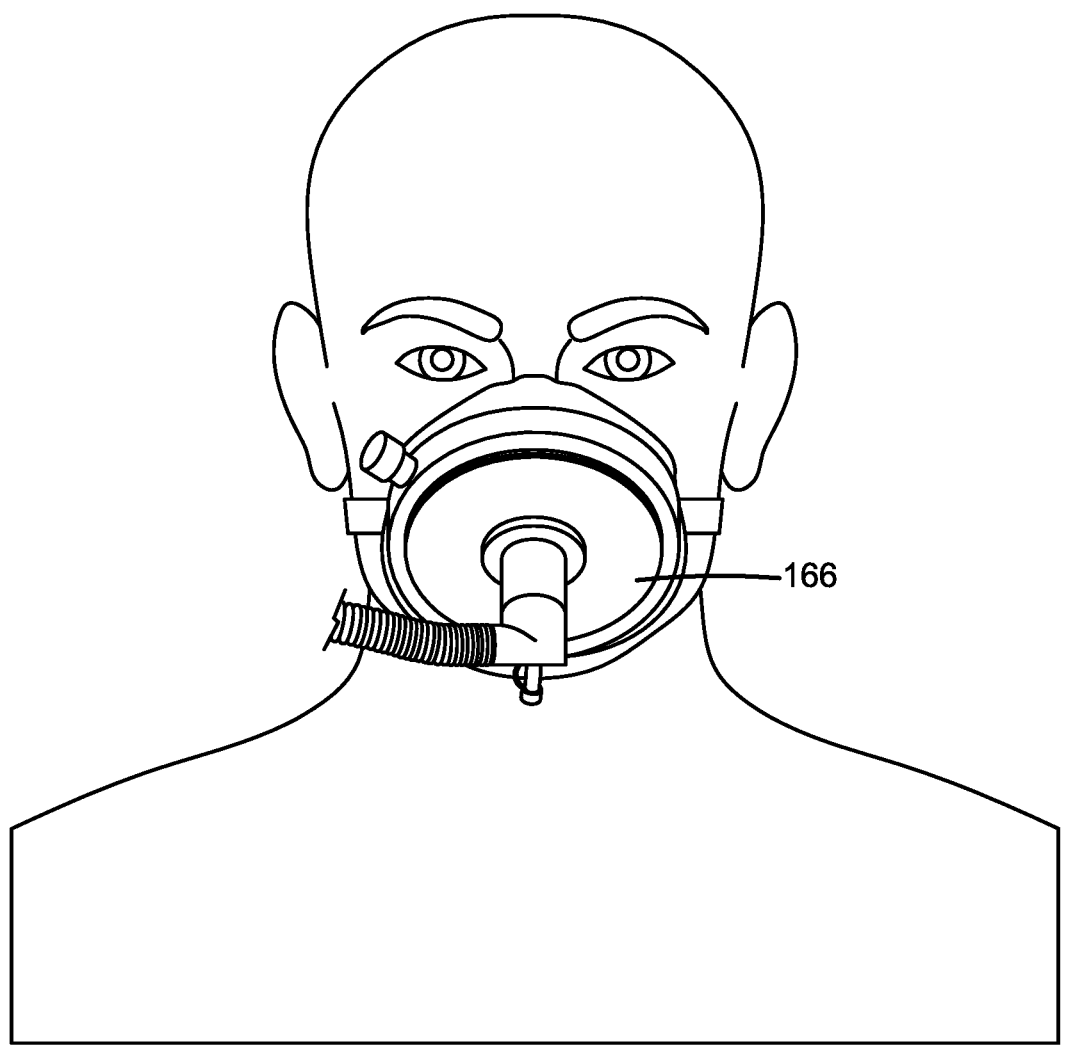
FIG. 49 is an exemplary embodiment of a filtering facepiece respirator including a continuous positive airway pressure (CPAP) or bilevel positive airway pressure (BIPAP) adapter which converts the mask into a CPAP or BIPAP mask.
Figure 50:
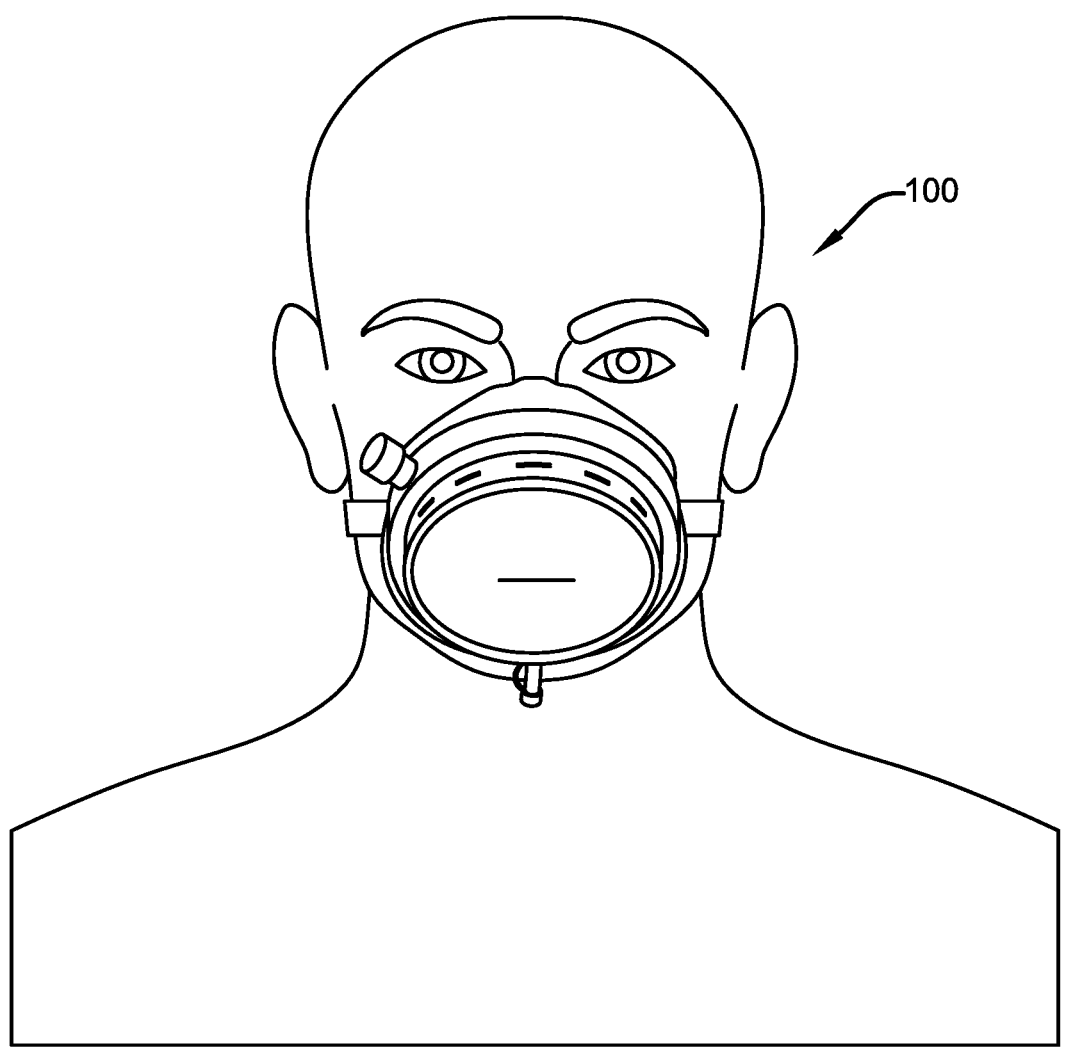
FIG. 50 is an exemplary embodiment of a filtering facepiece respirator.
Figure 51:
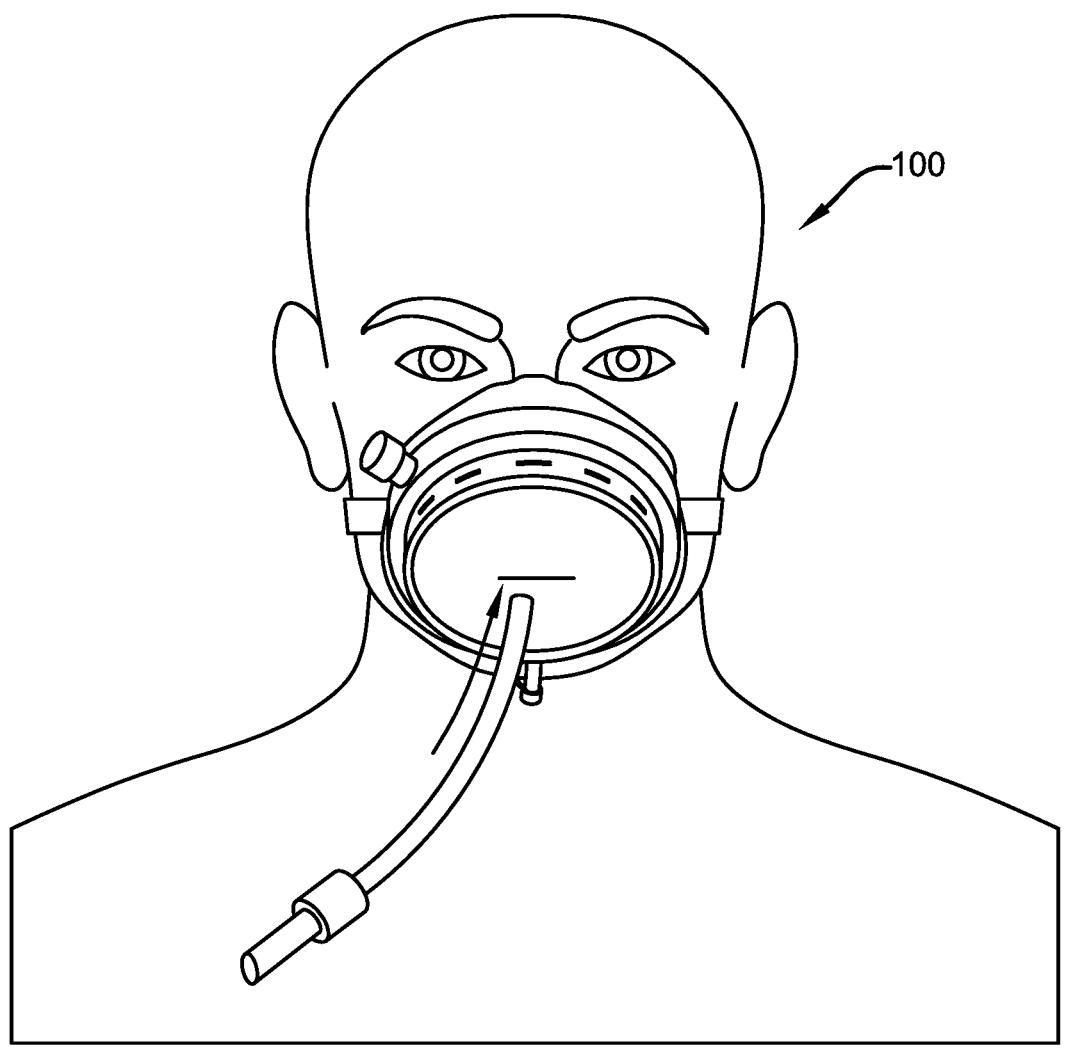
FIG. 51 is an exemplary embodiment of a filtering facepiece respirator with an instrument being inserted into a slot in the respirator.
Figure 52:
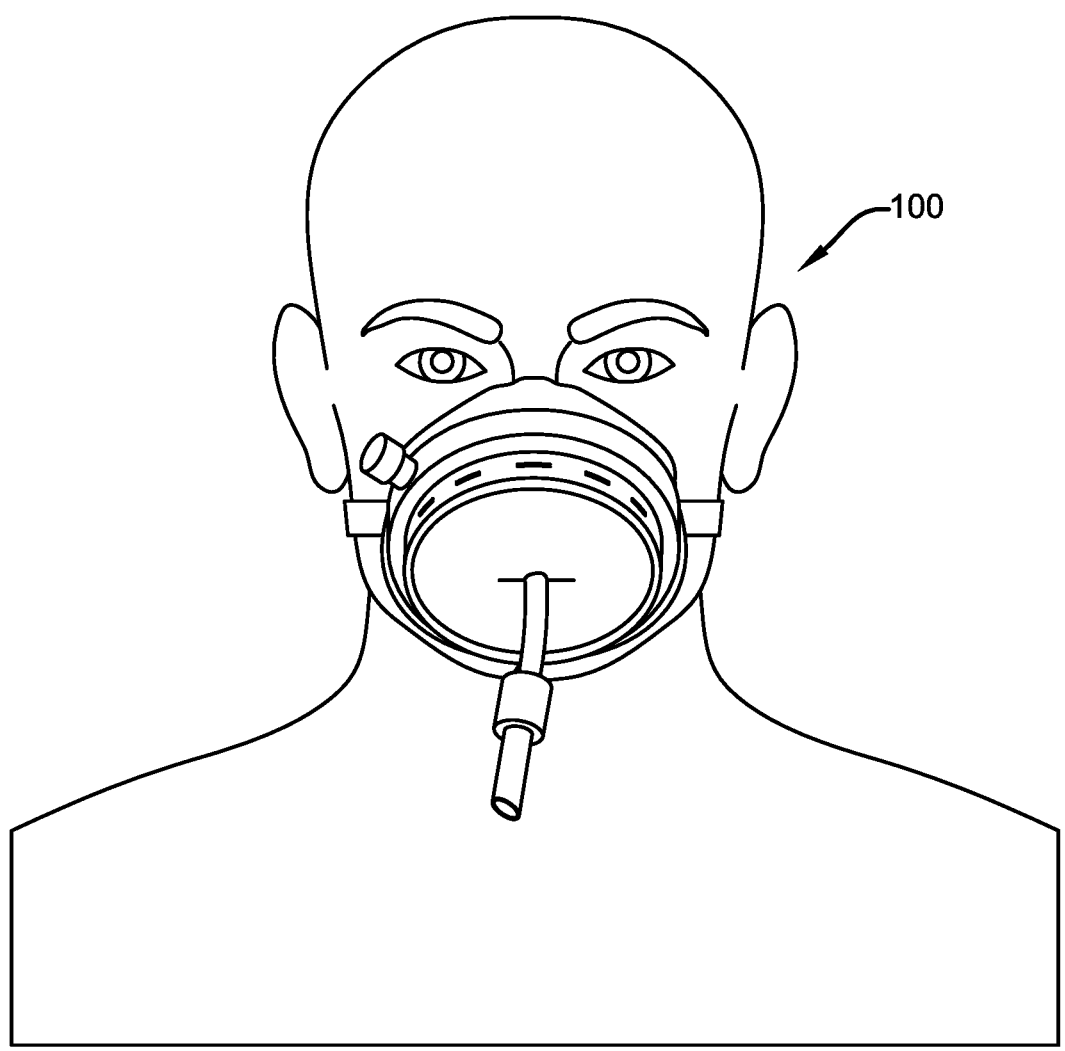
FIG. 52 is an exemplary embodiment of a filtering facepiece respirator with an instrument inserted into a slot in the respirator.
Figure 53:
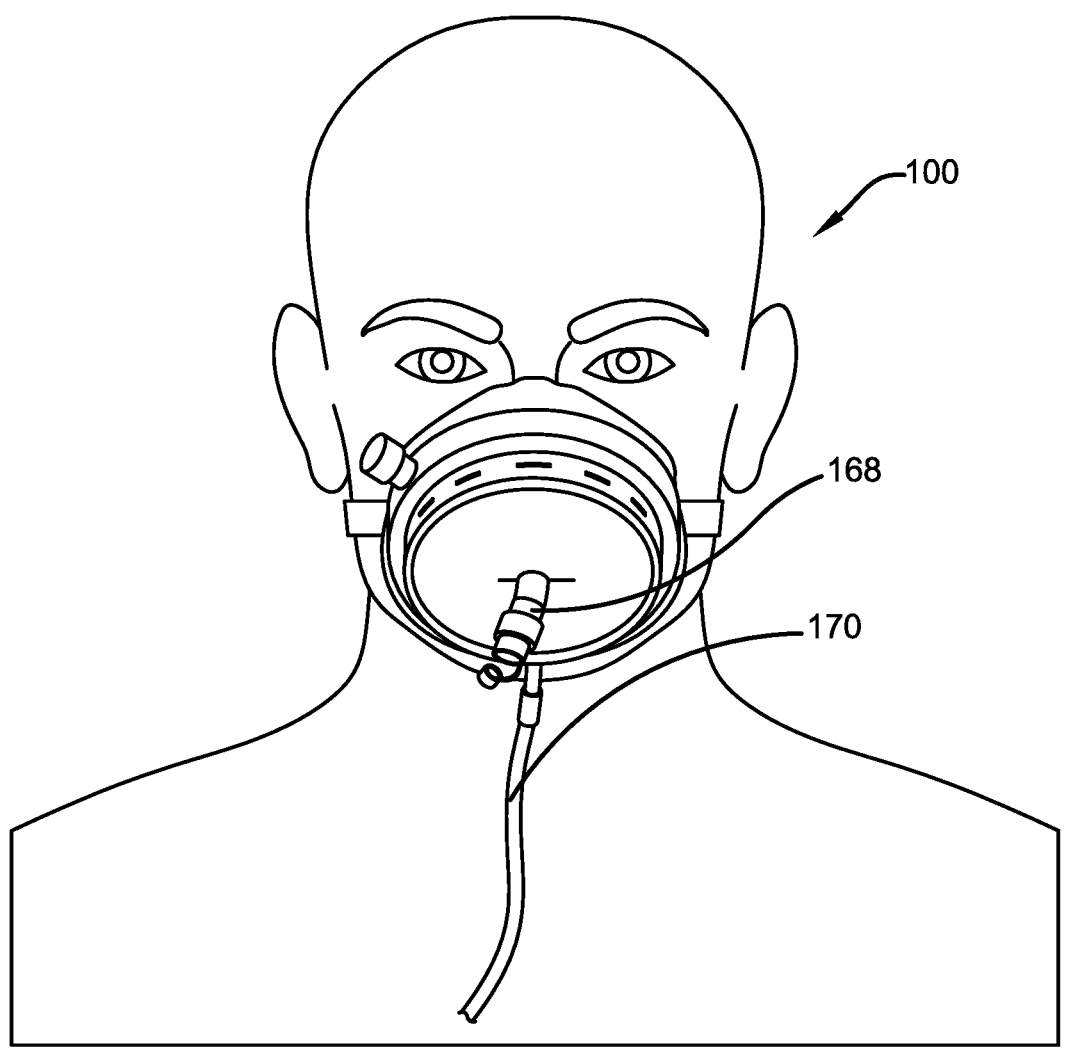
FIG. 53 is an exemplary embodiment of a filtering facepiece respirator with an instrument (e.g., a tracheal intubation) inserted into the slot and a catheter attached to the luer port.
Figure 54:
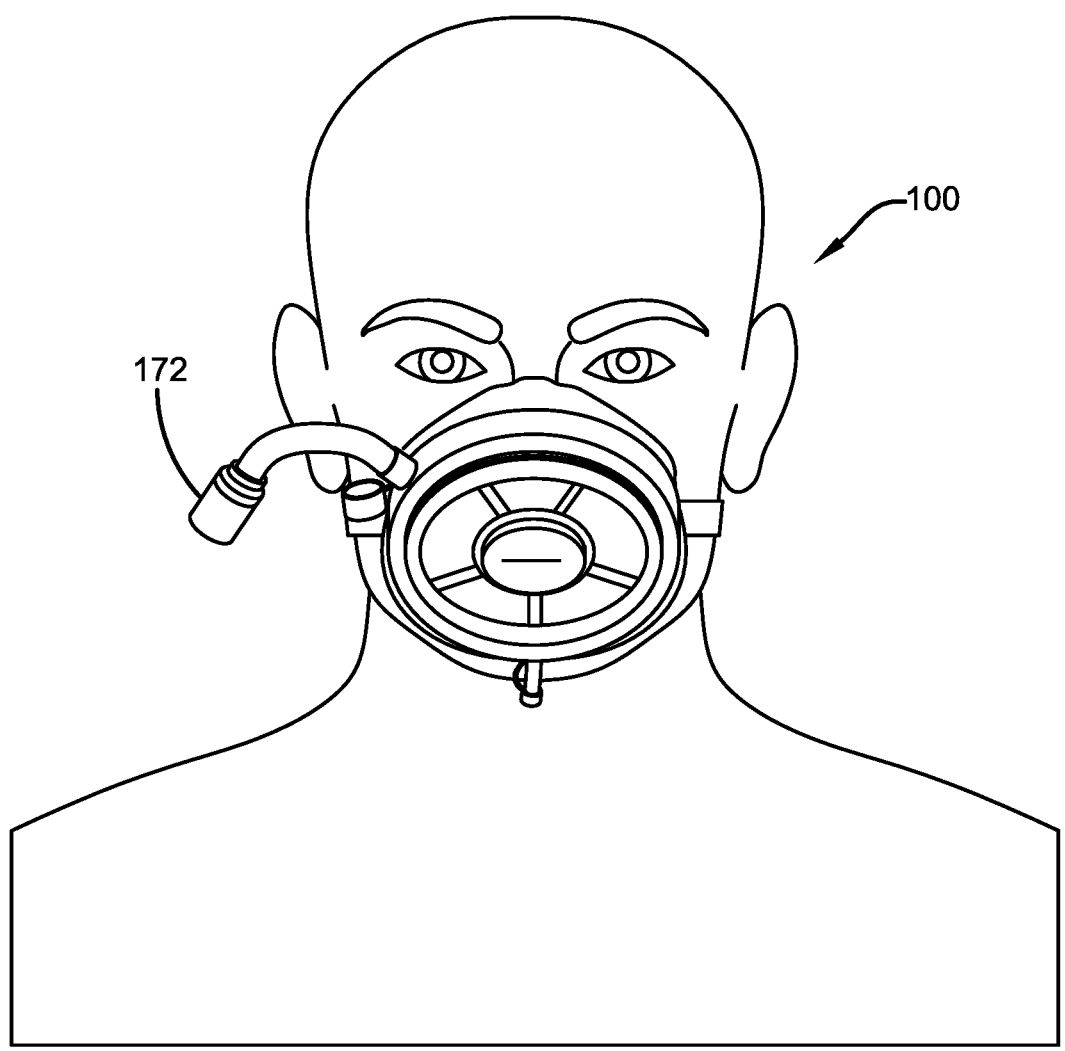
FIG. 54 is an exemplary embodiment of a filtering facepiece respirator with a nebulizer attached to the oxygen port.
Figure 55:
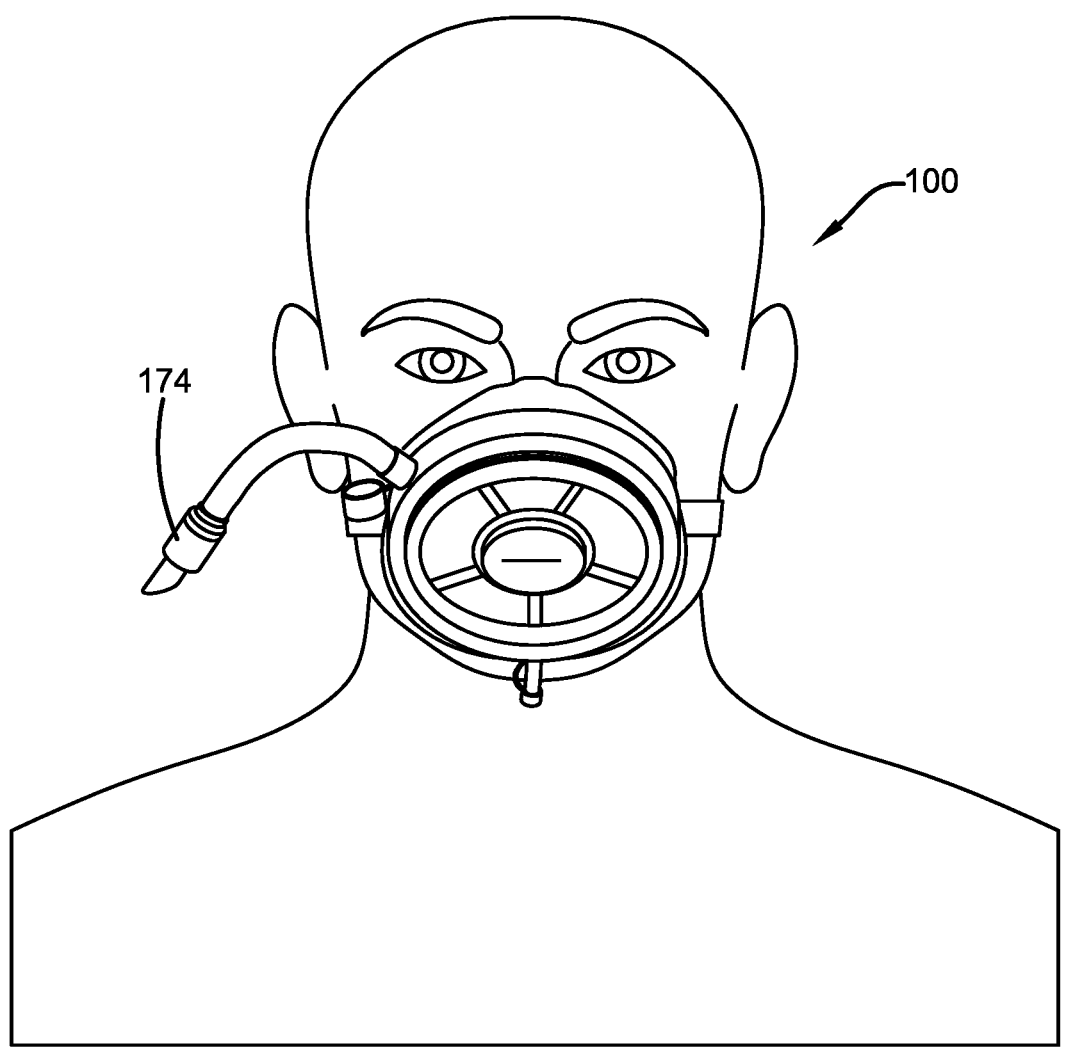
FIG. 55 is an exemplary embodiment of a filtering facepiece respirator with a venturi adapter attached to the oxygen port.
Figure 56:
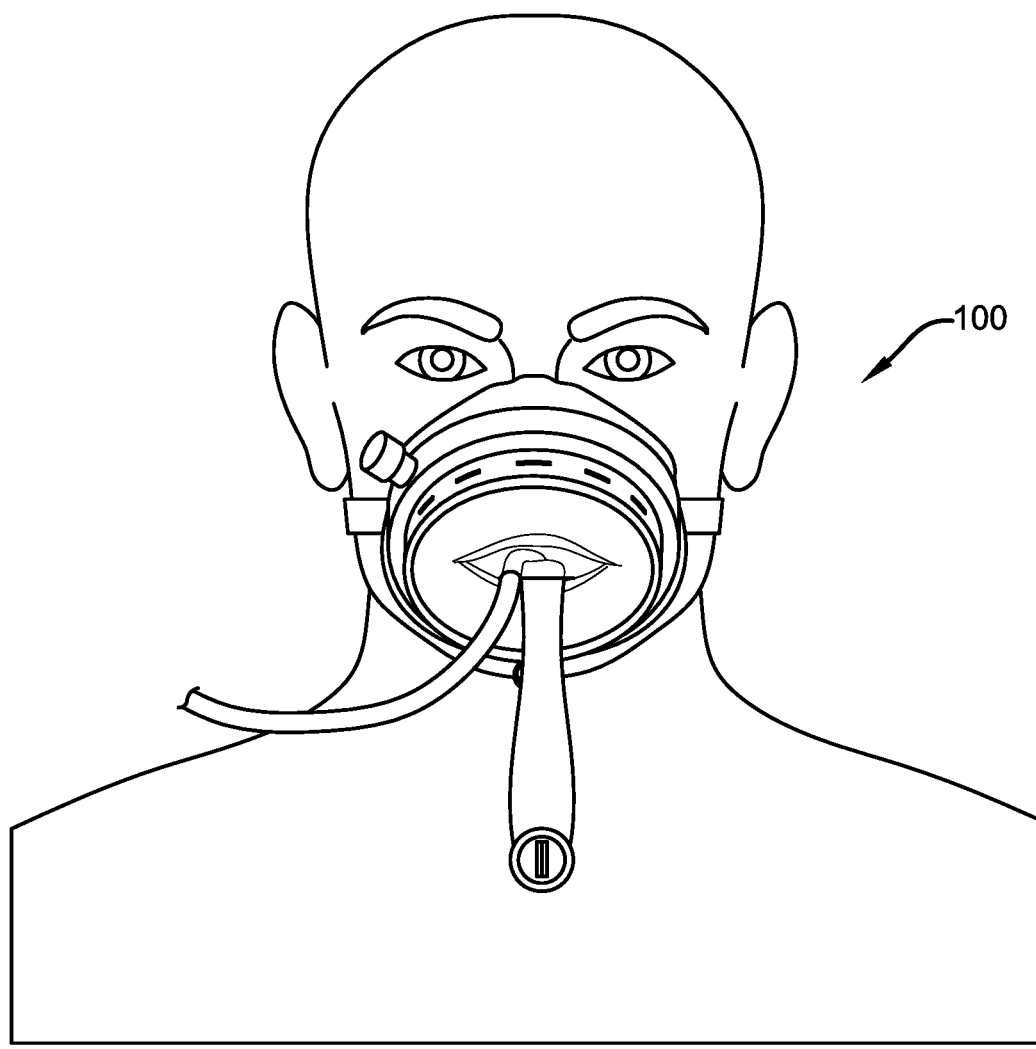
FIG. 56 is an exemplary embodiment of a filtering facepiece respirator with instruments inserted through a slit in the respirator.
Figure 57:
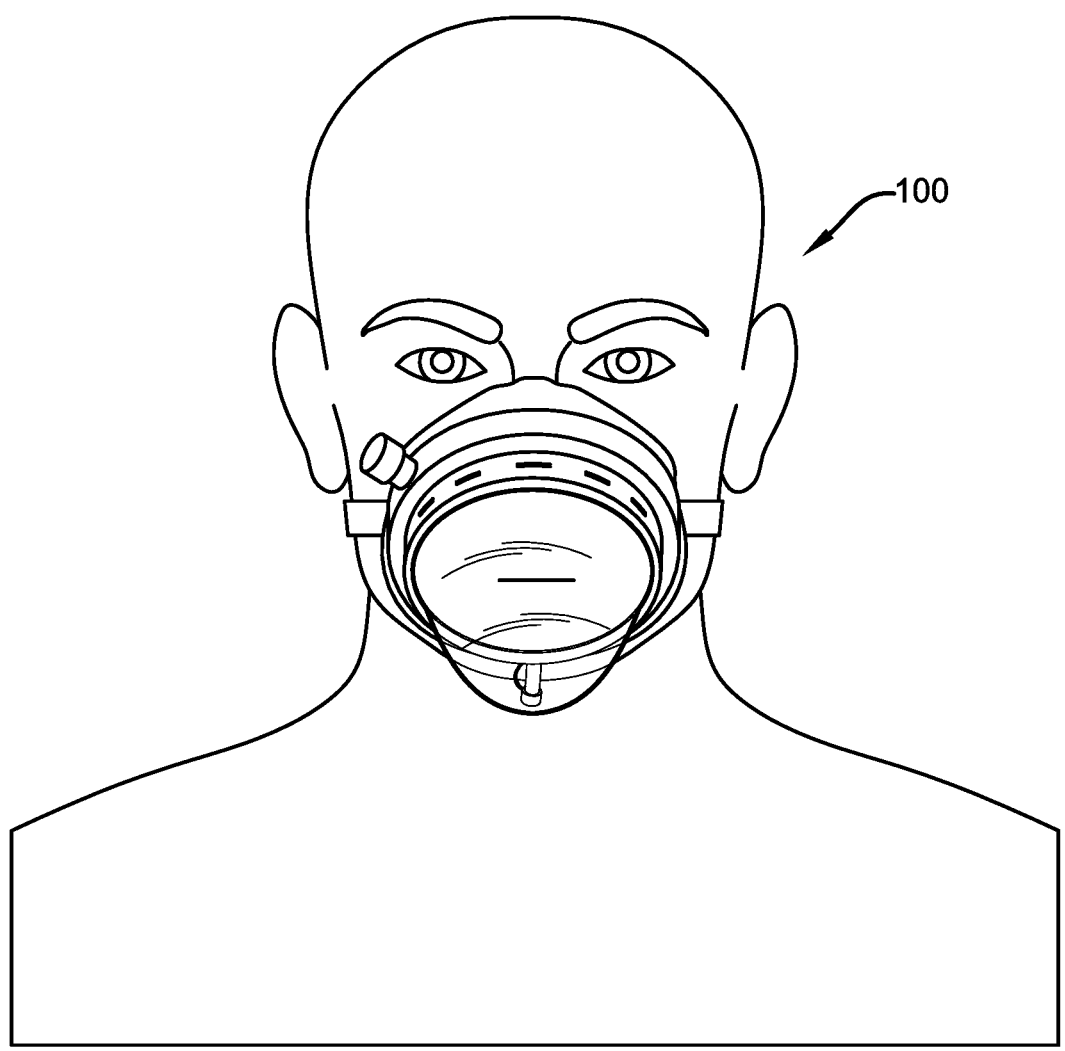
FIG. 57 is an exemplary embodiment of a filtering facepiece respirator illustrating the luer port positioned, for example, at the bottom side of the mask.

The cap assembly on the filtering facepiece respirator may be replaced with various types of adapters to convert the respirator into an alternate functioning device. For example, FIG. 48 illustrates a cardiopulmonary resuscitation (CPR) adapter (162) and a cardiopulmonary resuscitation (CPR) device (164) which converts the respirator into a cardiopulmonary resuscitation (CPR) respirator or mask. FIG. 49 illustrates continuous positive airway pressure (CPAP) adapter or bilevel positive airway pressure (BIPAP) adapter (166) which converts the respirator into a continuous positive airway pressure (CPAP) adapter or bilevel positive airway pressure (BIPAP) respirator or mask. FIG. 53 illustrates a tracheal intubation (168) inserted in the slit in the membrane of the cap assembly and a catheter or tube (170) connected to the luer port. FIG. 54 illustrates a nebulizer (172) attached to the oxygen port. FIG. 55 illustrates a Venturi adapter (174) attached to the oxygen port.

As noted above, the adapters associated with the filtering facepiece respirator including but not limited to the primary port adapter, the oxygen adapter and the luer adapter described above are detachable and interchangeable with other adapters for use with the filtering facepiece respirator. The filter membrane or filter media material used within the primary port, oxygen port and luer port may include a single or multiple microfiber filtering layers of varying thickness. The filter membrane or filter media material used within the primary port, oxygen port and luer port may be made of polypropylene and polyester polyfiber compositions or any other suitable material known to a person of ordinary skill in the art.

In a further embodiment of the filtering facepiece respirator, filter media material (e.g., a filter membrane) may be positioned over at least a portion of the posterior portion of the mask body and may be positioned over or cover at least the ports or apertures within the mask body. For example, filter media material may be positioned to cover the primary port aperture and the oxygen port aperture and the luer port aperture in embodiments that also include an oxygen port aperture and/or a luer port aperture. In further embodiments, filter media material may cover the entire surface of the posterior portion of the mask body. The filter media material may include a single or multiple microfiber filtering layers of varying thickness. The filter media material may further be made of polypropylene and polyester polyfiber compositions, or any other suitable material known to a person of ordinary skill in the art. In certain embodiments, the filter media may include an N95-rated filter media capable of providing a filtration efficiency of at least 95% against non-oily particles. In other embodiments, the filter media may comply with any other filtration standards within the industry and may have any filtration rating within the industry. The filter media material may be secured to the posterior portion of the mask body through ultrasonic welding, UV cured gluing or traditional gluing of the filter media material to the posterior portion of the mask body. Accordingly, also provided herein is a process for making a filtering facepiece respirator which includes the following steps: 1) forming a mold of the mask body made from silicone or a medical grade plastic; 2) cutting a primary port aperture, optionally, an oxygen port aperture and optionally, a luer port aperture within the mold of the mask body mold; 3) forming at least one mold of the filter media made from filter media material to be positioned over at least a portion of the posterior portion of the mask body (e.g., over the primary port aperture, the oxygen aperture and luer aperture of the mask body); 4) cutting a primary port aperture, an oxygen port aperture and a luer port aperture within the filter media material (these apertures may be equivalent in size or smaller in size to the corresponding apertures in the mask body mold; and 5) securing the filter media material to the posterior portion of the mask body through ultrasonic welding, UV cured gluing or traditional gluing of the filter media material to the posterior portion of the mask body.

In a further embodiment of the present disclosure, the mask body of the filtering facepiece respirator may be positioned over an N95-rated or other filtration rated mask. However, the mask body may be positioned over a mask having any filtration rating. In further embodiments, the N95-rated or other filtration rated mask may include cutouts or apertures corresponding to apertures present within the mask body of the filtering facepiece respirator including a primary port aperture and optionally an oxygen port aperture and/or a luer port aperture, if present within the mask body. The N-95-rated or other filtration rated mask may be secured to the posterior side portion of the of the mask body by ultrasonic welding, UV cured gluing, or traditional gluing of the edges of the N95-rated or other filtration rated mask to the outside edges of the mask body. In further embodiments, the N-95 or other filtration rated mask may include at least one of a primary port, an oxygen port and a luer port corresponding to a primary port, oxygen port and luer port that may be present on the mask body.

In a further embodiment of the present disclosure, the mask body of the filtering facepiece respirator is not made of silicone or a medical grade plastic but rather is made from a filter media material. The filter media material may include a single or multiple microfiber filtering layers of varying thickness. The filter media material may further be made of polypropylene and polyester polyfiber compositions or any other suitable material known to a person of ordinary skill in the art. In certain embodiments, the filter media may be made from an N95 rated filter media capable of providing a filtration efficiency of at least 95% against non-oily particles. In other embodiments the filter media may be made from a material having a filtration rating other than N95. In certain embodiments, the filter media may be made from an electroceutical fabric. The filter media facepiece respirator may include any of the features described above with respect to the mask body including but not limited to a primary port, an optional oxygen port and an optional luer port.

The primary ports (158), luer ports (148) and oxygen ports (140) describe above and shown in the Figures may vary in size. The adapter fittings capable of engaging these ports including snap fittings, friction fittings, screw fittings any outer suitable fitting known to a person of skill in the art. The ports described above may further be provided in various combinations (e.g., with one, two or all three ports being present on the mask body) and arrangements on the mask body. For example, in certain embodiments, the mask may include an oxygen port and a primary port.

The respirator of the present invention may have alternative applications. The respirator may be used in any industry that requires putting on a mask for protection. The respirator may be used in conjunction with electronic devices for measuring $CO_2$, $VO_2$, temperature and other performance metrics. The device may be used in a recreational setting along with electronic nicotine delivery systems, breathalyzers and other auxiliary devices. Devices can be substituted for the detachable plate (5) or primary port adapter to measure spirometry, exhaled breath temperature, capnography, oxygen concentrations, alcohol, ketones, pathological sampling and various other types of biological measurements. A device that can be substituted for the detachable plate (5) or primary port adapter includes but is not limited to a breath test diagnostic tool for measuring gases like $CO_2$, hydrogen and other gases for diagnostic tests for lactose and fructose intolerances, bacterial overgrowth, H pylori etc. Devices can be substituted for the detachable plate (5) or primary port adapter for delivery of oxygen, air, humidity, suction forces, nebulized medications, inhaled medication/agents (metered dose or otherwise) and other delivery systems. Devices can be substituted for the detachable plate to deliver UV light or other forms of treatment.

The filtering facepiece respirator disclosed herein may be worn by patients before procedures, during airway instrumentation, and after procedures, as herein described and disclosed. The filtering facepiece respirator distinguishes over previous masks by providing additional filter/sealing layers around both the instrumenting device and the patient's face.

Further, to the extent the present application discloses a method, it is contemplated that a system of apparatuses configured to implement the method are also within the scope of the present disclosure.

The following paragraphs describe various embodiments disclosed herein.

An embodiment of a filtering facepiece respirator includes a mask body having an anterior side, a posterior side, a middle portion, a first side portion, a second side portion, a top side portion, a bottom side portion and outer edge portions; a primary port positioned on the mask body; fasteners for attaching and securing adjustable bands to the first side portion and to the second side portion of the mask body; and, a detachable primary port adapter which is positioned over and engages the primary port, wherein the detachable primary port adapter includes a cap assembly, wherein the cap assembly is in the shape of a circular conduit.

A subsequent embodiment of the filtering facepiece respirator includes a nose bridge positioned at the top side portion of the mask body.

A subsequent embodiment of the filtering facepiece respirator including any of the previous or subsequent embodiments includes a cap assembly having a first end and a second end, wherein the first end of the cap assembly includes a snap coupling, screw threads or a tabular protrusion for engaging the cap assembly to the primary port, wherein the snap coupling is formed by at least two flanges on the cap assembly forming a space therebetween, wherein the two flanges on the cap assembly are capable of engaging a flange positioned on the primary port in the space formed between the two flanges of the cap assembly, and wherein the tabular protrusion is capable of engaging a receiving structure in the primary port.

A subsequent embodiment of the filtering facepiece respirator including any of the previous or subsequent embodiments includes a cap assembly having one of the following: i) a filtered cap assembly, wherein the filtered cap assembly includes a filter membrane and has a proximal end and a distal end with respect to the anterior side of the mask body; ii) a slit port cap assembly, wherein the slit port cap assembly includes a self-sealing membrane having a slit port, does not include a filter membrane and has a proximal end and a distal end with respect to the anterior side of the mask body; or iii) a filtered slit port cap assembly, wherein the filtered slit port cap assembly includes a self-sealing membrane having a slit port surrounded by a filter membrane and has a proximal end and a distal end with respect to the anterior side of the mask body.

A subsequent embodiment of the filtering facepiece respirator including any of the previous or subsequent embodiments includes the filtered cap assembly and the filtered slit port cap assembly having a filter frame positioned on the posterior side of the mask body providing support to the filter membrane.

A subsequent embodiment of the filtering facepiece respirator including any of the previous or subsequent embodiments includes the self-sealing membrane of the slit port cap assembly and the filtered slit port cap assembly made of silicone, a transparent thermoplastic elastomer or a medical grade rubber and wherein the slit port in the self-sealing membrane is capable of receiving and sealing an instrument inserted therethrough.

A subsequent embodiment of the filtering facepiece respirator including any of the previous or subsequent embodiments includes the mask body further having an oxygen port positioned on the mask body.

A subsequent embodiment of the filtering facepiece respirator including any of the previous or subsequent embodiments includes the oxygen port being capable of engaging an oxygen port adapter, a breathing bag, a non-rebreathing bag, a non-rebreathing bag adapter, a nebulizer and a Venturi oxygen adapter.

A subsequent embodiment of the filtering facepiece respirator including any of the previous or subsequent embodiments includes the primary port, upon removal of the detachable primary port adapter cap assembly being capable of engaging one of the following: an adapter for oxygen delivery, a cardiopulmonary resuscitation (CPR) adapter, a continuous positive airway pressure (CPAP) adapter, a bilevel positive airway pressure (BIPAP) adapter, an adapter for delivery of anesthesia, an adapter for nebulized medications/substances; an aerosol shell adapter, an adapter for a PEEP valve attachment, an adapter for a device for taking breath samples with vacuum tubes, an adapter for an electronic device for measurement of spirometry/$CO_2$/temperature, an adapter for a humidifying and/or vaporizing device; an adapter for an electronic breathalyzer device, an adapter for an electronic nicotine delivery system, and an adapter for a UV light device.

A subsequent embodiment of the filtering facepiece respirator including any of the previous or subsequent embodiments includes the mask body further having a luer port positioned on the mask body.

A subsequent embodiment of the filtering facepiece respirator including any of the previous or subsequent embodiments includes the mask body further having a luer port positioned on the mask body.

A subsequent embodiment of the filtering facepiece respirator including any of the previous or subsequent embodiments includes the luer port having a luer port adapter, wherein the luer port adapter has a capped luer lock and provides an aperture through the mask body.

A subsequent embodiment of the filtering facepiece respirator including any of the previous or subsequent embodiments includes the luer port positioned on the filter frame of the filtered cap assembly or filtered slit port cap assembly.

A subsequent embodiment of the filtering facepiece respirator including any of the previous or subsequent embodiments includes an exhalation valve position on the mask body or one of the filter frames, filter membrane or self-sealing membrane of the cap assembly.

A subsequent embodiment of the filtering facepiece respirator including any of the previous or subsequent embodiments includes filter media (also referred to as a filter membrane) positioned over and secured to the posterior side of the mask body.

A subsequent embodiment of the filtering facepiece respirator including any of the previous or subsequent embodiments includes the mask body being made of a filter media material (also referred to as a filter membrane).

A subsequent embodiment of the filtering facepiece respirator including any of the previous or subsequent embodiments includes the filter media material (also referred to as a filter membrane) having multiple microfiber filtering layers of varying thickness and polypropylene and polyester polyfiber compositions that provide rigidity and filtering functionality.

A subsequent embodiment of the filtering facepiece respirator including any of the previous or subsequent embodiments includes the filter media (also referred to as a filter membrane) made from an electroceutical fabric.

A subsequent embodiment of the filtering facepiece respirator including any of the previous or subsequent embodiments includes the mask body being made from silicone or a medical grade plastic material.

A subsequent embodiment of the filtering facepiece respirator including any of the previous or subsequent embodiments includes the mask body being transparent.

A subsequent embodiment of the filtering facepiece respirator including any of the previous or subsequent embodiments includes the oxygen port having a filter membrane and a filter frame positioned on the posterior side of the mask body.

A subsequent embodiment of the filtering facepiece respirator including any of the previous or subsequent embodiments includes the luer port having a filter membrane and a filter frame positioned on the posterior side of the mask body, wherein an aperture within the capped luer lock is surrounded by the filter membrane of the luer port.

A subsequent embodiment of the filtering facepiece respirator including any of the previous or subsequent embodiments includes the detachable primary port adapter including a 22 mm cap assembly.

A subsequent embodiment of the filtering facepiece respirator including any of the previous or subsequent embodiments includes a method of instrumenting an airway to the filtering facepiece respirator including the following steps: providing one of the slit port cap assembly or the filtered slit port cap assembly engageable to the primary port of the mask body; and, providing an instrument, wherein the instrument is insertable through an opening formed by a slit in the slit port cap assembly or a slit in the filtered slit port cap assembly through the mask body and into the posterior side of the mask body, wherein the slit port cap or the filtered slit port cap provides a seal between the instrument and the filtering facepiece respirator, wherein the above steps are capable of being performed while the filtering facepiece respirator is positioned on a patient or off a patient.

A subsequent embodiment of the filtering facepiece respirator including any of the previous or subsequent embodiments includes a filtering facepiece respirator having: a mask body having an anterior side, a posterior side, a middle portion, a first side portion, a second side portion, a top side portion, a bottom side portion and outer edge portions; a primary port positioned on the mask body; fasteners for attaching and securing adjustable bands to the first side portion and to the second side portion of the mask body; a detachable primary port adapter which is positioned over and engages the primary port, wherein the detachable primary port adapter includes a cap assembly, wherein the cap assembly is in the shape of a circular conduit and includes a filter frame, wherein the filter frame includes an inner circular portion and four frame extensions which extend from the inner circular portion to an inner surface of the circular conduit of the cap assembly.

A subsequent embodiment of the filtering facepiece respirator including any of the previous or subsequent embodiments includes a method of making a filtering facepiece respirator including the following steps: providing a mask body having an anterior side, a posterior side, a middle portion, a first side portion, a second side portion, a top side portion, a bottom side portion and outer edge portions; providing a primary port positioned on the mask body; providing a self-sealing membrane, wherein the self-sealing membrane is made of silicone, a transparent thermoplastic elastomer or a medical grade rubber; integrating the self-sealing membrane into a detachable primary port adapter, wherein the detachable primary port adapter is positioned over and engages the primary port, wherein the detachable primary port adapter includes a cap assembly, wherein the cap assembly is in the shape of a circular conduit, wherein the cap assembly is one of the following: i) a slit port cap assembly, wherein the slit port cap assembly includes the self-sealing membrane having a slit port, does not include a filter membrane and has a proximal end and a distal end with respect to the anterior side of the mask body; ii) a filtered slit port cap assembly, wherein the filtered slit port cap assembly includes the self-sealing membrane having a slit port surrounded by a filter membrane and has a proximal end and a distal end with respect to the anterior side of the mask body, wherein the self-sealing membrane of the slit port cap or the filtered slit port cap is capable of providing a seal between an instrument inserted through the slit port.

A subsequent embodiment of the filtering facepiece respirator including any of the previous or subsequent embodiments includes a method of instrumenting an airway to the filtering facepiece respirator having the following steps: providing a mask body having an anterior side, a posterior side, a middle portion, a first side portion, a second side portion, a top side portion, a bottom side portion and outer edge portions; providing a primary port positioned on the mask body; providing a self-sealing membrane, wherein the self-sealing membrane is made of silicone, a transparent thermoplastic elastomer or a medical grade rubber; providing a detachable primary port adapter, wherein the detachable primary port adapter is positioned over and engages the primary port, wherein the detachable primary port adapter includes a cap assembly, wherein the cap assembly is in the shape of a circular conduit, wherein the cap assembly is one of the following: i) a slit port cap assembly, wherein the slit port cap assembly includes a self-sealing membrane having a slit port, does not include a filter membrane and has a proximal end and a distal end with respect to the anterior side of the mask body; ii) a filtered slit port cap assembly, wherein the filtered slit port cap assembly includes a self-sealing membrane having a slit port surrounded by a filter membrane and has a proximal end and a distal end with respect to the anterior side of the mask body; providing an instrument, wherein the instrument is insertable through an opening formed by a slit in the slit port cap assembly or a slit in the filtered slit port cap assembly through the mask body and into the posterior side of the mask body; wherein the self-sealing membrane of the slit port cap or the filtered slit port cap provides a seal between the instrument and the filtering facepiece respirator, wherein the above steps are capable of being performed while the filtering facepiece respirator is positioned on a patient or off a patient.

A subsequent embodiment of the filtering facepiece respirator including any of the previous or subsequent embodiments includes a method of instrumenting an airway to the filtering facepiece respirator including the following steps: providing the slit port cap assembly or filtered cap assembly engageable to the primary port of the mask body; engaging the slit port cap assembly or the filtered cap assembly to the primary port of the mask body; providing an instrument, wherein the instrument is engageable to the primary port of the mask body or providing an instrument, wherein the instrument is insertable through an opening formed by a slit in the slit port cap assembly through the mask body and into the posterior side of the mask body; removing the slit port cap assembly or the filtered cap assembly from the primary port of the mask body and engaging the instrument to the primary port of the mask body or inserting the instrument through the opening formed in the slit of the slit port cap assembly through the mask body and into the posterior side of the mask body; wherein the slit port cap provides a seal between the instrument and the filtering facepiece respirator, wherein the above steps are capable of being performed while the filtering facepiece respirator is positioned on a patient or off a patient.

A subsequent embodiment of the filtering facepiece respirator including any of the previous or subsequent embodiments includes a method of making a filtering facepiece respirator including the following steps: providing a mask body having an anterior side, a posterior side, a middle portion, a first side portion, a second side portion, a top side portion, a bottom side portion and outer edge portions; providing a primary port positioned on the mask body; providing a self-sealing membrane or a filter membrane, wherein the self-sealing membrane is comprised of silicone, a transparent thermoplastic elastomer or a medical grade rubber; integrating the self-sealing membrane or the filter membrane into a detachable primary port adapter, wherein the detachable primary port adapter is positioned over and engages the primary port, wherein the detachable primary port adapter comprises a cap assembly, wherein the cap assembly is in the shape of a circular conduit, wherein the cap assembly is i.) a slit port cap assembly, wherein the slit port cap assembly comprises the self-sealing membrane having a slit port, does not include a filter membrane and has a proximal end and a distal end with respect to the anterior side of the mask body, wherein the self-sealing membrane of the slit port cap is capable of providing a seal between an instrument inserted through the slit port; or ii.) a filtered cap assembly, wherein the filtered cap assembly comprises the filter membrane and has a proximal end and a distal end with respect to the anterior side of the mask body.

SECOND LISTING OF REFERENCE NUMBERS 1. filtering facepiece respirator (100)
2. mask body (102)
3. nose bridge (104)
4. fasteners (clip) for bands (106)
5. primary port (108)
6. first rib or flange of port (110)
7. adapter/cap assembly (112)
8. ribs or flanges of adapter/cap assembly (114)
9. first rib or flange of adapter/cap assembly (116)

10. recessed portion within port (118)
11. second rib or flange of adapter/cap assembly (120)
12. second rib or flange of port (122)
13. filtered cap assembly (124)
14. filter membrane (126)
15. slit port (128)
16. circular inner frame of cap assembly (130)
17. frame extensions of cap assembly (130)
18. inner surface of assembly (134)
19. self-sealing slit port (136)
20. filtered slit port cap assembly (138)
21. oxygen port (140)
22. outer aperture of oxygen port (142)
23. inner aperture of oxygen port (144)
24. oxygen port adapter (146)
25. luer port (148)
26. outer aperture of luer port (150)
27. inner aperture of luer port (152)
28. luer port adapter (154)
29. edges of mask body (156)
30. primary port adapter (158)
31. oxygen port adapter/breathing bag/non-rebreathing bag/non-rebreathing bag adapter (160)
32. cardiopulmonary resuscitation (CPR) adapter (162)
33. cardiopulmonary resuscitation (CPR) device (164)
34. continuous positive airway pressure (CPAP) adapter/bilevel positive airway pressure (BIPAP) adapter (166)
35. tracheal intubation (168)
36. tube/catheter (170) attached to luer port for diverting respiratory particles
37. nebulizer (172)
38. Venturi adapter (174)
39. exhalation valve (176)

While the filtering facepiece respirator or mask provided herein has been described in connection with various illustrative embodiments, it is to be understood that other similar embodiments may be used, or modifications and additions may be made to the described embodiments for performing the same function disclosed herein without deviating therefrom. Further, all embodiments disclosed are not necessarily in the alternative, as various embodiments may be combined or subtracted to provide the desired characteristics. Variations can be made by one having ordinary skill in the art without departing from the spirit and scope hereof. Therefore, the filtering facepiece respirator or mask should not be limited to any single embodiment, but rather construed in breadth and scope in accordance with the recitations of the appended claims.

What is claimed is:

1. A filtering facepiece respirator comprising:
a mask body having an anterior side, a posterior side, a middle portion, a first side portion, a second side portion, a top side portion, a bottom side portion and an outer edge portion, wherein the mask body is comprised of a filter media material, wherein the filter media material comprises multiple microfiber filtering layers of varying thickness and polypropylene and polyester polyfiber compositions that provide rigidity and filtering functionality;
a primary port positioned on the mask body;
fasteners for attaching and securing adjustable bands to the first side portion and to the second side portion of the mask body; and,
a detachable primary port adapter which is positioned over and engages the primary port, wherein the detachable primary port adapter comprises a cap assembly, wherein the cap assembly is in the shape of a circular conduit having an outside surface, an inside surface, and a membrane, wherein the membrane is positioned within the circular conduit and is attached perpendicularly with respect to the inside surface of the circular conduit that forms the cap assembly,
wherein the cap assembly comprises a slit port cap assembly, wherein the membrane of the slit port cap assembly comprises a self-sealing membrane having a slit port, does not include a filter membrane and has a proximal end and a distal end with respect to the anterior side of the mask body,
wherein the self-sealing membrane of the slit port cap assembly is positioned within the circular conduit and attached perpendicularly with respect to the inside surface of the circular conduit that forms the slit port cap assembly.

2. The filtering facepiece respirator of claim 1, wherein the mask body comprises a nose bridge positioned at the top side portion of the mask body, wherein the mask body is comprised of silicone or a medical grade plastic material and wherein the mask body is transparent.

3. The filtering facepiece respirator of claim 1, wherein the cap assembly comprises a first end and a second end, wherein the first end of the cap assembly comprises a snap coupling, screw threads or a tabular protrusion for engaging the cap assembly to the primary port,
wherein the snap coupling is formed by at least two flanges on the cap assembly forming a space therebetween, wherein the two flanges on the cap assembly are capable of engaging a flange positioned on the primary port in the space formed between the two flanges of the cap assembly, and
wherein the tabular protrusion is capable of engaging a receiving structure in the primary port.

4. The filtering facepiece respirator of claim 3, wherein the self-sealing membrane of the slit port cap assembly is comprised of silicone, a transparent thermoplastic elastomer or a medical grade rubber and wherein the slit port in the self-sealing membrane is capable of receiving and sealing an instrument inserted therethrough.

5. The filtering facepiece respirator of claim 1, wherein the mask body further comprises an oxygen port positioned on the mask body.

6. The filtering facepiece respirator of claim 5, wherein the oxygen port is capable of engaging an oxygen port adapter, a breathing bag, a non-rebreathing bag, a non-rebreathing bag adapter, a nebulizer and a Venturi oxygen adapter.

7. The filtering facepiece respirator of claim 6, wherein the primary port, upon removal of the detachable primary port adapter cap assembly is capable of engaging one of the following: an adapter for oxygen delivery, a cardiopulmonary resuscitation (CPR) adapter, a continuous positive airway pressure (CPAP) adapter, a bilevel positive airway pressure (BIPAP) adapter, an adapter for delivery of anesthesia, an adapter for nebulized medications/substances; an aerosol shell adapter, an adapter for a PEEP valve attachment, an adapter for a device for taking breath samples with vacuum tubes, an adapter for an electronic device for measurement of spirometry/$CO_2$/temperature, an adapter for a humidifying and/or vaporizing device; an adapter for an electronic breathalyzer device, an adapter for an electronic nicotine delivery system, and an adapter for a UV light device.

8. A method of instrumenting an airway to the filtering facepiece respirator according to claim 7 comprising:

providing the slit port cap assembly engageable to the primary port of the mask body;

engaging the slit port cap assembly to the primary port of the mask body;

providing an instrument, wherein the instrument is engageable to the primary port of the mask body or providing an instrument, wherein the instrument is insertable through an opening formed by a slit in the slit port cap assembly through the mask body and into the posterior side of the mask body;

removing the slit port cap assembly from the primary port of the mask body and engaging the instrument to the primary port of the mask body or inserting the instrument through the opening formed in the slit of the slit port cap assembly through the mask body and into the posterior side of the mask body;

wherein the slit port cap provides a seal between the instrument and the filtering facepiece respirator, wherein the above steps are capable of being performed while the filtering facepiece respirator is positioned on a patient or off a patient.

9. The filtering facepiece respirator of claim 5, wherein the oxygen port comprises a filter membrane and a filter frame positioned on the posterior side of the mask body.

10. The filtering facepiece respirator of claim 1, wherein the mask body further comprises a luer port positioned on the mask body.

11. The filtering facepiece respirator of claim 10, wherein the luer port comprises a luer port adapter, wherein the luer port adapter comprises a capped luer lock and provides an aperture through the mask body.

12. The filtering facepiece respirator of claim 10, wherein the luer port comprises a filter membrane and a filter frame positioned on the posterior side of the mask body, wherein an aperture within a capped luer lock is surrounded by the filter membrane of the luer port.

13. The filtering facepiece respirator of claim 1, further comprising an exhalation valve position on the mask body or the self-sealing membrane of the cap assembly.

14. The filtering facepiece respirator of claim 1, wherein the filter media comprises an electroceutical fabric.

15. The filtering facepiece respirator of claim 1, wherein the mask body is further comprised of silicone or a medical grade plastic material.

16. The filtering facepiece respirator of claim 15, wherein the mask body is transparent.

17. The filtering facepiece respirator of claim 1, wherein the detachable primary port adapter comprises a 22 mm cap assembly.

18. A method of making a filtering facepiece respirator of claim 1 comprising:

providing a mask body having an anterior side, a posterior side, a middle portion, a first side portion, a second side portion, a top side portion, a bottom side portion and outer edge portion;

providing a primary port positioned on the mask body;

providing a self-sealing membrane, wherein the self-sealing membrane is further comprised of silicone, a transparent thermoplastic elastomer or a medical grade rubber;

integrating the self-sealing membrane into a detachable primary port adapter, wherein the detachable primary port adapter is positioned over and engages the primary port, wherein the detachable primary port adapter comprises a cap assembly, wherein the cap assembly is in the shape of a circular conduit, wherein the cap assembly is a slit port cap assembly, wherein the slit port cap assembly comprises the self-sealing membrane having a slit port, does not include a filter membrane and has a proximal end and a distal end with respect to the anterior side of the mask body, wherein the self-sealing membrane of the slit port cap is capable of providing a seal between an instrument inserted through the slit port.

19. A filtering facepiece respirator comprising:

a mask body having an anterior side, a posterior side, a middle portion, a first side portion, a second side portion, a top side portion, a bottom side portion and outer edge portion, wherein the mask body is comprised of a filter media material, wherein the filter media material comprises multiple microfiber filtering layers of varying thickness and polypropylene and polyester polyfiber compositions that provide rigidity and filtering functionality;

a primary port positioned on the mask body;

fasteners for attaching and securing adjustable bands to the first side portion and to the second side portion of the mask body; and, a detachable primary port adapter which is positioned over and engages the primary port, wherein the detachable primary port adapter comprises a cap assembly, wherein the cap assembly is in the shape of a circular conduit, wherein the cap assembly comprises a slit port cap assembly, wherein the slit port cap assembly comprises a self-sealing membrane having a slit port, does not include a filter membrane and has a proximal end and a distal end with respect to the anterior side of the mask body.

* * * * *